Figure 1A:
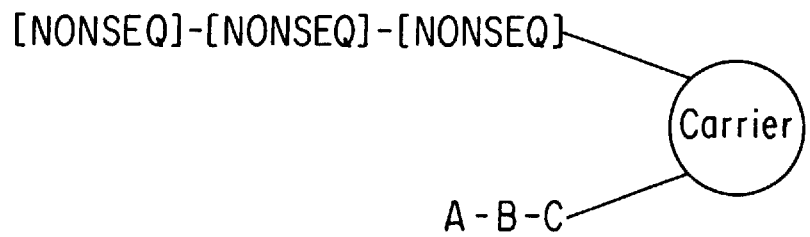

United States Patent [19]
Lebl et al.

[11] Patent Number: 5,840,485
[45] Date of Patent: Nov. 24, 1998

[54] TOPOLOGICALLY SEGREGATED, ENCODED SOLID PHASE LIBRARIES

[75] Inventors: Michal Lebl, Oro Valley; Kit S. Lam; Sydney E. Salmon, both of Tucson; Victor Krchnak, Oro Valley; Nikolai Sepetov, Oro Valley; Peter Kocis, Oro Valley, all of Ariz.

[73] Assignee: Selectide Corporation, Del.

[21] Appl. No.: 249,830

[22] Filed: May 26, 1994

Related U.S. Application Data

[63] Continuation-in-part of Ser. No. 68,327, May 27, 1993, abandoned.

[51] Int. Cl.$^6$ ............ C12Q 1/68; G01N 33/53; C07K 17/02; C07H 21/04
[52] U.S. Cl. ................ 435/6; 435/7.1; 530/300; 530/323; 436/518; 536/23.1; 935/77; 935/78
[58] Field of Search .......... 435/6, 7.1; 436/518; 530/333, 334, 300, 345, 323, 812; 536/23.1, 24.3

[56] References Cited

U.S. PATENT DOCUMENTS

| | | | |
|---|---|---|---|
| 5,182,366 | 1/1993 | Heubner et al. | 530/334 |
| 5,288,514 | 2/1994 | Ellman | 427/2 |

FOREIGN PATENT DOCUMENTS

| | | | |
|---|---|---|---|
| 0 639 584 A1 | 2/1995 | European Pat. Off. | C07K 1/04 |
| WO 91/19735 | 12/1991 | WIPO. | |
| WO 92/00091 | 1/1992 | WIPO. | |
| WO 93/06121 | 4/1993 | WIPO. | |
| WO 93/20242 | 10/1993 | WIPO. | |
| WO 94/08051 | 4/1994 | WIPO. | |

OTHER PUBLICATIONS

Baum, 1993, Solid–phase synthesis of benzodiazepines, Chemical and Engineering News 71:33.
Brenner and Lerner, 1992, Encoded combinatorial chemistry, Proc Nat Acad Sci USA 89:5381–5383.
Bunin and Ellman, 1992, A general and expedient method for the solid–phase synthesis of 1,4 diazepine derivatives, J Am Chem Soc 114:10997–10998.
Furka et al, 1991, General method for rapid synthesis of multicomponent peptide mixtures, Int J Pept Prot Res 37:487–493.
Gallop et al., 1994, Applications of combinatorial technologies of drug discovery. 1. Background and peptide combinatorial libraries, J Medicinal Chemistry 37(9):1233–1251.
Gordon et al., 1994, Applications of combinatorial technologies to drug discovery. 2. Combinatorial organic synthesis, library screening strategies, and future directions, J Medicinal Chemistry 37(10)1385–1401.
Kerr et al., 1993, Encoded combinatorial peptide libraries containing non–natural amino acids, J Am Chem Soc 115(6):2529–2531.
Lam et al., 1993, The chemical synthesis of large random peptide libraries and their use for the discovery of ligands for macromolecular acceptors, Bioorg Med Chem Lett 3:419–429.
Lam et al., 1991, A new type of synthetic peptide library for identifying ligand binding activity, Nature 354:82–85.
Lam and Lebl, 1992, Streptavidin and avidin recognize peptide ligands with different motifs, Immunomethods 1:1–15.
Lebl et al., 1994, Construction and Screening of Libraries of peptide and non–peptide structures, Techniques in Protein Chemistry V:541–548.
Needles et al., 1993, Generation and screening of an oligonucleotide–encoded synthetic peptide library, PNAS USA 90:10700–10704.
Nikolaiev et al., Peptide–encoding for structure determination of nonsequenceable polymers within libraries synthesized and tested of solid–phase supports, Peptide Research 6(3):161–170.
Ohlmeyer et al., 1993, Complex synthetic chemical libraries indexed with molecular tags, PNAS USA 90:10922–10926.
Simon et al., 1992, Peptoids: a modular approach to drug discovery, PNAS USA 89:9367–9371.
Vagner et al., Novel methodology for differentiation of surface and interior areas of polyoxyethylene–polystyrene (POE–PS) supports: application to library screening procedures, in "Innovationns and Perspectives in Solid Phase Synthesis and Related Technologies" (R. Epton ed.); corresponding to the Third International Symposium organized by Roger Epton. Aug. 31–Sep. 4, 1993, Oxford, England.

*Primary Examiner*—Stephanie W. Zitomer
*Attorney, Agent, or Firm*—Pennie & Edmonds LLP

[57] ABSTRACT

The invention relates to libraries of synthetic test compound attached to separate phase synthesis supports that also contain coding molecules that encode the structure of the synthetic test compound. The molecules may be polymers or multiple nonpolymeric molecules. The synthetic test compound can have backbone structures with linkages such as amide, urea, carbamate (i.e., urethane), ester, amino, sulfide, disulfide, or carbon-carbon, such as alkane and alkene, or any combination thereof. Examples of subunits suited for the different linkage chemistries are provided. The synthetic test compound can also be molecular scaffolds, such as derivatives of monocyclic of bicyclic carbohydrates, steroids, sugars, heterocyclic structures, polyaromatic structures, or other structures capable of acting as a scaffolding. Examples of suitable molecular scaffolds are provided. The invention also relates to methods of synthesizing such libraries and the use of such libraries to identify and characterize molecules of interest from among the library of synthetic test compound.

47 Claims, 8 Drawing Sheets

1. TG + Br-CH2CH2CH2COOH
2. +Boc-Cys(R)-OMe
3. TFA
4. Fmoc-Dab(Boc)-OH/DIC/HOBt
5. TFA
6. R-COOH/DIC/HOBt
7. Pip/DMF
8. Fmoc-Dab(Boc)OH/DIC/HOBt
.
.
.
n. NaOH
n+1. DIC/HOBt

TOPOLOGICALLY SEGREGATED, ENCODED SOLID PHASE LIBRARIES

The present application is a continuation-in-part of application Ser. No. 08/068,327, filed on May 27, 1993, now abandoned, which is incorporated herein by reference in its entirety.

TABLE OF CONTENTS
1. FIELD OF THE INVENTION
2. BACKGROUND OF THE INVENTION
3. SUMMARY OF THE INVENTION
4. BRIEF DESCRIPTION OF THE DRAWINGS
5. DETAILED DESCRIPTION OF THE INVENTION
   - 5.1 CODING STRATEGIES
   - 5.2 METHODS FOR GENERATING A LIBRARY OF SYNTHETIC TEST COMPOUND
   - 5.3 DEVELOPMENT AND USE OF SEPARATE PHASE SYNTHESIS SUPPORTS AND LINKERS IN ENCODED MOLECULAR LIBRARY SYNTHESES
     - 5.3.1 SUPPORTS AND LINKERS USEFUL IN ENCODED MOLECULAR LIBRARY SYNTHESIS
     - 5.3.2 TOPOLOGY OF ANCHORING OF SYNTHETIC TEST COMPOUND AND CODING MOLECULES ON SOLID SUPPORT SURFACES
   - 5.4 STRATEGY FOR CARRYING OUT ALTERNATINGSYNTHESES OF THE CODING AND SYNTHETIC TEST COMPOUNDS MOLECULES DURING THE GENERATION OF ENCODED LIBRARIES
   - 5.5 SPECIFIC LIBRARIES OF TEST COMPOUNDS AND METHODS OF SYNTHESIS THEREOF
     - 5.5.1 LIBRARIES CONTAINING AMIDE BONDS WITH SUBUNITS OTHER THAN $\alpha$-AMINO ACIDS
     - 5.5.2 LIBRARIES CONTAINING CARBAMATE BONDS
     - 5.5.3 LIBRARIES CONTAINING UREA BONDS
     - 5.5.4 LIBRARIES CONTAINING ESTER BONDS
     - 5.5.5 LIBRARIES CONTAINING AMINE BONDS
     - 5.5.6 LIBRARIES CONTAINING SULFIDES AND DISULFIDE BONDS
     - 5.5.7 LIBRARIES CONTAINING CARBON-CARBON BONDS
     - 5.5.8 LIBRARIES OF POLYCYCLIC COMPOUNDS AND FUNCTIONALIZED POLYCYCLIC COMPOUNDS
     - 5.5.9 LIBRARIES OF POLYSUBSTITUTED RING STRUCTURES CAPABLE OF SERVING AS A SCAFFOLDING
     - 5.5.10 LIBRARIES BASED ON SCAFFOLDING CONSTRUCTED FROM AMINO ACIDS
   - 5.6 METHODS OF DETECTION AND IDENTIFICATION OF LIGANDS IN LIBRARIES OF TEST COMPOUNDS
     - 5.6.1 BINDING ASSAYS
     - 5.6.2 BIOACTIVITY ASSAYS
     - 5.6.3 ENZYME MIMICS/ENZYME INHIBITORS
     - 5.6.4 TOPOLOGICAL SEGGREGATION
   - 5.7 METHODS OF CHARACTERIZING A SYNTHETIC TEST COMPOUND FROM A LIBRARY
     - 5.7.1 CHARACTERIZATION BY MEANS OF SINGLE AND MULTIPLE SEQUENTIAL CODES
     - 5.7.2 CHARACTERIZATION BY MEANS OF A NON-SEQUENTIAL CODE
     - 5.7.3 NON-CODED LIBRARIES
   - 5.8 THERAPEUTIC AND DIAGNOSTIC AGENTS FROM LIBRARIES OF SYNTHETIC TEST COMPOUND
6. EXAMPLE: A MODEL ENCODED LIBRARY
   - 6.1 MATERIALS AND METHODS
   - 6.2 RESULTS
     - 6.2.1 SYNTHESIS OF MODEL LIBRARY AND DEPROTECTION OF BOTH PROTECTING GROUPS
     - 6.2.2 DEPROTECTION OF N-TERMINAL FMOC GROUP AND ACETYLATION OF THE "FMOC BRANCH"
     - 6.2.3 REPLACEMENT OF THE BOC PROTECTING GROUP WITH THE TFA GROUP
     - 6.2.4 CLEAVAGE OF A PEPTIDE FROM ONE BEAD
   - 6.3 DISCUSSION
7. EXAMPLE: NON-PEPTIDE LIBRARIES CODED BY A PEPTIDE STRUCTURE
   - 7.1 MATERIALS AND METHODS
   - 7.2 RESULTS
     - 7.2.1 SYNTHESIS OF TWO FORMS OF ENCODED LIBRARY
     - 7.2.2 SYNTHESIS OF REPRESENTATIVE COMPOUNDS FROM THE NON-PEPTIDE LIBRARY
   - 7.3 DISCUSSION
8. EXAMPLE: LIBRARY: XXXX-Lys(XXXX)-Lys(ZZ)-$\beta$Ala-Gly-$\beta$Ala-Gly-TG
   - 8.1 MATERIALS AND METHODS
     - 8.1.1 SYNTHESIS OF THE LIBRARY
     - 8.1.2 SCREENING PROTOCOL OF THE LIBRARY
   - 8.2 RESULTS AND DISCUSSION
9. EXAMPLE: LIBRARIES OF NON-PEPTIDE STRUCTURES BASED ON SOLID PHASE PEPTIDE SYNTHESIS CHEMISTRY
   - 9.1 MATERIALS AND METHODS
     - 9.1.1 INSTRUMENTS
     - 9.1.2 PROCEDURES
     - 9.1.3 REAGENTS
     - 9.1.4 SYNTHESIS OF A NONPEPTIDIC LIBRARY ON NONPEPTIDIC SCAFFOLDING
     - 9.1.5 BRANCHED LIBRARY ON TENTAGEL
     - 9.1.6 BRANCHED ENCODED LIBRARY ON TENTAGEL
     - 9.1.7 BRANCHED LIBRARY WITH CODING ON FAST FLOW SEPHAROSE (FFS)
     - 9.1.8 LIBRARY OF MIXED PEPTIDE AND NON-PEPTIDE SUBUNITS
     - 9.1.9 SCREENING PROTOCOL OF THE LIBRARY
   - 9.2 RESULTS AND DISCUSSION
10. EXAMPLE: SELECTIVE ACTIVATION OF SURFACE FUNCTIONAL GROUPS ON A RESIN BEAD
    - 10.1 MATERIALS AND METHODS
      - 10.1.1 REMOVAL OF THE SURFACE CONTENT OF THE PEPTIDE FROM SOLID PHASE BEAD
      - 10.1.2 SYNTHESIS OF DIFFERENT PEPTIDES ON THE SURFACE AND INSIDE OF THE POLYMERIC BEAD
    - 10.2 RESULTS AND DISCUSSION
    - 10.3 DISCUSSION
11. EXAMPLE: PREFERENTIAL BLOCKING OF THE FREE AMINO GROUPS ON THE SURFACE OF A TENTAGEL BEAD
    - 11.1 MATERIALS AND METHODS
    - 11.2 RESULTS AND DISCUSSION 12. EXAMPLE: SUBUNITS SUITABLE FOR THE CONSTRUCTION OF NONPEPTIDIC LIBRARIES
   12.1 ACYLATION OF PRIMARY AMINO GROUP
   12.2 NUCLEOPHILIC DISPLACEMENT OF HALOGEN BY AMINES
   12.3 REDUCTIVE ALKYLATION
   12.3.1 GENERALIZED METHODS
   12.3.2 SPECIFIC METHODS
13. EXAMPLE: NON-SEQUENTIAL CODING OF A LIBRARY
   13.1 INSTRUMENTS, MATERIALS AND PROCEDURES
   13.2 SYNTHESIS OF MODEL SEQUENCES
   13.2.1 MATERIALS AND METHODS
   13.2.2 MODEL COMPOUNDS YGAF AND FGAF CONSTRUCTED WITH CODING
   13.3 SYNTHESIS OF THE DIAMINOBENZOIC ACID BASED LIBRARY WITH DIGITAL CODING
   13.3.1 MATERIALS AND METHODS
   13.3.2 SYNTHESIS OF THE LIBRARY
14. EXAMPLE: MOLECULAR SCAFFOLDS

1. FIELD OF THE INVENTION

The invention relates to libraries of synthetic test compound attached to separate phase synthesis supports. In particular, the invention relates to libraries of synthetic test compound attached to separate phase synthesis supports that also contain coding polymeric sequences that encode the structure of the synthetic test compound. Each of the solid phase synthesis support beads contains a single type of synthetic test compound and a single, unique and readily determinable coding polymeric sequence encoding the structure of the synthetic test compound. The synthetic test compound can have backbone structures with linkages such as amide, urea, carbamate (i.e., urethane), ester, amino, sulfide, disulfide, or carbon-carbon, such as alkane and alkene, or any combination thereof. The synthetic test compound can also be molecular scaffolds, such as derivatives of monocyclic or bicyclic carbohydrates, steroids, sugars, heterocyclic structures, polyaromatic structures, or other structures capable of acting as a scaffolding. The invention also relates to methods of synthesizing such libraries and the use of such libraries to identify and characterize molecules of interest from among the library of synthetic test compound.

2. BACKGROUND OF THE INVENTION

Ligand recognition and binding regulates almost all biological processes, including immune recognition, cell signalling and communication, transcription and translation, intracellular signalling, and enzymatic catalysis. As a result, there is a longstanding interest in the art in identifying molecules which can be used as follows: to serve as agonists or antagonists of ligands such as hormones, growth factors, or neurotransmitters; to induce B-cell (antibody-mediated) or T-cell (cell-mediated) immunity; to induce catalysis of chemical reactions; and to regulate gene expression at the level of transcription or translation. A main reason for this interest is the desire to directly use these biologically active molecules as drugs or, if necessary, to convert these molecules into derivatives which can function as drugs.

Many biological ligands are proteins or peptides. This list includes the majority of hormones, growth factors, neuroactive molecules, and immune epitopes. For this reason, initial efforts to develop agonists or antagonists of receptor- or enzyme-mediated biological activities involved peptide design and synthesis. However, peptides that have been found to possess desirable biological activities are often unsuitable as drugs. To become drugs, the peptides often need to be converted to derivatives or structural analogs, i.e., peptide mimetics, which, unlike most peptides, possess satisfactory pharmacokinetics and stability properties. Many publications describing the development of medicinally useful or promising peptidomimetics have appeared; some recent examples include Rudy Baum, in *Chemical & Engineering News*, Jan. 18, 1993, page 33; Hirschmann, R. et al. *J. Am. Chem. Soc.,* 1992, 114, 9699–9701; Hirschmann, R. et al. *J. Am. Chem. Soc.,* 1992, 114, 9217–9218.

The discovery of biologically active compounds can be a difficult, time-consuming, and extremely expensive process. A key problem in this area is the identification of a single chemical structure, out of a large number of possible relevant structures, that possesses the desired properties. When the discovery process employs a sequential strategy of structure-design, synthesis, and biological testing, the identification of a desirable chemical structure becomes extremely laborious. To circumvent this highly demanding task, libraries of large numbers of molecules of diverse structures can be prepared. Ideally such libraries can be screened and evaluated rapidly.

Much of the work in this area of library synthesis and screening has been done with peptides, e.g., the approaches of Geysen (Geysen et al. *Molecular Immunology,* 1986, 23, 709–715; Geysen et al. *J. Immunologic Methods,* 1987, 102, 259–274), Fodor (Fodor et al., *Science,* 1991, 251, 767–773) and Houghten (Houghten et al., *Nature,* 1991, 354, 84–86). However, such libraries are limited in terms of the number of possible structural variants that can be prepared, tested and identified in a given experiment.

The invention of truly random libraries of polymeric synthetic test compound, in which a single polymeric species arising from a combination of subunits is attached to a single solid support, marked a breakthrough in the discovery of biologically active compounds which are peptides or, very importantly, peptide mimetics (see, U.S. patent application Ser. No. 07/717,454, filed Jun. 19, 1991, entitled "Random Bio-Oligomer Library, a Method of Synthesis Thereof, and a Method of Use Thereof" and U.S. patent application Ser. No. 07/456,845, filed Jul. 2, 1990, entitled "Random Peptide Library, a Method of Synthesis Thereof and a Method of Use Thereof").

Nonpeptidic organic compounds, such as peptide mimetics, can often surpass peptide ligands in affinity for a certain receptor or enzyme. The binding of biotin and avidin, the tightest ever recorded, involves association of a nonpeptidic organic structure (biotin) with a protein (avidin). An effective strategy for rapidly identifying high affinity biological ligands, and ultimately new and important drugs, requires rapid construction and screening of diverse libraries of non-peptidic structures containing a variety of structural units capable of establishing one or more types of interactions with a biological acceptor (e.g., a receptor or enzyme), such as hydrogen bonds, salt bridges, $\pi$-complexation, hydrophobic effects, etc. However, work on the generation and screening of synthetic test compound libraries containing nonpeptidic molecules is now in its infancy. One example from this area is the work of Ellman and Bunin on a combinatorial synthesis of benzodiazepines on a solid support (*J. Am. Chem. Soc.* 114, 10997, (1992); see *Chemical and Engineering News,* Jan. 18, 1993, page 33).

A key unsolved problem in the area of generation and use of nonpeptide libraries is the elucidation of the structure of molecules selected from a library that show promising biological activity.

An attempt to uncover the structures of peptides selected from a library using unique nucleotide sequence codes, which are synthesized in tandem with the peptide library, has recently been described by Brenner and Lerner (Brenner, S. and Lerner, R. A. *Proc. Nat'l. Acad. Sci. USA,* 1992 89, 5381–5383). The nucleotide sequence of the code attached to each peptide must be amplifiable via the polymerase chain reaction (PCR). However, nucleotide synthesis techniques are not compatible with all of the synthetic techniques required for synthesis of many types of molecular libraries. Furthermore, the close proximity of nucleotide and synthetic test compound in the library, which can result in interactions between these molecules interfering with the binding of the ligand with a target receptor or enzyme during the biological assay, also limits this approach. The nucleotide component of the library can also interfere during biological assays in a variety of other ways.

Kerr et al. (*J. Am. Chem. Soc.,* 1993, 115, 2520–2531) reported synthesizing solution phase libraries of peptides, containing non-natural amino acid residues, in parallel with peptide coding strands. The peptide ligand and its coding strand in this library are covalently joined together, which allows isolation and sequence determination of pairs of synthetic test compound and corresponding code. However, as with the nucleic-acid-encoded library described by Brenner and Lerner, supra, the coding peptide may interfere with the screening assay. Moreover, the requirement for purification of sufficient amounts of material from the library with the affinity selection method, in order to obtain the sequence of the coding peptides, precludes synthesis of libraries of more than a few thousand species.

Thus, there is a need in the art for new, general, and versatile methods for generating and screening libraries of compounds belonging to a variety of chemical classes. There is a further need for effective methods for elucidating the structures of compounds selected from the library as a result of screening, whose structures cannot be determined by traditional techniques, e.g., Edman degradation or mass spectrometry alone. Yet another need in the art is a molecular coding system that will not interact in screening assays or influence the binding of the synthetic test compound through proximity effects.

Citation or identification of any reference herein shall not be construed as an admission that such reference is available as prior art to the present invention.

3. SUMMARY OF THE INVENTION

The present invention is directed to libraries of synthetic test compound attached to separate phase supports, in which a single species of compound is attached to each support. The compounds can have linkages such as, but not limited to, amide, urea, ester, ether, carbamate, amine, sulfide, disulfide, carbon-carbon, such as alkane, alkene and alkyne, and the like. In particular, the compounds can be polyamides, polyureas, polyurethanes, polyesters, polyethers, polycarbonates, polyamines, polyalkanes, polysulfides, polydisulfides, or polymers containing any combination of such bonds. The compound may also be a molecular scaffold having various substituents at defined positions, in which the scaffold can be a cyclic or bicyclic hydrocarbon, a steroid, a sugar, a heterocyclic structure, or a polycyclic aromatic molecule.

The present invention further relates to encoded libraries of synthetic test compound, in which a sequence of a coding molecule on a separate phase support represents to, i.e., encodes, the synthetic test compound attached to the support. In a preferred embodiment, the coding molecule is a peptide. An alternative embodiment encompasses the coding of a library of sequencable test compounds, wherein certain subunits are indistinguishable by conventional sequencing techniques. The coding is accomplished by adding a small fraction of a third distinguishable coding subunit to the coupling mixture. In this coding technique, called fractional coding, there is no discrete coding molecule at all.

The invention also provides encoded libraries in which the synthetic test compound is topologically segregated from the coding molecule on each separate phase support. In a preferred embodiment, in which the separate phase support is a resin bead, the synthetic test compound is located on the surface of the resin bead while the coding molecule is located in great abundance in the interior of the bead. In another embodiment, the synthetic test compound is attached to the separate phase support by a cleavable linker, and the coding molecule is attached to the support with a non-cleavable linker or a separately cleavable linker. In this embodiment, during a screening assay, the synthetic test compound can be released from the separate phase support, e.g., into solution, while the coding molecule remains attached to the support.

The present invention is also directed to methods of synthesis of the libraries of synthetic test compound and encoded libraries of synthetic test compound. Synthesis of the synthetic test compound involves separation of portions of the separate phase supports, and reaction with a single subunit of the synthetic test compound with each portion under conditions such that the added subunit can react with functional groups on the synthetic test compound. If an encoded library is to be prepared, the subunit of the coding molecule that corresponds to the subunit of the compound is added to each of the separated portions before they are recombined, using a separate set of reaction conditions such that the coding subunit will only react with the coding components of the separate phase support. The order of reaction, described as linking the synthetic test compound subunit followed by the coding subunit is not material. The order could just as well be coding subunit reaction followed by the synthetic test compound subunit. What is important is that both reactions are carried out on the same portion of the solid phase support.

After the separate coupling steps, the portions are thoroughly mixed in order to randomize them. The process of separate coupling and thorough mixing is repeated until as many subunits of the compound have been added as is desired. Then any functional group protecting groups that remain on the compounds (and the coding sequence, if any) are removed, without cleaving either the compounds or the coding molecules from the separate phase support.

The present invention is also directed to methods for screening the libraries. The libraries can be screened for binding activity of an acceptor molecule on the separate phase support, or for binding activity of the released compound. The invention further provides for biological screening assays of the released compounds.

Other screening assays for the compounds, such as, but not limited to, enzyme activity, electron transport activity, and photo activity, to mention a few, are also contemplated by the invention.

Solid supports that contain compounds that demonstrate the activity of interest in the screening assay are selected. The structure of the compound is determined, e.g., by mass spectrometry, nuclear magnetic resonance spectrometry, or other spectrometric methods. Preferably, the library is an encoded library, in which case the structure of the compound is encoded by the sequence of the coding molecule, which can be readily determined.

The compounds of the present invention can provide leads for therapeutic or diagnostic agents. More preferably, the compounds themselves may be useful therapeutic or diagnostic agents. The compounds on separate phase supports can also be useful for electron transport, e.g., as transistors or semiconductors.

4. BRIEF DESCRIPTION OF THE DRAWINGS

Figure 1B:
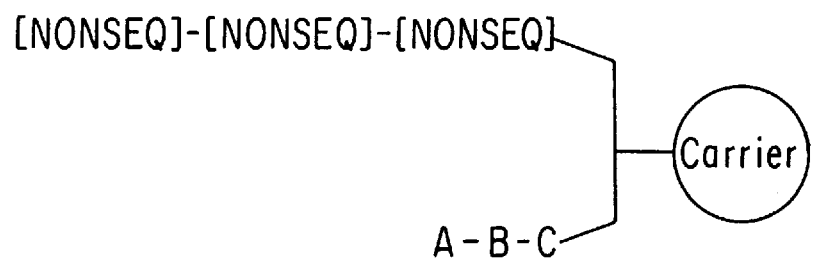
Figure 1C:
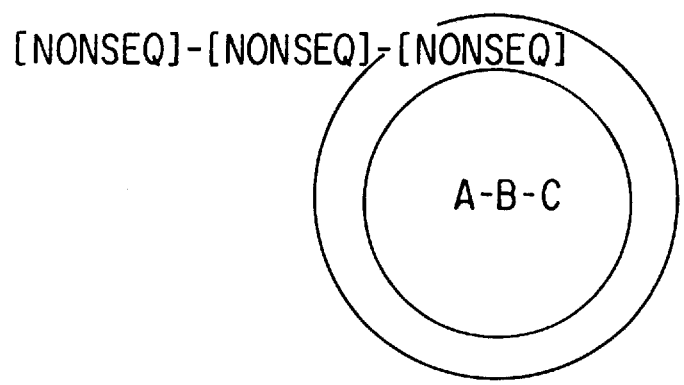

FIGS. 1A–1C. Strategies for attaching encoded libraries of synthetic test compound. Subunits of the synthetic test compound are indicated as [NONSEQ]; the coding molecule is indicated by A-B-C. (A) The test compound and coding molecule can be attached separately to the support directly or via a linker, in a statistical distribution that can be altered based on mass action and inherent reactivity. (B) The synthetic test compound and the coding molecule can be attached to the same linker on the separate phase support, in a defined molar ratio. (C) The synthetic test compound is attached on the surface and the coding molecule is attached in the interior of a separate phase support, such as a resin bead. Alternatively, in (C), the coding molecule can be on the surface and the test compound in the interior.

Figure 2A:
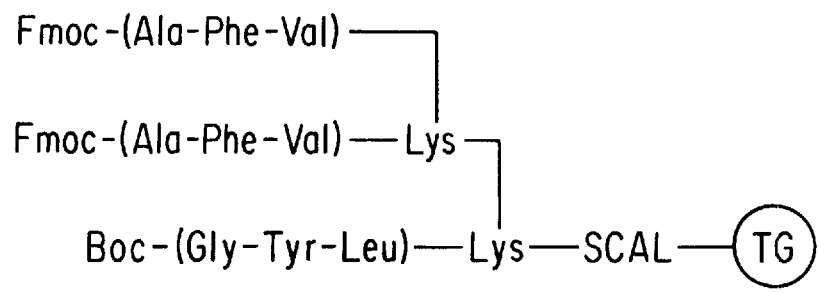
Figure 2B:
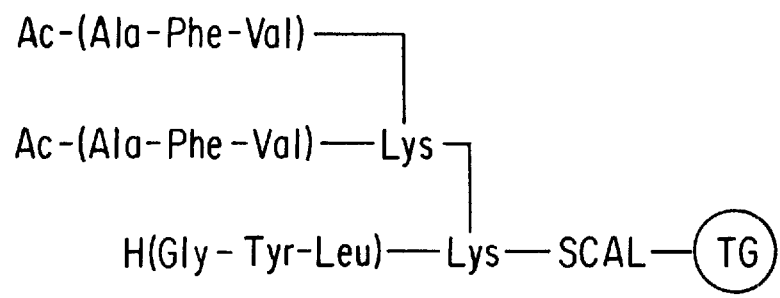
Figure 2C:
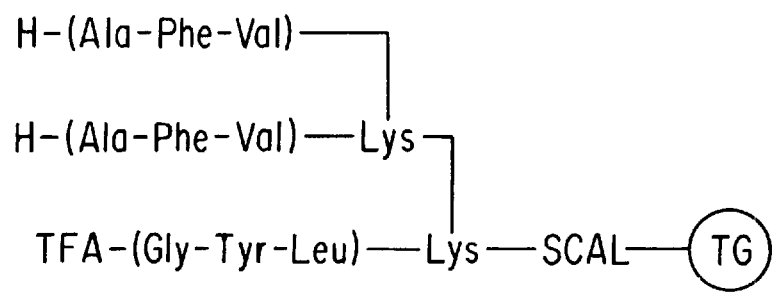

FIGS. 2A–2C. Three forms of a model encoded library in which the "test" compound (Ala-Phe-Val) and the coding molecule (Gly-Tyr-Leu) are both peptides. (A) The "test" compound was synthesized using the Fmoc protecting group, and the coding molecule was sythesized with the Boc protecting group. Fmoc and Boc are orthogonal protecting groups. (B) The Fmoc deprotected "test" compound was acetylated so that only the coding peptide would be sequenced by Edman degradation. (C) The coding peptide was blocked with trifluoroacetyl (TFA), allowing Edman sequencing of the "test" compound, followed by removal of TFA and sequencing of the coding peptide. The peptides were attached to the TentaGel (TG) resin via a safety-catch amide linker (SCAL; Patek and Lebl, 1991, Tetrahedron Lett. 32: 3891–3894) with lysine branches.

Figure 3:
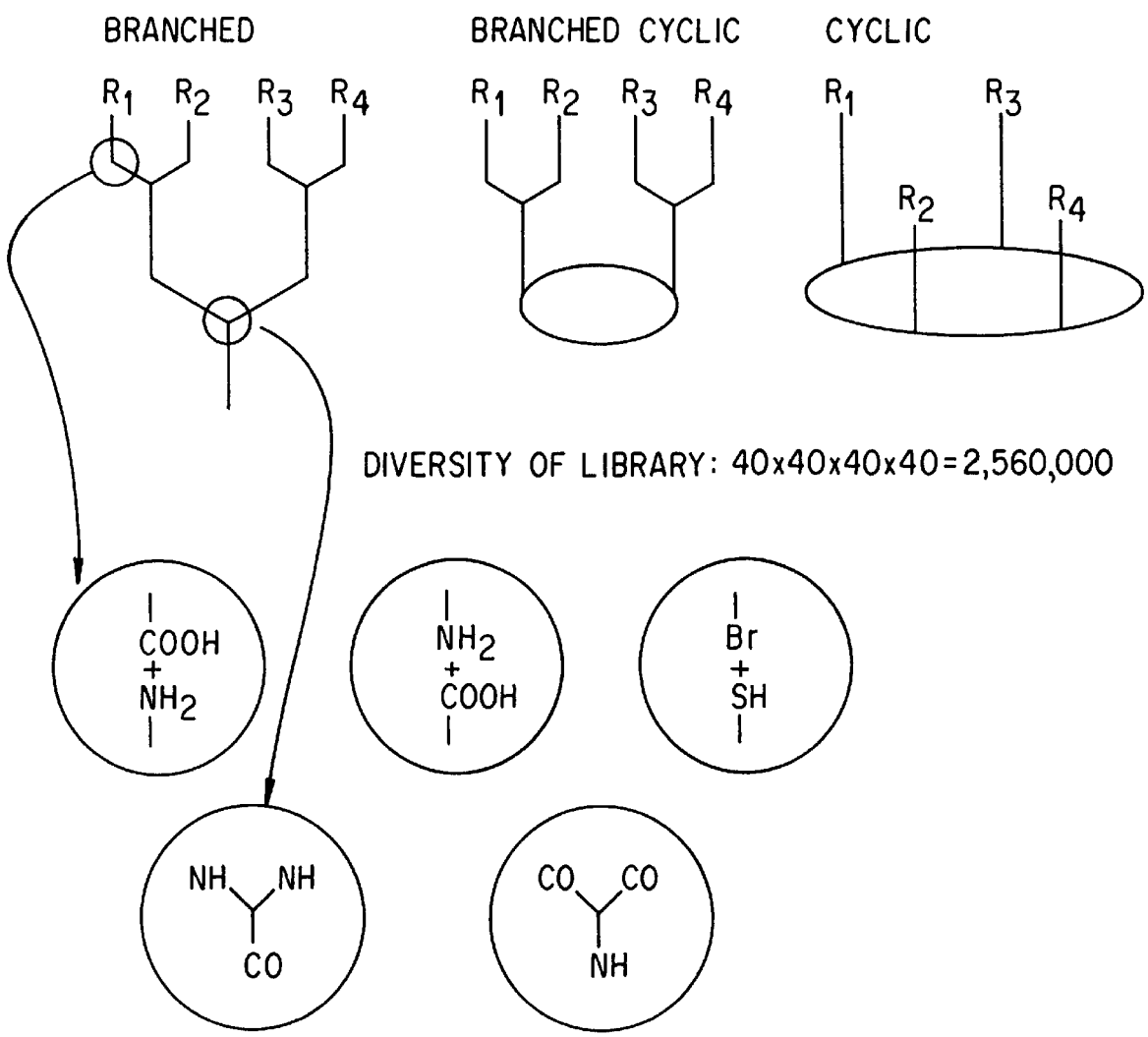

FIGS. 3. Model branched scaffold libraries, showing various possible linking chemistries, including reaction of an amine with a carboxylic acid to form an amide; reaction of a carboxylic acid with an amine to form an amide; reaction of a thiol with a alkylhalogenid to form a sulfide.

Figure 4A:
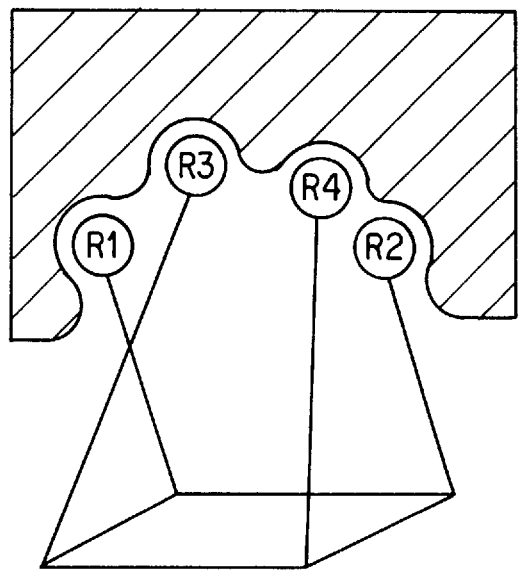
Figure 4B:
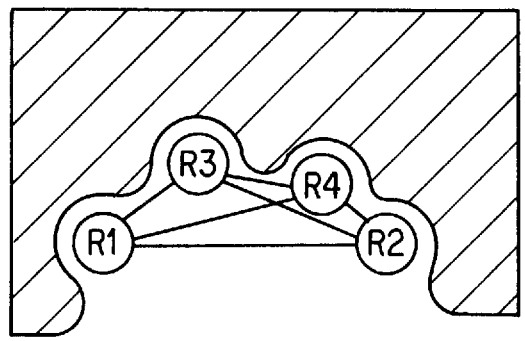

FIGS. 4A and 4B. A model of interaction of a scaffold synthetic test compound with an acceptor molecule. (A) The functional groups attached to the scaffold are free to assume an appropriate binding conformation. (B) The functional groups on the scaffold are constrained in the appropriate binding conformation.

Figure 5:
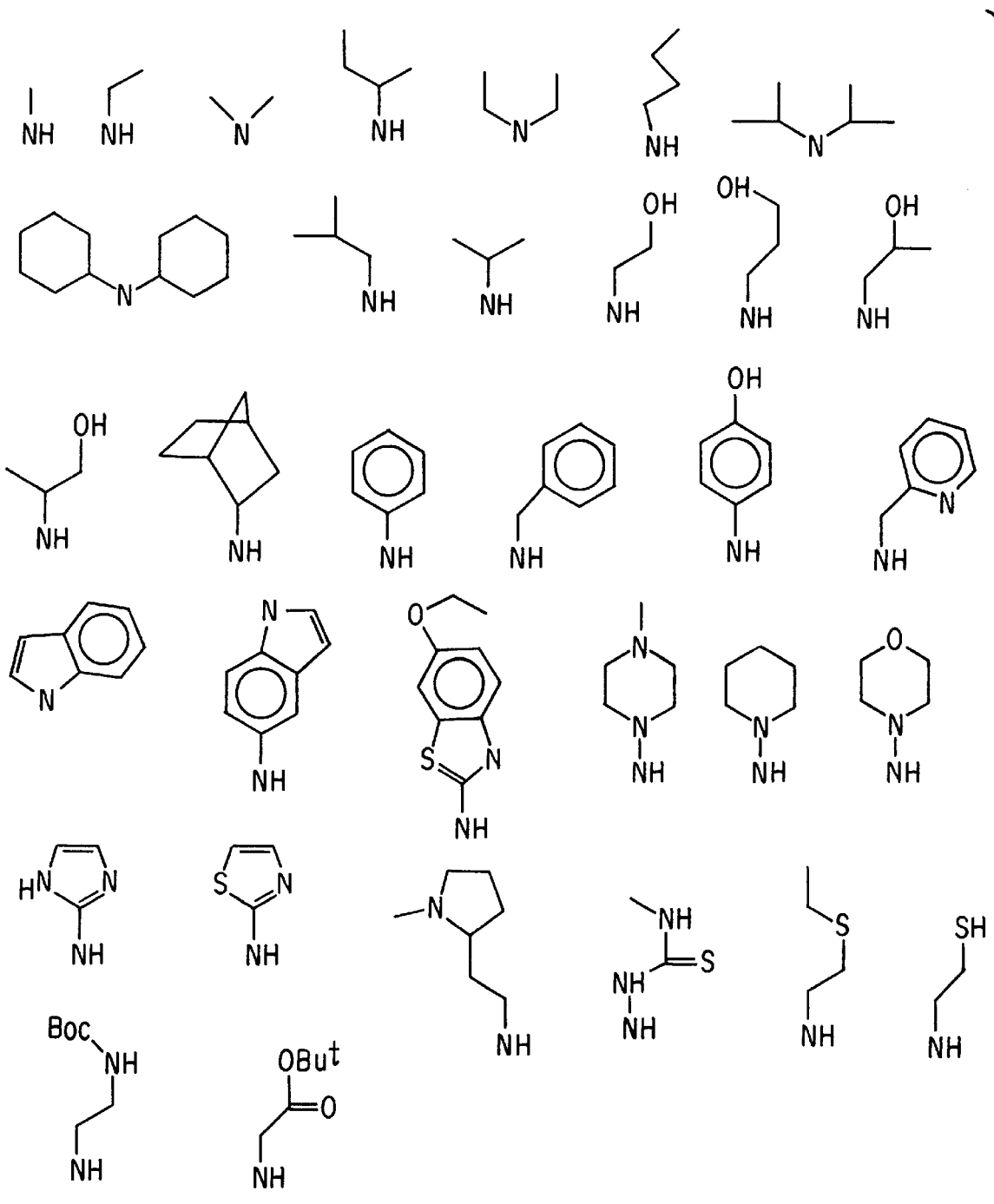

FIG. 5. Structures of some of the subunits that can be chemically linked in random structures to form the libraries of synthetic test compound.

Figure 6:
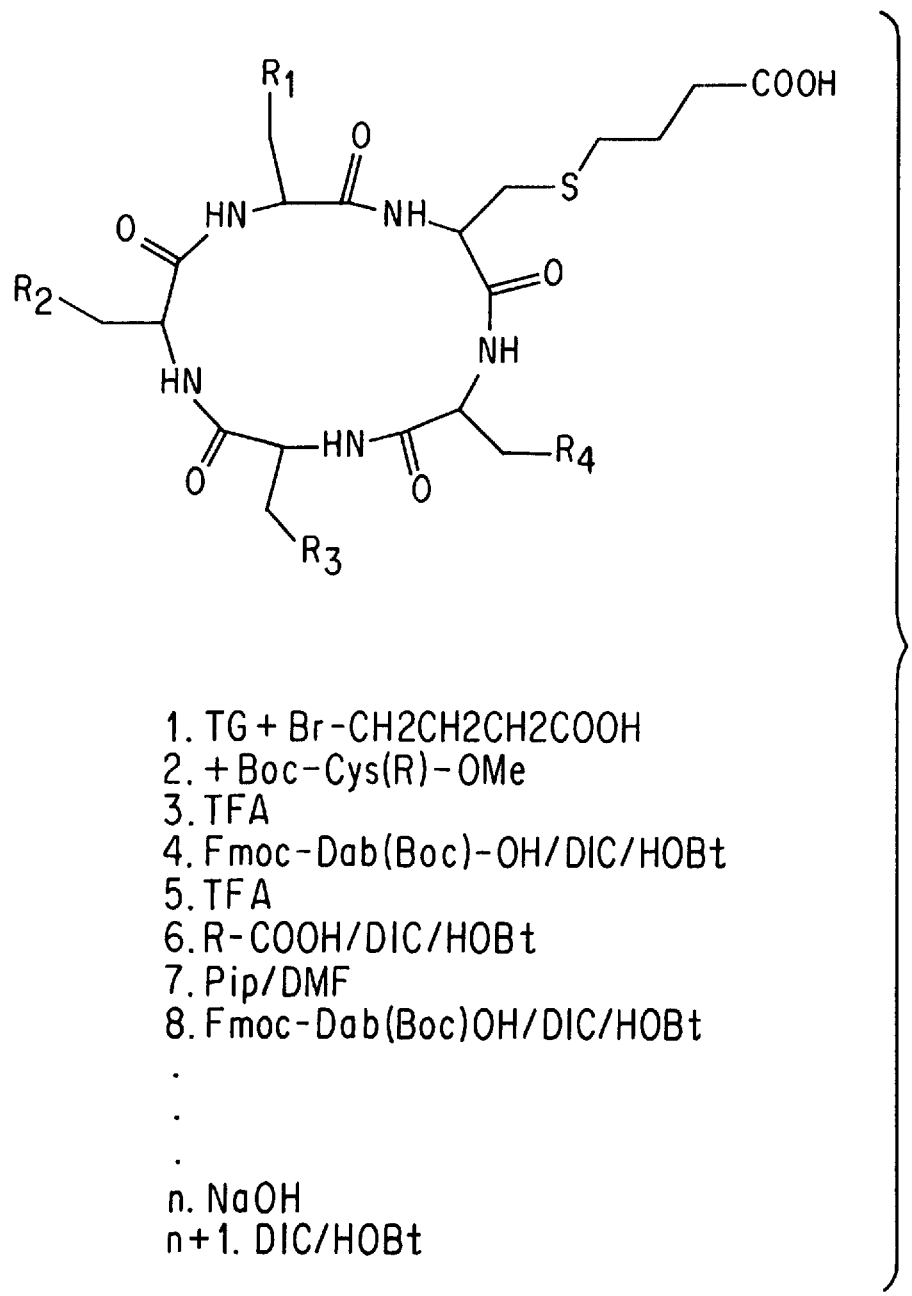

FIG. 6. A model cyclic library formed from repeated condensation reactions with Boc and Fmoc blocked subunits.

Figure 7:
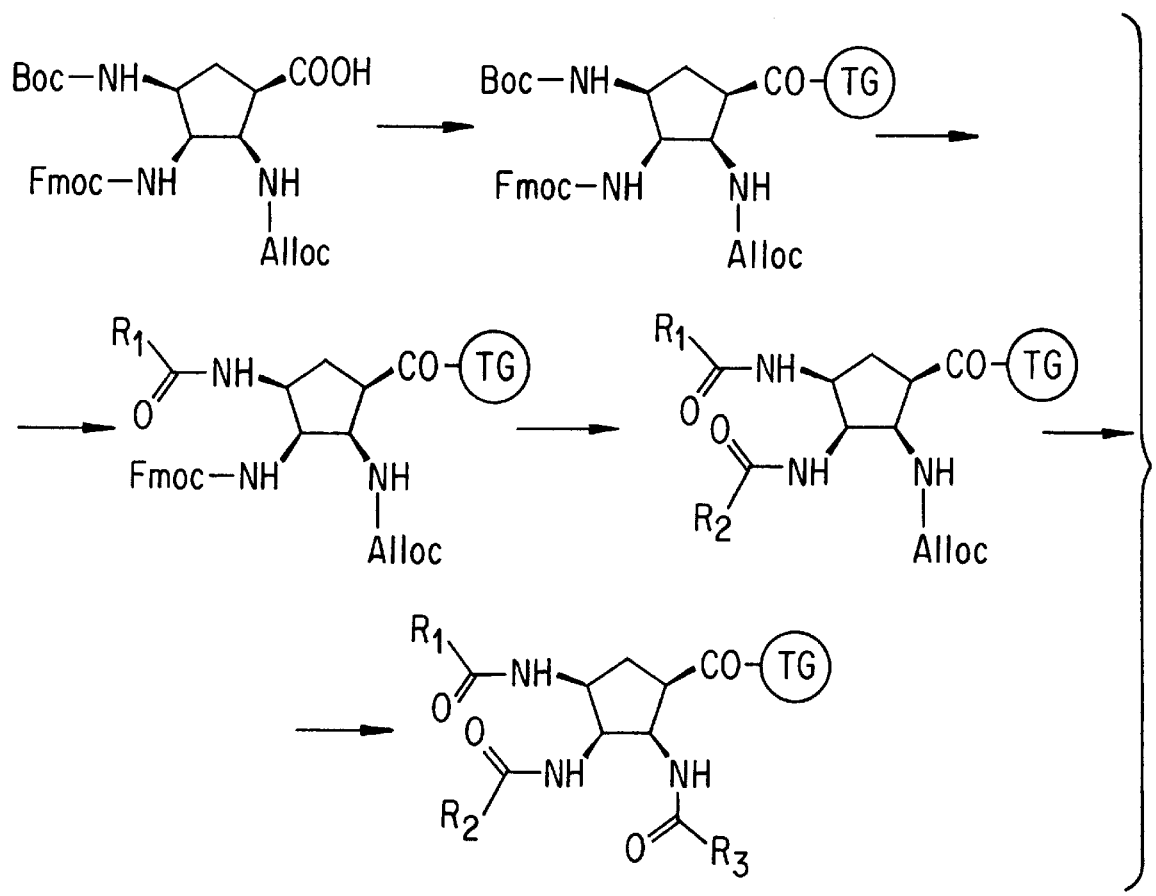

FIG. 7. A scheme for preparation of a scaffold library on TentaGel resin in which the scaffold is cyclopentane.

Figure 8:
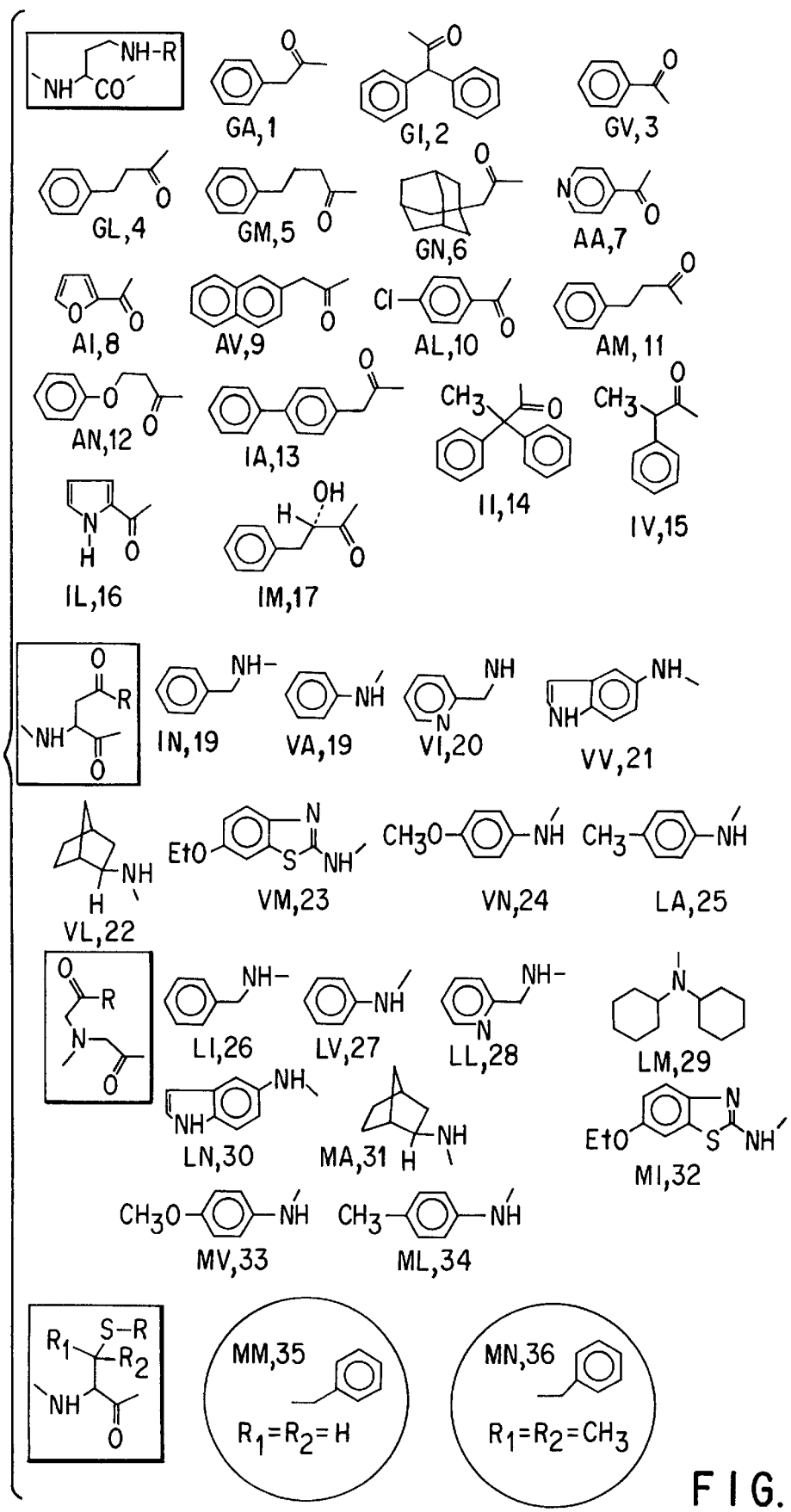

FIG. 8. Structures of subunits used to prepare a scaffold library of the invention. The two-letter amino acid dipeptide code for each of the subunits is shown below each one. Preparation and use of this library is described in Section 9, infra.

5. DETAILED DESCRIPTION OF THE INVENTION

The invention relates to libraries of synthetic test compound attached to separate phase supports, in which each separate phase support contains a single species of synthetic test compound, and methods of synthesis and use of such libraries. The term "separate phase support" refers to a matrix to which the synthetic test compound can be attached, which matrix is not soluble in a liquid or forms a two phase system with a liquid. Preferably, the separate phase is a solid phase, although separate phases such as hydrogels and aerogels are also contemplated.

As used herein, the term "library of synthetic test compound" refers to collections of synthetic test compound on separate phase support particles in which each separate phase support particle contains a single structural species of the synthetic test compound. Each support contains many copies of the single structural species. For example, a typical resin support for solid phase peptide synthesis contains about 50–250 pmol of peptide. The structures of the synthetic test compound are derived from a substantially random chemical combination of "subunits".

As used herein, the term "synthetic test compound" refers to small molecules consisting of 2 to 100, and more preferably, 2–20, subunits, with or without a scaffold. In one embodiment, the synthetic test compound is a polymer formed of subunits linked via such linkages as amide, urea, ester, ether, carbamate, amine, sulfide, disulfide, carbon-carbon, such as alkane, alkene and alkyne, and the like; in particular, the compound can include, but is not limited to, polycarbamate, polyurea, polyamide, polyester, polyether, etc., or any combination thereof, as described in detail infra. In another embodiment, a synthetic test compound may be a randomly functionalized molecular scaffold, such as, but not limited to, a steroid, heterocyclic structure, a polyaromatic ring, or carbohydrate structure, and the like, as described in detail infra.

As used herein, the term "subunit" refers to a chemical subcomponent, whereby the synthetic test compound is formed by linkage of the chemical subcomponents by a defined chemistry. For example, a "library of peptides" is a collection of peptides (the synthetic test compound), i.e., chains consisting of 2–100 α-amino acid residues (the subunits), whose sequences contain any amino acid residue preceding or following any other amino acid residue. An example of a "library of steroid derivatives" is a collection of steroid derivatives containing any one of a set of functional groups, the subunits, at specific positions of the steroid nucleus.

More preferably, the present invention relates to encoded libraries of synthetic test compound. As used herein, the term "encoded library" refers to a library in which each distinct species of compound is paired on each separate phase support with a coding molecule whose structure is readily determinable and encodes a unique structure for its pair partner in the library. In a preferred embodiment of an encoded molecular library, the coding polymeric molecule is a peptide. In another embodiment, the coding polymeric molecule is an oligonucleotide.

Examples of embodiments of libraries include, but are not limited to, the following:

libraries in which the synthetic test compound are polyamides, i.e., the synthetic test compound are chains of 2–100 amino acids linked through amide bonds;

libraries in which the synthetic test compound are polyesters, i.e., chains of 2–100 hydroxy acids linked by ester bonds;

libraries in which the synthetic test compound are polyethers, i.e., chains of 2–100 hydroxy alcohols linked by ether bonds;

libraries in which the synthetic test compound are polyureas;

libraries in which the synthetic test compound are polyurethanes;

libraries in which the synthetic test compound are polycarbonates;

libraries in which the synthetic test compound are polyamines;

libraries in which the synthetic test compound are polyalkanes, polyalkenes, or polyalcohols, including halo derivatives thereof;

libraries in which the synthetic test compound are polysulfides;

libraries in which the synthetic test compound are polydisulfides;

libraries in which the synthetic test compound are polymers whose structures contain randomly arranged segments from two or more of the polymeric structures described in the embodiments above;

libraries in which the synthetic test compound are derivatives of a steroid structure;

libraries in which the synthetic test compound are derivatives of a sugar such as β-D-glucose;

libraries in which the synthetic test compound are derivatives of a heterocyclic structure, such as benzodiazepine;

libraries in which the synthetic test compound are derivatives of a structure capable of serving a scaffolding onto which multiplicity of structures such as but not limited to carboxylic acids, amines, and halogen derivatives can be attached in a defined way;

libraries in which the molecules are chimeric structures containing one or more sequences of variable length linked by chemistry selected from one or more of the following: amides, esters, ethers, carbonates, sulfides, disulfides, alkenes, and amines, and one or more structures capable of acting as a scaffolding, such as a steroid, a sugar, an aromatic or polyaromatic structure.

Many different subunits for the different classes of synthetic test compound are commercially available from suppliers such as Sigma, Aldrich, ICI Chemicals, etc. Alternatively, subunits can be prepared synthetically using standard chemical synthesis techniques.

In a preferred embodiment, the libraries listed above are encoded libraries in which each separate phase support contains a synthetic test compound and a polymeric sequence encoding the structure of the synthetic test compound. Preferably, the coding polymeric sequence is a peptide.

5.1 Coding Strategies

As noted above, in a preferred aspect the libraries of the invention are encoded libraries in which the sequence of a coding molecule on each support corresponds to the structure of the synthetic test compound on each support. Thus, each unique synthetic test compound structure is encoded by a unique coding molecule sequence. As noted supra, preferably the coding molecule is a peptide, although the present invention encompasses the use of nucleic acids or any sequenceable polymer as a coding sequence.

The paradigm of a coding sequence is the genetic code, in which triplet nucleotide sequences in a gene corresponds to a specific amino acid in a protein encoded by the gene. The arrangement of codons in a gene corresponds to the sequence of amino acids in a protein. Thus, the gene encodes the protein.

Following this analogy, coding of the sequence of a library of synthetic test compound, such as a polyamide whose sequence cannot be established by traditional methods (e.g., Edman degradation), with a coding molecule can be accomplished readily using an analogous code. The choice of the code is purely arbitrary, including whether single, double or triple (or greater) combinations of subunits of the coding molecule correspond to each subunit of the synthetic test compound.

For example, the coding molecule may be a peptide. In this case codes consisting of one or more amino acid residues which can be readily detected by Edman degradation, and are also known to couple efficiently in solid phase peptide synthesis without requiring side-chain protection, are considered to be especially useful. For example, if a triplet code based on the amino acids leucine (Leu), glycine (Gly), alanine (Ala), and phenylalanine (Phe) (all of which do not require side chain protection and couple efficiently during peptide synthesis and are furthermore readily detectable by Edman degradation) is used, libraries of synthetic test compound containing up to sixty-four structurally different subunits, with each subunit paired with a unique peptide containing triplets of Leu, Gly, Ala, or Phe (each triplet corresponding to one and only one subunit in the polyamide), may be synthesized using suitable chemical reactions. Other preferred amino acids, i.e., those that do not require side chain protection, include but are not limited to isoleucine, valine, cyclohexyl-L-alanine, norleucine, norvaline, proline, and the like. Less preferred are asparagine and glutamine. In another embodiment, each of the 20 natural amino acids can code for a specific subunit. A single coding sequence subunit or codon can code for more than one subunit of the synthetic test compound, resulting in a degenerate code, although this is not necessary.

The present invention provides various strategies to increase the probability that screening assays recognize active synthetic test compound instead of the coding molecules on a given support, which are discussed in Section 5.3., infra.

5.2 Methods for Generating a Library of Synthetic Test Compound

As stated above, the present invention relates to a method of generating a library of synthetic test compound on separate phase supports. Preferably the library is one in which each synthetic test compound is paired with a unique coding molecule, e.g., a peptide, whose sequence encodes the structure of the synthetic test compound attached to the same support and can be readily determined using traditional analytical techniques, e.g., Edman degradation.

If the synthetic test compound are functionalized molecular scaffolds, the scaffold or a precursor to the scaffold will be attached to the solid phase support prior to initiation of synthesis.

The synthesis of libraries of synthetic test compound comprises repeating the following steps:

(i) dividing the selected support into a number of portions which is at least equal to the number of different subunits to be linked;

(ii) chemically linking one and only one of the subunits of the synthetic test compound with one and only one of the portions of the solid support from step (i), preferably making certain that the chemical link-forming reaction is driven to completion to the fullest extent possible;

(iii) thoroughly mixing the solid support portions containing the growing synthetic test compound;

(iv) repeating steps (i) through (iii) a number of times equal to the number of subunits in each of the synthetic test compound of the desired library, thus growing the synthetic test compound;

(v) removing any protecting groups that were used during the assembly of the synthetic test compound on the solid support.

Preferably, a coding molecule is synthesized in parallel with the synthetic test compound. In this instance, before or after linking the subunit of the synthetic test compound to the support in step (ii), one or more subunits of the coding molecule, that correspond(s) to the added subunit of the synthetic test compound, is linked to the growing coding molecule such that a unique structural code (see Section 5.1, supra), corresponding to the structure of the growing synthetic test compound, is created on each support. It can be readily appreciated that if an encoded library is prepared, synthesis of the coding subunit or subunits must precede the mixing step, (iii).

The repetition of steps (i)–(iii) (see step (iv)) will naturally result in growing the synthetic test compound and, if the process is modified to include synthesis of a coding molecule, the coding molecule in parallel with the test compound. The test arm and coding arm are used herein to refer to the synthetic test compound synthesized on the support, and, if present, the coding molecule synthesized on the support, respectively.

The present invention encompasses modification of any of the steps of the above procedure. For example, a different, and occasionally desirable, library will result if step (ii) is changed to involve linking of the same polymer subunit to all of the portions of the solid support. In this case, elongation of the coding polymer needs to be modified analogously.

In another embodiment, if the same polymer is elongated on the test arm as on the coding arm, the coding arm need not be elongated past the point required to encode a non-sequencable subunit of the synthetic test compound, as long as the history of the synthesis is known, e.g., the number of subunits is known.

In another embodiment of the invention, the solid support used to carry out the synthesis of a synthetic test compound which is a short polymer is derivatized with one or more of the subunits of the polymer prior to its use in the synthesis of a library.

In one embodiment, enough support particles are used so that there is a high probability that every possible structure of the synthetic test compound is present in the library. Such a library is referred to as a "complete" library. To ensure a high probability of representation of every structure requires use of a number of supports in excess, e.g., by five-fold, twenty-fold, etc., according to statistics, such as Poisson statistics, of the number of possible species of compounds. In another embodiment, especially where the number of possible structures exceeds the number of supports, not every possible structure is represented in the library. Such "incomplete" libraries are also very useful.

In a further embodiment, a library can have synthetic test compound whose structures include a desirable polymeric sequence, found as a result of screening another library added prior to generation of the library or at the end of generation of the library. Such a library is prepared by synthesizing a solid support containing the desirable polymeric sequence and using this derivatized support as the solid support for the synthesis of the new library. Alternatively, a portion of the library synthetic test compound can be synthesized followed by synthesis of the desirable polymer sequence as an extension of the test compounds on all of the separate phase supports. Alternatively, the desirable sequence may be discontinuous and included within the random library.

5.3 Development and Use of Separate Phase Synthesis Supports and Linkers in Encoded Molecular Library Syntheses 5.3.1 Supports and Linkers Useful in Encoded Molecular Library Synthesis A separate phase support suitable for use in the present invention is characterized by the following properties: (1) insolubility in liquid phases used for synthesis or screening; (2) capable of mobility in three dimensions independent of all other supports; (3) containing many copies of each of the synthetic test compound and, if present, the coding sequence attached to the support; (4) compatibility with screening assay conditions; and (5) being inert to the reaction conditions for synthesis of a test compound and for coding molecule synthesis. A preferred support also has reactive functional groups, such as hydroxyl, carboxyl, amino, thiol, etc., for attaching a subunit which is a precursor to each of the synthetic test compound and coding molecules, or for attaching a linker which contains one or more reactive groups for the attachment of the monomer or other subunit precursor.

As used herein, separate phase support is not limited to a specific type of support. Rather a large number of supports are available and are known to one of ordinary skill in the art. In a preferred aspect, the separate phase support is a solid phase support, although the present invention encompasses the use of semi-solids, such as aerogels and hydrogels. Solid phase supports include silica gels, resins, derivatized plastic films, glass beads, cotton, plastic beads, alumina gels, polysaccharides such as Sepharose and the like, etc. A suitable solid phase support may be selected on the basis of desired end use and suitability for various synthetic protocols. For example, in polyamide synthesis, useful solid phase support may be resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethyl-acrylamide resin (obtained from Milligen/Biosearch, California). In a preferred embodiment for peptide and other polyamide syntheses, the preferred solid phase support is polydimethyl-acrylamide resin. Preferred solid phase synthesis supports for specific syntheses are described below. For example, in a model specific embodiment, infra, a support such as is used in Merrifield peptide synthesis can be sequentially derivatized by an Fmoc-protected amino acid, which through subsequent synthetic cycles is extended to give the polyamide "synthetic test compound", and a Ddz- or Boc-protected amino acid, which is extended to give the coding peptide. Other sequential derivatizations are described below. Thus, each resin bead is functionalized to contain both synthetic test compound and the corresponding coding structures, the relative amounts of which depend on the reaction conditions for attaching the first Fmoc- and Ddz- (or Boc-) protected amino acids. In a variation of this approach, the synthetic test compound and coding molecules are attached to the solid support through linkers such as those described below.

The supports of the invention may also comprise linkers or an arrangement of linkers. As used herein, a linker refers to any molecule containing a chain of atoms, e.g., carbon, nitrogen, oxygen, etc., that serves to link the molecules to be synthesized on the support with the support. The linker is usually attached to the support via a covalent bond, before synthesis on the support starts, and provides one or more sites for attachment of precursors of the molecules to be synthesized on the support. Various linkers can be used to attach the precursors of molecules to be synthesized to the solid phase support. Examples of linkers include aminobutyric acid, aminocaproic acid, 7-aminoheptanoic acid, 8-aminocaprylic acid, lysine, iminodiacetic acid, polyoxyethylene, glutamic acid, etc. In a further embodiment, linkers can additionally comprise one or more β-alanines or other amino acids as spacers.

In another embodiment, the "safety-catch amide linker" (SCAL) (see Patek, M. and Lebl, M. 1991, Tetrahedron Letters 32: 3891–3894; International Patent Publication WO 92/18144, published Oct. 29, 1992) is introduced to the support.

In addition to the linkers described above, selectively cleavable linkers may be employed, preferably for attachment of the synthetic test compound molecule. One example is the ultraviolet light sensitive linker, ONb, described by Barany and Albericio (1985, J. Am. Chem. Soc. 107: 4936–4942). Other examples of photocleavable linkers are found in Wang (1976, J.Org. Chem. 41: 32–58), Hammer et al. (1990, Int. J. Pept. Protein Res. 36: 31–45), and Kreib-Cordonier et al. (1990, in "Peptides—Chemistry, Structure and Biology", Rivier and Marshall, eds., pp. 895–897). Landen (1977, Methods Enzym. 47: 145–149) used aqueous formic acid to cleave Asp-Pro bonds; this approach has been used to characterize T-cell determinants in conjunction with the Geysen pin synthesis method (Van der Zee et al., 1989, Eur.J.Immunol. 191: 43–47). Other potential linkers cleavable under basic conditions include those based on p-(hydroxymethyl)benzoic acid (Atherton et al., 1981, J. Chem. Soc. Perkin I: 538–546) and hydroxyacetic acid (Baleaux et al., 1986, Int. J. Pept. Protein Res. 28: 22–28). Geysen et al. (1990, J. Immunol. Methods 134: 23–33; International Publication WO 90/09395, published on Aug. 23, 1990) reported peptide cleavage by a diketopiperazine mechanism. Preferred diketopiperazine linkages are disclosed in U.S. patent application Ser. No. 07/919,454, filed Jul. 24, 1992, which is hereby incorporated by reference in its entirety. Enzyme-cleavable linkers may also be useful. An enzyme may specifically cleave a linker that comprises a sequence that is recognized by the enzyme. Thus, linkers containing suitable peptide sequences may be cleaved by a protease and linkers containing suitable nucleotide sequences may be cleaved by an endonuclease. In certain instances, one may derivatize a portion (e.g., 10–90%) of the available resin functional groups with a cleavable linker using certain reaction conditions, and the remaining of the resin functional groups with a linker which is stable to the cleavage conditions to ensure that enough material will remain on the resin after cleavage for further study. This arrangement is particularly preferred when there is no coding molecule. Combinations of linkers cleavable under different reaction conditions can also be used to allow selective cleavage of molecules from a single solid support bead.

Preferably, a cleavable linker can be used to release the synthetic test compound, or a portion thereof, for testing in a screening assay. In this instance the coding sequence, if present, is attached to the solid phase support via a non-cleavable linker.

An approach for the synthesis of encoded libraries involves linking the precursors of the synthetic test compound and coding molecules of the library together via a branched linker which also serves to link both precursors to the solid support. Depending on the structure of the linker, either molecule or both may be detached from the solid support for further study. One example of this approach of anchoring synthetic test compound and coding molecules is to use Lys(SCAL) derivatized TentaGel.

A solid phase support linker for use in the present invention may further comprise a molecule of interest, which can be further derivatized to give a molecular library. The pre-attached molecule may be selected according to the methods described herein, or may comprise a structure known to embody desired properties.

The present invention encompasses the use of an array of linkers attached to the solid support in one of many arrangements. For example, a lysine carboxyl group can be linked to a SCAL linker that is linked to the solid phase support, thus producing a support functionalized with a lysine-SCAL linker. In another embodiment, a lysine can be linked to the solid phase support via a polyethylene glycol linker. A SCAL linker on a solid support can also be linked to an amino group of a diamine linker, while the other amino group can be used directly for further coupling. In yet another embodiment, a cleavable linker can be attached to one of the amino groups of a lysine linked to a support while the other amino group is used without further modification. Specific couplings to each amino group of a lysine linker can be accomplished by using orthogonal protecting groups.

In a specific embodiment, infra, SCAL linked to TentaGel can be acylated with lysine whose amino groups are protected with Fmoc and Boc; the resulting support is TentaGel with the linker Boc-Lys(Fmoc)-SCAL which can be deprotected sequentially to provide two unique amino groups which, e.g., upon acylations by two different sets of amino acids, can become anchors for two polyamides. Acylation of one of the amino groups of the lysine moiety of the linker with Boc-Lys(Fmoc) provides a new linker with a total of three potential amino anchors (upon sequential deprotection), and acylation of both amino groups of the linker lysine by Boc-Lys(Fmoc) provides a new linker with a total of four potential amino anchors.

5.3.2 Topology of Anchoring of Synthetic Test Compounds and Coding Molecules on Solid Support Surfaces A variety of approaches for topologically separating the synthetic test compound and coding molecules on a solid support in order to generate libraries are contemplated.

Topologically separating the synthetic test compound and the coding molecule refers to the separation in space for a support. For example, if the support is a resin bead, separation can be between the surface and the interior of the resin bead of a significant number of the ligand-candidate molecules from a significant number of the coding molecules. Preferably, the surface of the support contains primarily synthetic test compound molecules and very few coding molecules. More preferably, the surface of the support contains greater than 90% synthetic test compound. Even more preferably, the surface of the support contains greater than 99% synthetic test compound molecules; most preferably, it contains more than 99.9% synthetic test compound. The advantage of such an arrangement is that it limits interference of the coding molecule in a binding screening assay (see Section 5.6, infra). It is not necessary that the topological area that contains the coding sequence, i.e., the interior of a resin bead, be free of the synthetic test compound.

In the foregoing example, the coding molecule is segregated in the interior of the support particle. It is also contemplated that the coding molecule may be segregated to the surface of a support particle, or to one side of a support particle.

One general approach for the topological separation of synthetic test compound from coding molecules involves the selective derivatization of reactive sites on the support based on the differential accessibility of the coupling sites to reagents and solvents. For example, regions of low accessibility in a resin bead are the interior of the bead, e.g., various channels and other cavities. The surface of a resin bead, which is in contact with the molecules of the solution in which the bead is suspended, is a region of relatively high accessibility. Methods for effecting the selective linkage of coding and synthetic test compound precursors to a suitable solid phase support include, but are not limited to, the following.

(i) Selective derivatization of solid support surfaces via controlled photolysis: Two approaches can be used. In one, a functionalized solid support is protected with a photocleavable protecting group, e.g., nitroveratryloxycarbonyl (Nvoc) (Patchornik et al., 1970, J. Am. Chem. Soc. 92: 6333). The Nvoc-derivatized support particles are arranged in a monolayer formation on a suitable surface. The monolayer is photolyzed using light of controlled intensity so that the area of the bead most likely to be deprotected by light will be the area of the bead in most direct contact with the light, i.e., the exterior surface of the bead. The resulting partially deprotected beads are washed thoroughly and reacted with a precursor of the synthetic test compound containing a light-stable protecting group. For example, in the case of synthesis of an encoded library of polyamides, this precursor might be a Boc-protected amino acid, which through further synthetic cycles is converted to the polyamide synthetic test compound. Following the reaction with the synthetic test compound precursor, the beads are subjected to quantitative photolysis to remove the remaining light-sensitive protecting groups, thus exposing functional groups in less light-accessible environments, e.g., the interior of a resin bead. After this quantitative photolysis, the support particles are further derivatized with an orthogonally-protected precursor of the coding molecule, e.g., Fmoc-protected amino acid. The resulting solid support bead will ultimately contain synthetic test compound segregated primarily on the exterior surface and coding molecules located in the interior of the solid phase support bead.

An alternative photolytic technique for segregating coding and synthetic test compound molecules on a support involves derivatizing the support with a branched linker, one branch of which is photocleavable, and attaching the precursor of the coding molecule to the photosensitive branch of the linker. After completion of the synthesis, the support beads are arranged in a monolayer formation and photolyzed as described above. This photolysis provides beads which contain patches of synthetic test compound molecules for selective screening with minimal interference from the coding molecules.

(ii) Selective derivatization of solid support surfaces using chemical or biochemical approaches. The efficacy of these chemical and biochemical derivatizations depends on the ability of exterior surface functional groups, which are exposed, to react faster than other groups in the interior which are not exposed. It has been observed, for example, that antibodies cannot bind to peptide ligands in the interior of a resin solid phase support. Therefore, using differences in steric hindrance imposed by the structure of the support or by modulating the swelling of a bead through choice of reaction solvent, reactive groups on the exterior of the bead that are accessible to macromolecules or certain reagents can be reacted selectively with respect to reactive groups in the interior of the bead. Therefore, the reactive groups in the exterior of the bead can be modified for the synthesis of the synthetic test compound, while interior reactive groups can be modified for extension of the coding molecules, or both the coding molecules and synthetic test compound. Since the number of reactive groups inside a resin bead is much larger than the number of groups on the outer surface, the actual number of coding molecules will be very large, providing enough coding molecules for accurate sequence analysis, and thus the decoding of the structure of the synthetic test compound. A variety of chemical and biochemical approaches are contemplated including the following:

(a) Use of polymeric deprotecting agents to selectively deprotect parts of the exterior of a solid support bead carrying protected functional groups. The deprotected functional groups are used as anchors for the synthetic test compound. The functional groups which remain protected are subsequently deprotected using a nonpolymeric deprotecting agent and used as anchors for the attachment of the coding molecules. In a specific embodiment, this method involves use of enzymes to selectively activate groups located on the exterior of beads which have been derivatized with a suitable enzyme substrate. Due to their size, enzymes are excluded from the interior of the bead. In an example, infra, an enzyme completely removes a substrate from the surface of a resin bead, without significantly affecting the total amount of substrate attached to the bead, i.e., the interior of the bead. The removal of substrate exposes, and thus activates, a reactive site on the bead. The enzyme-modified groups of the solid support are used to anchor the synthetic test compound and those groups that escaped modification are used to anchor the majority of the coding molecules.

(b) Use of a polymeric protecting group to selectively block exposed unprotected functional groups on the exterior of a support bead. The unprotected functional groups in the interior of the support are used to anchor the coding molecule. The remaining protected functional groups are then deprotected and used as anchors for the synthetic test compound of the library. In a specific example, infra, the polymer polyglutamic acid of 30 kd MW completely blocks surface accessible functional groups without affecting the total amount of peptide attached to the bead. If the polymer used for the blocking is attached via its α-carboxyl group, then a single-step Edman degradation performed after deprotection of the x-amino group of the polymer can regenerate the surface amino groups.

(c) Creating a different state in the interior of the bead, e.g., by freezing water inside the beads, then reacting the beads in an organic solvent at low temperature to keep the water frozen. Thus the surface of the bead, but not the inside, can be specifically reacted.

5.4 Strategy for Carrying Out Alternating Syntheses of the Coding and Synthetic Test Compounds Molecules During the Generation of Encoded Libraries An important synthetic operation during the synthesis of an encoded library involves the use of orthogonal protecting groups. For the efficient synthesis of the coding molecules in parallel with the synthesis of the synthetic test compound of the library on the same solid support particle, the protecting groups used for each synthesis must be orthogonal, i.e., during all synthetic operations on one molecule the protecting groups on the other molecule must remain intact.

Several orthogonal combinations of protecting groups for the assembly of the synthetic test compound and coding molecules of a molecular library can be used. Useful protecting groups are described in Geiger and Konig, 1981, "The Peptides" (Gross and Meinhofer, eds.) pp. 3–101, Academic Press: New York). A very useful combination involves base- and acid-cleavable protecting groups. For example, for the synthesis of an encoded library of polyamides, the base-sensitive $N^\alpha$-[(9-fluorenylmethyl)oxy] carbonyl (Fmoc-) protecting group may be used to assemble the synthetic test compound molecules, and the acid-labile $N^\alpha$-[[2-(3,5-dimethoxyphenyl)prop-2-yl]oxy]carbonyl (Ddz) protecting group may be used to assemble the oding peptide molecules. Fmoc protecting groups and heir use in peptide synthesis have been described by Carpino and Han (1972, J. Org. Chem. 37: 3403–3409) and Ddz protecting groups have been described by Voss and Birr (*Hoppe-Seyler's Z. Physiol. Chem.* 1981, 362, 717–725). Both types of protecting groups have traditionally been used to block the α-amino groups of α-amino acids during peptide synthesis; however, other suitable amino groups may be protected by these groups during the synthesis of a polyamide. If the polyamides of interest contain side-chains with reactive functional groups, protection of the reactive groups as t-butoxycarbonyl (Boc) and t-butyl (t-Bu) derivatives, or preferably, as the more acid-stable derivatives benzyl and benzyloxycarbonyl, may be useful. If the reactive side-chain groups are protected using t-butyl-type groups, the coding peptide may be synthesized using a protecting group which is more acid-labile than Ddz, such as Nps (Zervas et al., 1963, J. Am. Chem. Soc. 85: 3660) or Trt (Zervas et al., 1956, J. Am. Chem. Soc. 78: 1359)

An alternative combination of orthogonal protecting groups in the synthesis of an encoded library of polyamides involves use of Fmoc or other base-labile groups to assemble the coding peptides and Ddz or other acid-labile groups to assemble the ligand binding candidates.

An alternative orthogonal combination of protecting groups for the alternating and parallel synthesis of coding molecules and synthetic test compound involves trichloroethoxycarbonyl as an amine protecting group and trichloroethyl as a hydroxyl protecting group, which can be removed using a reducing agent such as zinc in acetic acid, for the synthesis of, e.g., polyesters in an encoded library of polyesters, and Boc and t-Bu or other acid-cleavable group for the synthesis of the coding peptides. As before, the two sets of orthogonal protecting groups may be interchangeable, i.e., $N^\alpha$-trichloroethoxycarbonyl-protected amino acids are used to prepare the coding peptides and $N^\alpha$-Boc-protected monomers are used to prepare the synthetic test compound polyamides.

An additional useful combination of orthogonal protecting groups involves the trimethylsilylethoxycarbonyl group, which can be removed by fluoride ions, and a highly acid-sensitive protecting group such as Ddz or Bpoc (2-Biphenyl-2-propoxycarbonyl). Either type of protecting group can be used for N-protection during the assembly of either the polyamide, in an encoded polyamide library synthesis, or the coding peptide.

For the synthesis of the peptide coding molecules in preferred encoded libraries, the well-known techniques of solid phase peptide synthesis including suitable protecting group strategies will be used. The relevant published art of peptide synthesis is quite extensive and includes among others Stewart and Young, 1984, "Solid Phase Synthesis", Second Edition, Pierce Chemical Co., Rockford Ill.; Bodanszky, Y. Klausner, and M. Ondetti, "Peptide Synthesis", Second Edition, Wiley, N.Y., 1976; E. Gross and J. Meienhofer (editors), "The Peptides", vol. 1, continuing series, Academic Press, New York, 1979.

5.5 Specific Libraries of Test Compounds and Methods of Synthesis Thereof

Specific types of linkages for the libraries listed in section 5 are described below as well as synthetic reactions which can be used to generate these libraries, i.e., reactions that are used to carry out step (ii) of the general procedure for generating libraries (see section 5.2). As can be readily appreciated by one of ordinary skill in the art from the foregoing discussion and the following exemplary material, any of the numerous condensation reactions known in synthetic chemistry that can proceed in a stepwise fashion with appropriate protection groups can be used to prepare the libraries of the invention. The list of subunits that can be used to prepare such libraries is vast; many suitable reagents can be obtained commercially or synthesized using well known protocols. A partial list of structures of suitable subunits is shown in FIG. 5. Examples of synthetic reactions are described in the following subsections and Schema.

In the Schemes herein, Z is any alkyl, aryl, heteroalkyl or heteroaryl group, containing one or more groups including but not limited to H, —$NH_2$, —OH, $CO_2H$, —$CO_2R$, —CONHR, and the like. Alkyl means a $C_1$ to $C_{20}$ saturated or unsaturated hydrocarbon. Aryl means a $C_5$ to $C_{20}$ aromatic hydrocarbon. P with a circle refers to a separate phase support, e.g., a resin bead. P (without a circle) refers to a protecting group. The remaining symbols have their standard meaning.

These strategies can be employed to prepare encoded libraries by using suitable orthoganol protecting groups as described above.

5.5.1 Libraries Containing Amide Bonds With Subunits Other Than α-Amino Acids

A variety of libraries containing one or more amide bonds, including libraries of polyamides whose structures contain amino acids other than α-amino acids are contemplated. Scheme 1 shows a synthetic strategy for polyamides:

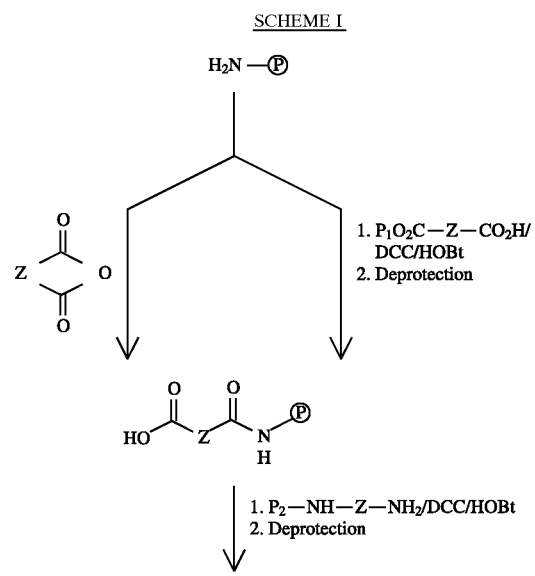

-continued
SCHEME I

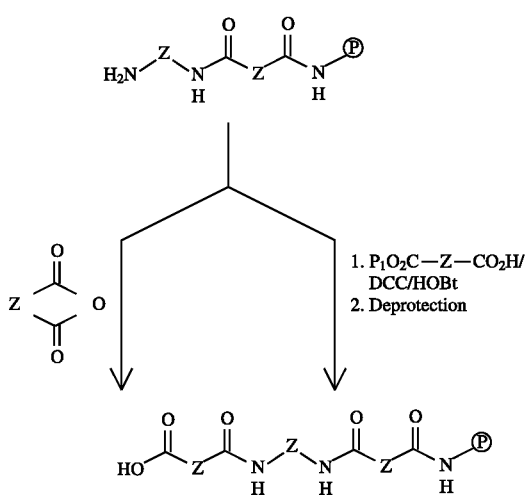

A suitable solid support, such as one of the supports described in section 5.2, is coupled with a carboxylic acid anhydride in a suitable solvent to give a carboxylic acid amide support. The supported acid-amide is further elongated by activation of the carboxyl group, using a compound such as dicyclohexyl carbodiimide (DCC) in the presence of hydroxybenzotriazole (HOBt), followed by condensation with a diamine containing a protected amino group; deprotection of the condensation product gives a diamide-amine on the solid support. Repetition of this synthetic cycle, i.e, sequential reaction with an anhydride, condensation with a single protected diamine, and deprotection, produces a growing polyamide on the solid support. If the completed polyamide sequence contains protecting groups, it is deprotected without detachment from the solid support.

An alternative synthetic approach to polyamides involves modification of the above synthesis by replacement of the anhydride with a partially protected dicarboxylic acid, e.g., a suitable dicarboxylic acid half ester. The resulting ester amide resin is deprotected and activated with, e.g., DCC/HOBt prior to condensation with the diamine.

For the synthesis of synthetic test compound polyamides whose structures contain α-amino acids, such as peptides and peptide mimetics, the peptide synthesis techniques described previously may be used.

In one embodiment, pyroglutamate may be included as the N-terminal residue of the synthetic test polyamides of the library.

In a further embodiment, subunits that confer useful chemical and structural properties will be chosen for incorporation into a synthetic test polyamide sequence. In particular, the present invention envisions preparing libraries of polyamides that have more well defined structural properties than native peptides. In another embodiment, a polyamide library may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such libraries could provide ligands with unique function and activity compared with those of the corresponding native peptides, such as extended half-lives in vivo due to resistance to metabolic breakdown, or protease activity.

A constrained, cyclic or rigid polyamide may be prepared according to the method described previously, provided that, in at least two positions in the sequence of all synthetic test compound, subunits, e.g., amino acids, are inserted that provide chemical functional groups capable of crosslinking to constrain, cyclize or make rigid the polyamide after treatment to form a crosslink. Examples of amino acids capable of crosslinking a peptide are cysteine to form disulfides, aspartic acid to form a lactone or a lactam, and a chelator such as γ-carboxyl-glutamic acid (Gla) (commercially available, e.g., from Bachem) to chelate a transition metal and form a cross-link. Protected γ-carboxyl glutamic acid may be prepared by modifying the synthesis described by Zee-Cheng and Olson (1980, Biophys. Biochem. Res. Commun. 94: 1128–1132). A library in which the polyamide sequence comprises at least two subunits capable of crosslinking may be treated, e.g., by oxidation of cysteine residues to form a disulfide or addition of a metal ion to form a chelate, so as to crosslink the peptide and form a constrained, cyclic or rigid peptide. Cyclic motifs are disclosed in detail in U.S. application Ser. No. 07/717,454, filed Jun. 19, 1991.

Some simple amino acids that can be used as subunits for incorporation into a library include the following:

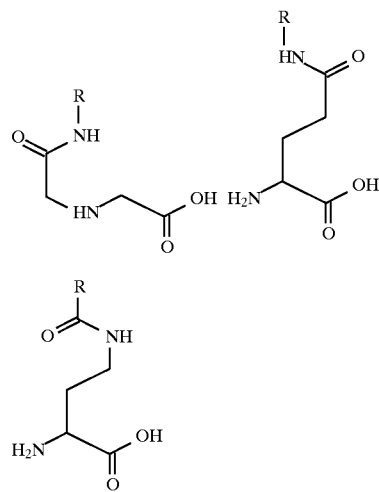

Non-classical amino acids may be used during the synthesis of polyamides. The following non-classical amino acids may be incorporated in a polyamide library in order to introduce particular conformational motifs: 1,2,3,4-tetrahydroisoquinoline-3-carboxylate (Kazmierski et al., 1991, J. Am. Chem. Soc. 113: 2275–2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3, 4-tetrahydroisoquinoline-3-carboxylate (Miyake et al., 1984, J. Takeda Res. Labs. 43: 53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 38: 131–138).

The following amino acid analogs and peptidomimetics may be incorporated into the library of synthetic test compound to induce or favor specific secondary structures: LL-Acp (LL-3-amino-2-propenidone-6-carboxylic acid), a β-turn inducing dipeptide analog (Kemp et al., 1985, J. Org. Chem. 50: 5834–5838); β-sheet inducing analogs (Kemp et al., 1988, Tetrahedron Lett. 29: 5081–5082); β-turn inducing analogs (Kemp et al., 1988, Tetrahedron Lett. 29: 5057–5060); α-helix inducing analogs (Kemp et al., 1988, Tetrahedron Lett. 29: 4935–4938); γ-turn inducing analogs (Kemp et al., 1989, J. Org. Chem. 54: 109: 115); and analogs provided by the following references: Nagai and Sato, 1985, Tetrahedron Lett. 26: 647–650; DiMaio et al., 1989, J. Chem. Soc. Perkin Trans. p. 1687; also a Gly-Ala turn analog (Kahn et al., 1989, Tetrahedron Lett. 30: 2317); amide bond isostere (Jones et al., 1988, Tetrahedron Lett. 29: 3853–3856); tretrazol (Zabrocki et al., 1988, J. Am. Chem. Soc. 110: 5875–5880); DTC (Samanen et al., 1990, Int. J. Protein Pep. Res. 35: 501–509); and analogs taught in Olson et al., 1990, J. Am. Chem. Soc. 112: 323–333 and Garvey et al., 1990, J. Org. Chem. 56: 436.

The present invention further provides for modification or derivatization of synthetic test compound polyamides in a library such as described in U.S. application Ser. No. 07/717,454, filed Jun. 19, 1991. Modifications of peptides are well known to one of ordinary skill, and include phosphorylation, sulfation, carboxymethylation, and acylation. Modifications may be effected by chemical or enzymatic means. Since such modifications may result in non-sequenceable peptides, use of a coding molecule in such libraries is preferred.

In another aspect, glycosylated or fatty acylated peptide derivatives may be prepared. Preparation of glycosylated or fatty acylated peptides is well known in the art (see, e.g., U.S. application Ser. No. 07/717,454).

Fatty-acid polyamide derivatives may also be prepared. For example, and not by way of limitation, a free amino group may be acylated, e.g., myristoylated. This and other peptide-fatty acid conjugates suitable for use in the present invention are disclosed in U.K. Patent GB-8809162.4, International Patent Application PCT/AU89/00166.

5.5.2 Libraries Containing Carbamate Bonds

The present invention encompasses synthetic test compounds that include one or more carbamate (i.e., polyurethane) bonds, including polycarbamates. Two strategies for forming carbamates are shown in Scheme II.

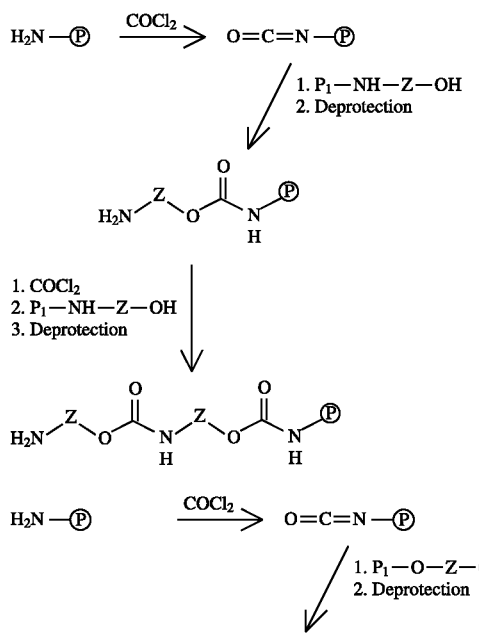

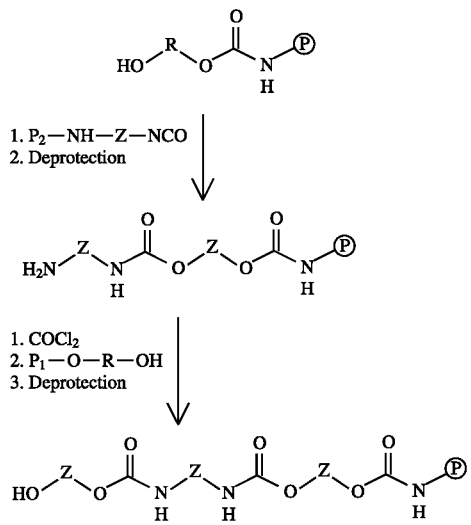

For the synthesis of the two different types of carbamates, couplings of isocyanates and diols or aminoalcohols can be used. For example, a suitable resin, such as the functionalized resin used for the synthesis of polyamides above, is converted to the isocyanate by reaction with phosgene, and the isocyanate is then coupled with an amino-protected aminoalcohol to give the protected carbamate. Deprotection of the resin urethane furnishes an aminourethane resin which is used to repeat the same synthetic cycle producing a polyurethane, i.e., reaction with phosgene followed by coupling with an N-protected aminoalcohol and deprotection produces an amino diurethane resin, etc.

A second type of supported carbamate is produced by modifying the above synthetic procedure as follows. The starting amino resin is converted to the isocyanate, the isocyanate is converted to a protected carbamate by reaction with partially protected diol, the protected carbamate resin is deprotected to give a hydroxycarbamate, the hydroxycarbamate is converted to an aminodicarbamate by reaction with an amino-protected aminoalkylisocyanate, which is followed by deprotection.

5.5.3 Libraries Containing Urea Bonds

A strategy for synthesis of variety of urea-bond containing structures is shown in Scheme III.

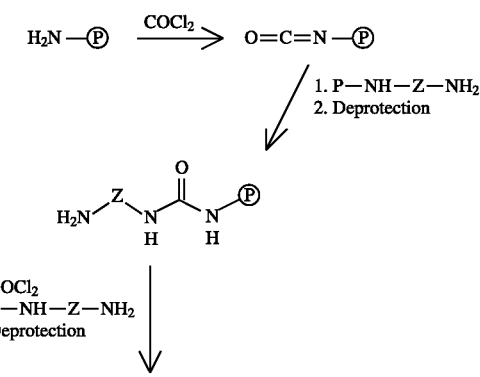

23
-continued
SCHEME III

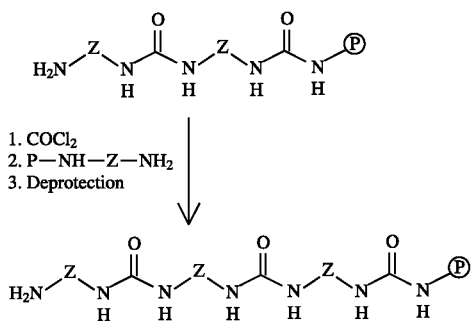

A suitable resin functionalized with isocyanate groups, such as the resin used in the synthesis of the carbamates described above, is converted to an amino urea by reaction with a partially protected diamine followed by deprotection, and the amino urea resin to an isocyanate using phosgene. The isocyanatourea resin is subjected to the above three-step synthetic cycle the desired number of times producing polyureas.

5.5.4 Libraries Containing Ester Bonds

A strategy for the synthesis of libraries containing ester bonds is shown in Scheme IV.

24
SCHEME IV

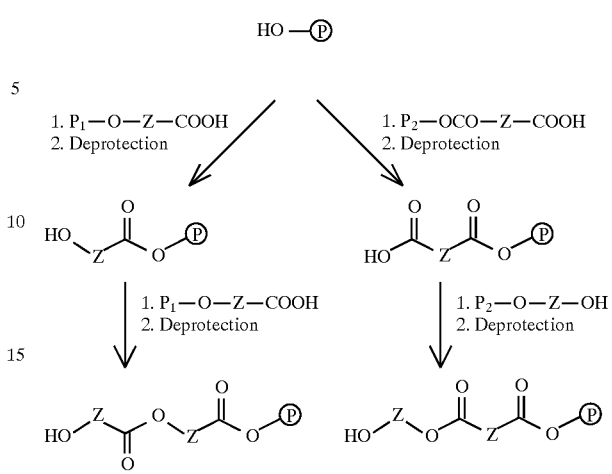

A suitable resin, such as the hydroxyalkyl resin used in Merrifield solid phase peptide synthesis, in a swelling solvent such as methylene chloride, is condensed with a suitably protected hydroxycarboxylic acid, preferably in the presence of a condensing agent such as DCC, to give, after deprotection, a supported hydroxyester which is further elongated using the same acylation-deprotection cycles.

5.5.5 Libraries Containing Amine Bonds

A strategy for the synthesis of amines is shown in scheme V:

SCHEME V

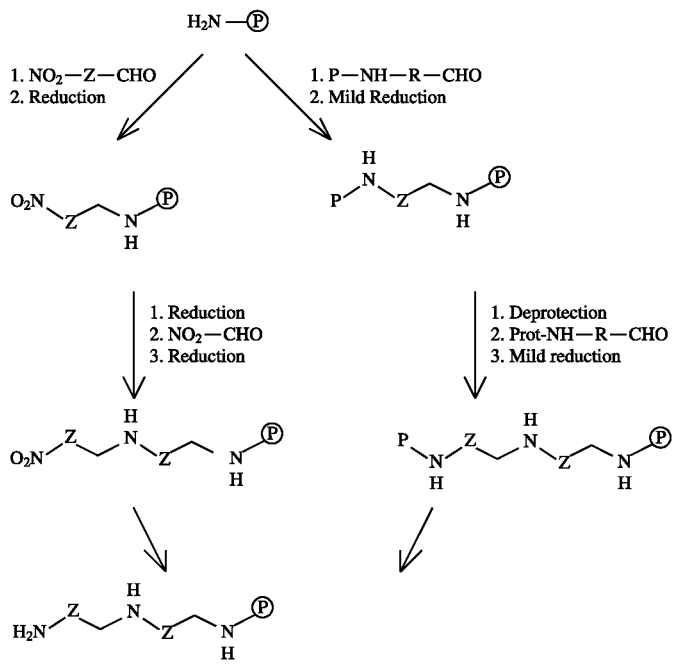

A suitable resin, such as the resin used in the amide synthesis above, is converted to a nitroalkyl amine resin via reductive amination using a nitroaldehyde, and further reduced to the primary amine, using one of many reactions known to reduce nitroalkamines to primary amines (e.g., reduction by lithium aluminum hydride). The primary amine on the resin is elongated by repeating the reductive-alkylation-reduction sequence, producing the desirable polyamine.

The reduction of a nitroalkylamine resin in the procedure above can be avoided by replacing the nitroaldehyde of the reductive amination with an N-protected aminoaldehyde and removing the protecting group of the resulting product in a separate synthetic step.

5.5.6 Libraries Containing Sulfides and Disulfide Bonds

A strategy for synthesis of a variety of polysulfide and polydisulfide structures is shown in scheme VI:

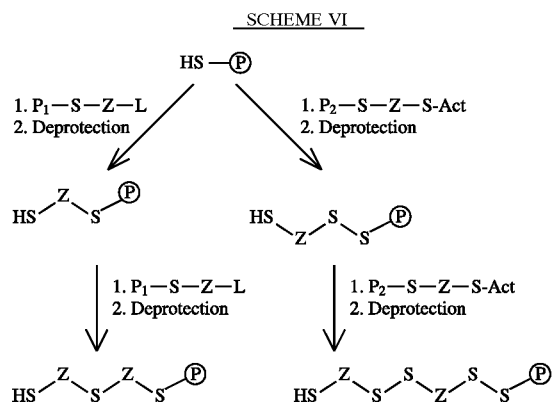

A suitable resin, e.g., a resin used in Merrifield solid phase peptide synthesis, is functionalized to have free thiol groups. The thiol resin is alkylated with a protected thioalkyl halide and the product deprotected to give a thioalkyl resin sulfide. The supported thioalkylsulfido chain is further elongated by repeating the alkylation-deprotection cycle to furnish a supported polysulfide.

The above synthesis can yield supported disulfides if the protected thioalkyl halide is replaced by a protected thioalkylchlorosulfenate or thioalkylmethoxycarbonylsulfenate.

5.5.7 Libraries Containing Carbon-Carbon Bonds

A variety of polyalkanes, polyalkenes, polyhaloalkene and, polyols are contemplated. Strategies for the synthesis of such libraries are shown in Scheme VII:

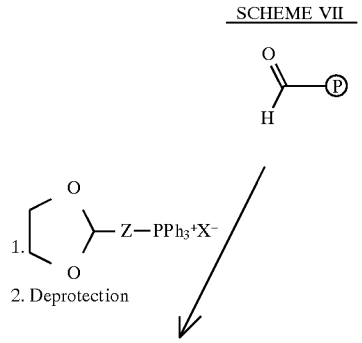

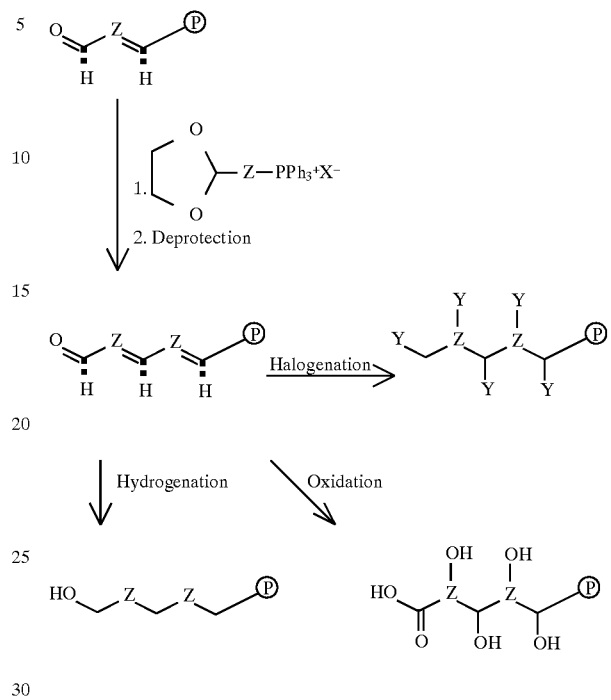

A suitable resin is functionalized with carbonyl groups, (e.g., by controlled oxidation of support hydroxyalkyl groups), condensed with a Wittig reagent, prepared from triphenyl phosphine and a haloalkyl dialkyl acetal, and deprotected to give a resin containing an unsaturated aldehyde chain. This chain can be elongated to a polyene aldehyde using the same Wittig-condensation-deprotection sequence. Treatment of the supported polyene with a molecular halogen, such as chlorine or bromine produces a haloalkane on a resin. Conversion of these haloalkanes to their fully dehalogenated reduced derivatives by reaction with tributyl tin hydride or an electropositive metal such as zinc in the presence of a weak acid is also contemplated. Careful treatment of the supported polyene with an oxidizing agent, e.g., permanganate or periodate, produces polyols. Other polyols may be produced by subjecting the polyene to a hydroboration-oxidation sequence, an epoxidation (by a peracid such as m-chloroperbenzoic acid)-hydrolysis sequence, or a mercuric-acetate-alkaline-borohydride sequence.

5.5.8 Libraries of Polycyclic Compounds and Functionalized Polycyclic Compounds A variety of polycyclic and functionalized polycyclic compounds are contemplated. A strategies for the synthesis of polycyclic and related structures are shown in Scheme VIII, in which $R_1$, $R_2$ and $R_3$ refer various substituted alkyl or aryl groups as defined above:

SCHEME VIII

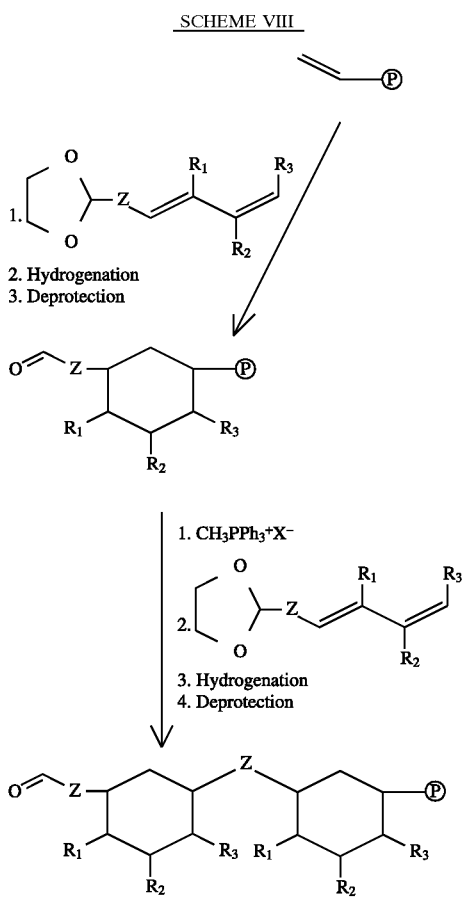

Scheme VIII shows preparation of a saturated hydrocarbon. Alternatively, unsaturated structures can also be prepared. A suitable resin, such as the carbonyl resin described above, is converted to an alkene resin, e.g., by a Wittig condensation, and this resin is used in a Diels-Alder-type pericyclic reaction with a suitably activated, e.g., electrophilic, diene dimethylacetal to produce, after hydrolysis of the acetal group, a supported functionalized cyclohexenyl aldehyde. This supported structure can be further elongated by repetition of the Wittig-condensation-Cycloaddition-deprotection sequence producing a supported poly-cyclohexene aldehyde which can be further functionalized as follows (i) by halogenation, e.g., bromination or chlorination, to give a poly-halocyclohexanyl aldehyde, (ii) by reduction of the poly-halocyclohexanyl aldehyde, e.g., using tributyltin hydride or an electropositive metal (e.g., Zn) and a weak acid, producing a polycyclohexane aldehyde or alcohol, and (iii) by controlled oxidation of the polycyclohexane aldehyde using permanganate, a hydroboration-oxidation sequence, an epoxidation-hydrolysis sequence, or an epoxidation-reduction sequence (e.g., epoxidation by m-chloroperbenzoic acid followed by reduction by lithium aluminum hydride) producing a functionalized polyol.

Another example of a cyclic library is shown in FIG. 6. This library is prepared by attaching bromo-propionic acid to a support, and attaching Boc-protected cysteine methyl ester to the support via substitution of bromine with the sulfur side chain to form a sulfide linkage. Boc/Fmoc protected diamino acids, such as diaminobutyric acid or lysine, can be added. Deprotection of one protecting group allows substitution with any carboxylic acid. Deprotection of the other amino group allows addition of another diamino acid. This sequence of steps is repeated the desired number of times. Finally, the methyl ester group is hydrolyzed from cysteine, allowing reaction with a deprotected amino group to cyclize the structure.

5.5.9 Libraries of Polysubstituted Ring Structures Capable of Serving as a Scaffolding A variety of polysubstituted structures capable of serving as a scaffolding are contemplated. A general strategy for the synthesis of such structure is shown in Scheme IX:

SCHEME IX

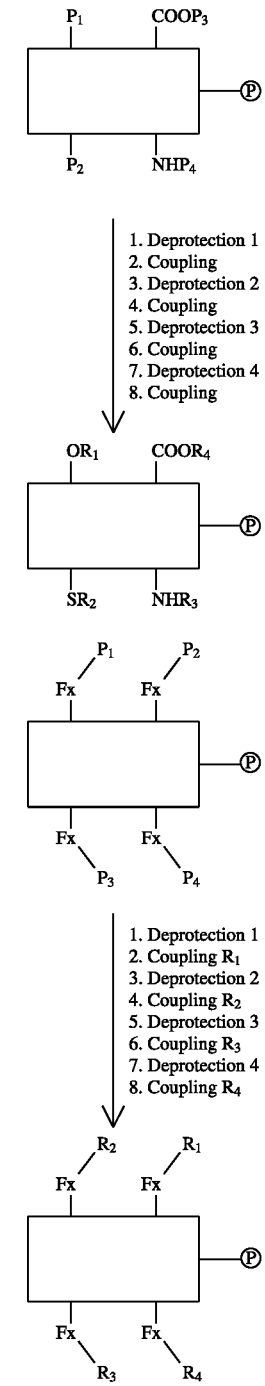

A general strategy for preparation of a specific type of scaffold libraries is shown in scheme X:

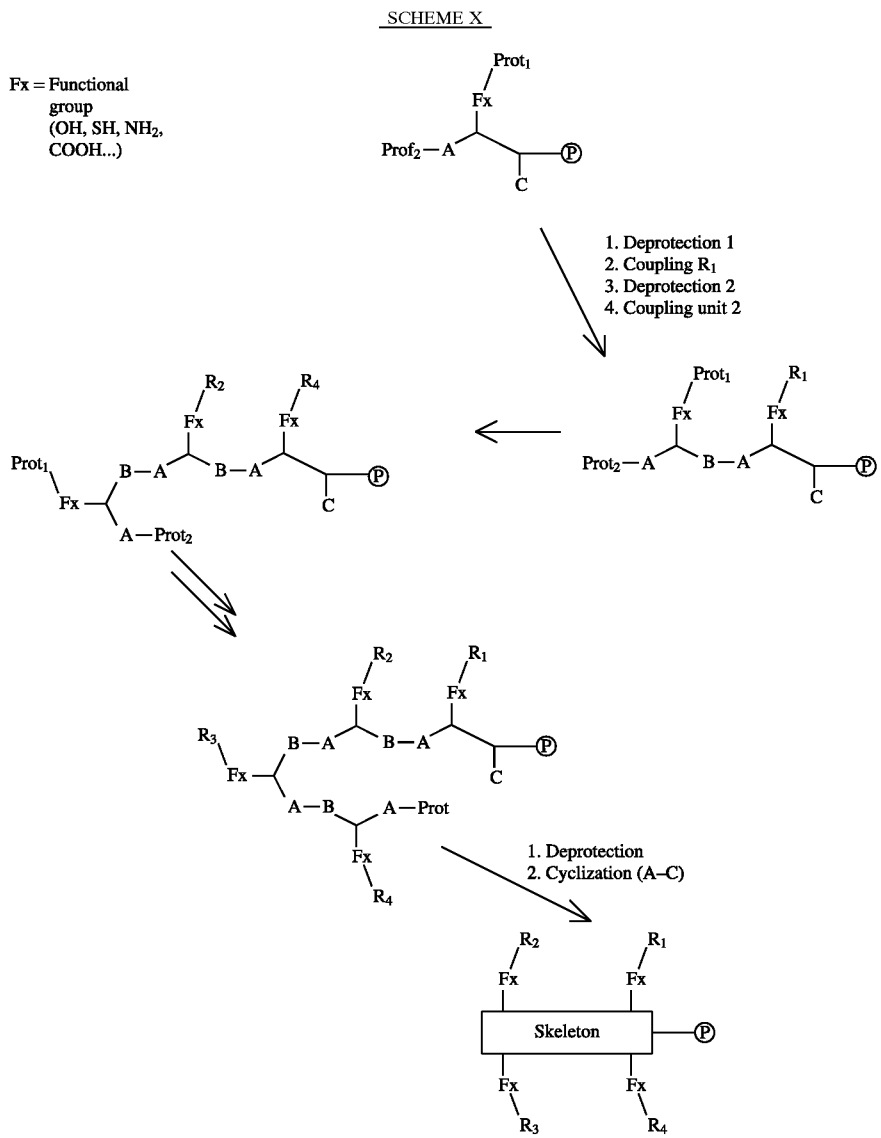

Suitable scaffolds include but are not limited to cyclopentane, Kemp's triacid (Kemp and Petrakis, 1981, J. Org. Chem. 46: 5140–5143), a branched construct prepared by consecutive coupling of diamino carboxylic acids, cyclic templates such as are described by Mutter, et al. (1992, J. Am. Chem. Soc. 114-1463–1470), steroids, benzodiazepines, and the like.

An approach for the attachment of a derivative of cis-1,3,5-cyclohexane tricarboxylic acid to a Merrifield-type resin followed by derivatization of each of the three carboxyl groups of the triacid is described in Section 9, infra, as one example of a synthesis of a supported polysubstituted ring structure capable of serving as a scaffolding (see Scheme XIV, infra).

As a second example of a synthesis of a polysubstituted ring structure capable of serving as a scaffolding, the assembly and derivatization of 1,4-benzodiazepines, based on the published work of Ellman and Bunin (*Chemical & Engineering News,* Jan. 18, 1993, p. 33), is given below. In a specific embodiment, a suitable resin, such as a Merrifield-type resin functionalized with a 4-hydroxymethylphenoxyacetic acid linker, is further functionalized with a 2-amino-4'-hydroxybenzophenone, whose amino group is protected with the fluorenylmethoxycarbonyl (Fmoc) group. After removal of Fmoc, coupling of the resulting aniline with an Fmoc-protected amino acid, to produce an anilide, removal of Fmoc from the anilide and cyclization, a supported 1,4-benzodiazepine is produced which can be further alkylated on the anilide nitrogen, using a variety of electrophiles, to produce a variety of benzodiazepine derivatives for further study.

One of the smallest possible ring structures for use as a scaffold is the cyclopentane ring (FIG. 7).

Encoded versions of the polysubstituted ring structures libraries described above are preferred embodiments. Encoded libraries in which the coding molecules are peptides are most preferred. For the synthesis of the peptide-encoded libraries the general procedure of section 5.1 and the synthetic strategies outlined in sections 5.2 and 5.3 are used.

5.5.10 Libraries Based on Scaffolding Constructed From Amino Acids

A scaffolding, mapping larger conformational space, that is a simple branched attachment, is constructed by consecutive coupling of diamino carboxylic acids (see FIG. 3). Various types of the scaffolding mapping extensive space are flexible cyclic or branched scaffoldings. The principles of these libraries are illustrated in FIG. 3. As an example of scaffold library construction we show here synthesis of branched library (Scheme XV, Section 9, infra).

5.6 Methods of Detection and Identification of Ligands in Libraries of Test Compounds In addition to providing libraries of a great variety of chemical structures as synthetic test compound, and methods of synthesis thereof, the present invention further comprises methods of screening the test compounds of a library to identify ligands within the library that demonstrate a biological activity of interest, such as binding, stimulation, inhibition, toxicity, taste, etc. Other libraries may be screened according to the methods described infra for enzyme activity, enzyme inhibitory activity, and chemical and physical properties of interest. Many screening assays are well known in the art; numerous screening assays are also described in U.S. patent application Ser. No. 07/717,454, filed Jun. 19, 1991).

The ligands discovered during an initial screening may not be the optimal ligands. In fact, it is often preferable to synthesize a second library based on the structures of the ligands selected during the first screening. In this way, one may be able to identify ligands of higher activity.

5.6.1 Binding Assays

The present invention allows identification of synthetic test compound that bind to acceptor molecules. As used herein, the term "acceptor molecule" refers to any molecule which binds to a ligand. Acceptor molecules may be biological macromolecules such as antibodies, receptors, enzymes, nucleic acids, or smaller molecules such as certain carbohydrates, lipids, organic compounds serving as drugs, metals, etc.

The synthetic test compound in libraries of the invention can potentially interact with many different acceptor molecules. By identifying the particular ligand species to which a specific acceptor molecule binds, it becomes possible to physically isolate the ligand species of interest.

Because only a small number of solid support beads will be removed during each screening/detection/isolation step, the majority of the beads will remain in the bead pool. Therefore, the library can be reused multiple times. If different color or identification schemes are used for different acceptor molecules (e.g., with fluorescent reporting groups such as fluorescein (green), Texas Red (Red), DAPI (blue) and BODIPI tagged on the acceptors), and with suitable excitation filters in the fluorescence microscope or the fluorescence detector, different acceptors (receptors) can be added to a library and evaluated simultaneously to facilitate rapid screening for specific targets. These strategies not only reduce cost, but also increase the number of acceptor molecules that can be screened.

In the method of the invention, an acceptor molecule of interest is introduced to the library where it will recognize and bind to one or more ligand species within the library. Each ligand species to which the acceptor molecule binds will be found on a single solid phase support so that the support, and thus the ligand, can be readily identified and isolated.

The desired ligand can be isolated by any conventional means known to those of ordinary skill in the art and the invention is not limited by the method of isolation. For example and not by way of limitation, it is possible to physically isolate a solid-support-bead ligand combination that exhibits the strongest physico-chemical interaction with the specific acceptor molecule. In one embodiment, a solution of specific acceptor molecules is added to a library which contains $10^5$ to $10^7$ solid phase support beads. The acceptor molecule is incubated with the beads for a time sufficient to allow binding to occur. Thereafter, the complex of the acceptor molecule and the ligand bound to the support bead is isolated. More specific embodiments are set forth in the following methods, which describe the use of a monoclonal antibody, as a soluble acceptor molecule to bind a ligand which is a peptide. It will be clear that these methods are readily adaptable to detect binding of any acceptor molecule.

In addition to using soluble acceptor molecules, in another embodiment, it is possible to detect ligands that bind to cell surface receptors using intact cells. The use of intact cells is preferred for use with receptors that are multi-subunit or labile or with receptors that require the lipid domain of the cell membrane to be functional. The cells used in this technique may be either live or fixed cells. The cells will be incubated with the library and will bind to certain peptides in the library to form a "rosette" between the target cells and the relevant bead-peptide. The rosette can thereafter be isolated by differential centrifugation or removed physically under a dissecting microscope.

Alternatively, one may screen the library using a panning procedure with cell lines such as (i) a "parental" cell line where the receptor of interest is absent on its cell surface, and (ii) a receptor-positive cell line, e.g., a cell line which is derived by transfecting the parental line with the gene coding for the receptor of interest. It is then possible to screen the library by the following strategy: (i) first depleting the library of its non-specific beads that will bind to the cells lacking the receptor by introducing a monolayer of parental cell line by the standard "panning technique" to leave receptor-specific non-binding beads, or irrelevant non-binding beads (ii) removing the non-binding beads which will include both receptor-specific or irrelevant beads and loading them on a monolayer of receptor positive cell line in which the receptor-specific bead will bind to the receptor positive cell line, (iii) removing the remaining irrelevant non-binding beads by gentle washing and decanting, and (iv) removing the receptor-specific bead(s) with a micromanipulator, such as a micropipette.

As an alternative to whole cell assays for membrane bound receptors or receptors that require the lipid domain of the cell membrane to be functional, the receptor molecules can be reconstituted into liposomes where reporting group or enzyme can be attached.

The foregoing examples refer to synthetic test compound, and any of the compounds described in Sections, supra, may be used in the practice of the instant invention. Thus, an acceptor molecule may bind to one of a variety of polyamides, polyurethanes, polyesters, polyfunctionalized structure capable of acting as a scaffolding, etc.

In one embodiment, the acceptor molecule may be directly labeled. In another embodiment, a labeled secondary reagent may be used to detect binding of an acceptor molecule to a solid phase support particle containing a ligand of interest. Binding may be detected by in situ formation of a chromophore by an enzyme label. Suitable enzymes include, but are not limited to, alkaline phosphatase and horseradish peroxidase. In a further embodiment, a two color assay, using two chromogenic substrates with two enzyme labels on different acceptor molecules of interest, may be used. Cross-reactive and singly-reactive ligands may be identified with a two-color assay.

Other labels for use in the invention include colored latex beads, magnetic beads, fluorescent labels (e.g., fluoresceine isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels. Two color assays may be performed with two or more colored latex beads, or fluorophores that emit at different wavelengths. Labeled beads may be isolated manually or by mechanical means. Mechanical means include fluorescence activated sorting, i.e., analogous to FACS, and micromanipulator removal means.

In specific examples, infra, enzyme-chromogen labels and fluorescent (FITC) labels are used.

Reactive beads may be isolated on the basis of intensity of label, e.g., color intensity, fluorescence intensity, magnetic strength, or radioactivity, to mention a few criteria. The most intensely labeled beads may be selected and the ligand attached to the bead may be structurally characterized directly e.g., by Edman sequencing or by mass spectral analysis if applicable, or indirectly by sequencing the coding peptide corresponding to the ligand of interest. In another embodiment, a random selection of beads with a label intensity above an arbitrary cut-off may be selected and subjected to structural analysis. One can potentially use modern image analysis microscopy to quantitate the color intensity, and hence precisely define the relative affinity of the ligand to the acceptor molecule prior to the structure analysis of the bead ligand. Similarly, quantitative immunofluorescence microscopy can be applied if the acceptor is tagged with a fluorescent label. In yet another embodiment, beads demonstrating a certain label intensity are selected for compositional analysis, e.g., amino acid composition analysis in the case of peptide ligands. A refinement library comprising a restricted set of amino acid subunits identified as important from the amino acid analysis may then be prepared and screened.

In another embodiment, the ligand(s) with the greatest binding affinity may be identified by progressively diluting the acceptor molecule of interest until binding to only a few solid phase support beads of the library is detected. Alternatively, stringency of the binding with the acceptor molecule, may be increased. One of ordinary skill would understand that stringency of binding may be increased by (i) increasing solution ionic strength; (ii) increasing the concentration of denaturing compounds such as urea; (iii) increasing or decreasing assay solution pH; (iii) use of a monovalent acceptor molecule; (iv) inclusion of a defined concentration of known competitor into the reaction mixture; and (v) lowering the acceptor concentration. Other means of changing solution components to change binding interactions are well known in the art.

In another embodiment, ligands that demonstrate low affinity binding may be of interest. These may be selected by first removing all high affinity ligands and then detecting binding under low stringency or less dilute conditions.

In a preferred embodiment, a dual label assay may be used. The first label may be used to detect non-specific binding of an acceptor molecule of interest to beads in the presence of soluble ligand. Labelled beads are then removed from the library, and the soluble ligand is removed. Then specific binding acceptor molecule to the remaining beads is detected. Ligands on such beads may be expected to bind the acceptor molecule at the same binding site as the ligand of interest, and thus to mimic the ligand of interest. The dual label assay provides the advantage that the acceptor molecule of interest need not be purified since the first step of the assay allows removal of non-specific positive reacting beads. In a preferred embodiment, fluorescent-labeled acceptor molecules may be used as a probe to screen a synthetic test library, e.g., using FACS.

5.6.2 Bioactivity Assays

The instant invention further provides assays for biological activity of a ligand-candidate from a library treated so as to remove any toxic molecules remaining from synthesis, e.g., by neutralization and extensive washing with solvent, sterile water and culture medium. The biological activities that may be assayed include toxicity and killing, stimulation and growth promotion, signal transduction, biochemical and biophysical changes, and physiological change.

In a preferred embodiment, the synthetic test compound of the library are selectively cleavable from the solid-phase support, also referred to herein as "bead". Preferably, the synthetic test compound are attached to the separate phase support via multiple cleavable linkers to allow for more than one release and screening assay. In one embodiment, beads are prepared such that only a fraction of synthetic test compound are selectively cleavable. Selectively cleavable ligand-candidates, linkers and beads are discussed in Section 5.3.2, supra. A library is treated with a cleaving agent such that cleavage of a fraction of synthetic test compound occurs. Examples of cleaving agents include, but are not limited to, UV light, acid, base, enzyme, or catalyst. In one embodiment, the library is treated so that 10–90% of the synthetic test compound are released. In a more preferred embodiment, 25–50% of the synthetic test compound are released. Where all synthetic test compound molecules are cleavable, non-quantitative cleavage can be effected by limiting the cleaving agent. In one aspect, exposure time and intensity of UV light is limited. In another embodiment, the concentration of reagent is limited. After treatment to effect cleavage, the library may be further treated, e.g., by neutralization, to make it biologically compatible with the desired assay. In practice, one of ordinary skill would be able to readily determine appropriate cleavage conditions for partial cleavage when all synthetic test compound molecules of the library are attached to solid phase by cleavable linkers or bonds. One of ordinary skill would further understand that the relative concentration of released synthetic test compound can be affected by varying the cleavage conditions.

Since the beads of the library are immobilized, a concentration gradient of a particular ligand-candidate will form. High concentrations of synthetic test compound will be found in proximity of the bead from which it was released. Thus, evidence of biological activity of interest, in proximity to a bead, will allow identification and isolation of the bead, and structural characterization by sequencing the coding molecule corresponding to the synthetic test compound or other technique. Identification of the synthetic test compound is possible because enough will be left on the bead after partial cleavage for sequencing or other characterization. In another embodiment, the beads may be partitioned in microtiter wells (e.g., 10 beads/well) and a fraction of ligand-candidate released and tested for biological activity, thus eliminating the potential problem of diffusion. Different portions of synthetic test compound may be attached to solid phase support or bead via different cleavable linkers for sequential assays. Within these examples, the term "bead" refers to a separate phase support particle.

Biological assays with uncleaved synthetic test compound are also envisioned. The biological activity of whole synthetic test compound-coated beads may then be screened. In one aspect, a library may be introduced into an animal. Beads of interest may be isolated from a specific tissue. Beads may be isolated that were specifically absorbed after oral, nasal, or cutaneous administration. In a preferred embodiment, such beads are magnetic, or have some other identifying feature, and thus are readily isolated from the tissue. In another embodiment, immobilized ligand itself may elicit biochemical changes with appropriate surface receptors.

It will further be understood by one of ordinary skill in the art that any cell that may be maintained in tissue culture, either for a short or long term, may be used in a biological assay. The term "cell" as used here is intended to include prokaryotic (e.g., bacterial) and eukaryotic cells, yeast, mold, and fungi. Primary cells or lines maintained in culture may be used. Furthermore, applicants envision that biological assays on viruses may be performed by infecting or transforming cells with virus. For example, and not by way of limitation, the ability of a ligand to inhibit lysogenic activity of lambda bacteriophage may be assayed by identifying transfected *E. coli* colonies that do not form clear plaques when infected.

Methods of the present invention for assaying activity of a synthetic test compound molecule of a library are not limited to the foregoing examples; applicants envision that any assay system may be modified to incorporate the presently disclosed invention. Applicants envision that such are within the scope of their invention.

5.6.3 Enzyme Mimics/Enzyme Inhibitors

The present invention further comprises libraries that are capable of catalyzing reactions, i.e., enzyme libraries; libraries of molecules that serve as co-enzymes; and libraries of molecules that can inhibit enzyme reactions. Thus, the invention also provides methods to be used to assay for enzyme or co-enzyme activity, or for inhibition of enzyme activity.

Enzyme activity may be observed by formation of a detectable reaction product. In a particular embodiment, an enzyme from an enzyme library catalyzes the reaction catalyzed by alkaline phosphatase, e.g., hydrolysis of 5-bromo-4-chloro-3-indoyl phosphate (BCIP) and forms a blue, insoluble reaction product on the solid phase support (see Example 13, infra).

In another embodiment, a zone of observable product, e.g., color or fluorescence, may be formed in a semi-solid matrix. A library is layered in a semi-solid matrix, e.g., agarose gel, and a chromogenic or other indicator substrate is added. Where an enzyme-bead complex from an enzyme library shows the desirable enzyme activity, a zone of product will form. For example, and not by way of limitation, a molecule from a library which is an analog of horseradish peroxidase may be identified by adding a solution of aminoantipyrene (0.25 mg/ml; Kodak), phenol (8 mg/ml) and $H_2O_2$ (0.005%) in 0.1M phosphate buffer, pH 7.0. Beads with enzyme activity will form a purple zone of color. In another embodiment, beads with protease activity may be identified by addition of the well known colorimetric protease substrates.

Co-enzyme activity may be observed by assaying for the enzyme activity mediated by a co-enzyme, where the natural or common co-enzyme is absent.

Enzyme inhibitory activity can be detected with a partially-released synthetic test compound. In one example, and not by way of limitation, a library is layered in a semi-solid matrix that contains an enzyme. The library is treated to partially release ligand-candidate molecules. Where the molecule inhibits the enzyme activity, a zone lacking product may be identified. In one embodiment, the enzyme substrate is chromogenic, and a colored product is formed. Thus, presence of an enzyme inhibitor would yield a zone of no color. In another embodiment, inhibition of proteolysis of hemoglobin or an indicator enzyme such as alkaline phosphatase may be detected by the presence of an opaque zone in the semi-solid matrix. This is because presence of proteolysis inhibitor will prevent degradation of the hemoglobin or indicator enzyme.

It will be well known to one of ordinary skill that a synthetic test compound molecule that demonstrates enzyme activity, co-enzyme activity, or that inhibits enzyme activity, may be a peptide, a peptide mimetic, one of a variety of polymers or any of the compounds described in Section 5. Of particular interest are the constrained polymers, including but not limited to cyclic, bicyclic or tricyclic structures, or constrained structures with certain scaffolding, which can create an unique catalytic binding pocket or surface.

5.6.4 Topological Segregation

The invention further encompasses a method of segregating the coding molecule in the interior of the solid support and the test compound on the exterior, accessible to a macromolecular acceptor molecule of interest. The method encompasses the steps of synthesizing a linker, which in the preferred embodiment is a peptide. The linker contains a sequence which can be hydrolyzed by a conveniently available enzyme such as chymotrypsin or other endopeptidase. In one embodiment the enzyme is chymotrypsin and the linker contains a phenylalanine. After the linker is synthesized, the $N^{\alpha}$ amino function is left protected and the support is exposed to the endopeptidase. The endopeptidase acts only on linkers that would be accessible to other macromolecules, such as acceptors.

After the enzymatic hydrolysis of the peptide linker, the test compound and the coding compounds can be synthesized using any orthogonal protecting groups.

5.7 Methods of Characterizing a Synthetic Test Compound from a Library

Once a support containing a ligand of interest is selected according to any one of the methods of Section 5.6, supra, the present invention provides a means of determining the structure of the ligand.

There are two general approaches to determining the structure of a test compound: the structure of the polymer may be directly analyzed by conventional techniques, e.g., Edman degradation or mass spectrometry; alternatively, a second molecule or group of molecules can be synthesized during the construction of the library such that the structure (s) of the second molecular species unambiguously indicates (encodes) the structure of the test compound attached to the same support. By this second technique, the structure of polymers that are not themselves amenable to sequencing can be readily determined.

Yet another embodiment of the present invention encompasses a third coding technique, termed "fractional coding," which differs from the previous embodiments in that there is not a distinct coding molecule different from the test compound. Fractional coding is used when specific subunits of the test compound are not resolvable in conventional analysis, e.g., the D and L stereo isomers of an amino acid. Fractional coding provides a method whereby the subunits can be distinguished by mixing a small amount of a different subunit one, not otherwise utilized in the construction of the library, at the time the library is synthesized. Thus, fractional coding creates a minor, detectable degree of heterogeneity of the test compound of the support when one of the two indistinguishable subunits is used. For the purposes of the present invention such a degree of heterogeneity, typically about 5%, is compatible with the teaching of the application that there be only one species of test compound on each support.

5.7.1 Characterization by Means of Single and Multiple Sequential Codes

In a preferred embodiment of the encoded molecular libraries, the separate phase support containing the synthetic test compound of interest also contains a molecule, preferably a peptide, whose sequence encodes the structure of the ligand, e.g., determination of the sequence of the coding peptide reveals the identity of the ligand. A preferred method of determining the peptide sequencing is Edman degradation. A particularly preferred method employs the Applied Biosystems 477A Protein Sequencer. The amino acid sequence of peptides can also be determined either by fast atom bombardment mass spectroscopy (FAB-MS) or using other analytical techniques.

The coding peptides can be sequenced either attached to or cleaved from the solid support. To cleave the peptides, the isolated beads are treated with traditional cleaving agents known to those of skill in this art to separate peptides from solid phase supports. The choice of cleaving agent selected will depend on the solid phase support employed.

Alternatively, in another embodiment within the scope of the invention, it is possible to isolate a single solid phase support particle, such as a bead, with its coding peptide sequence attached and introduce the bead to a sequencer for peptide sequencing without previously cleaving the coding peptide from the bead. It is estimated that a single 100 $\mu$m diameter resin bead with 0.5 mEq/gram of functionalizable sites contains approximately 100 pmole of peptide if one half of the sites are used to link coding peptides. For a similar degree of substitution with coding peptides, a single 250 $\mu$m diameter PAM resin bead with 0.5 mEq/gram resin of functionalizable sites contains approximately 1500 pmole of coding peptide. With a state of the art peptide sequencer, only 5–10 pmole is required for adequate sequencing. Therefore, for a standard PAM resin a single bead of 100 $\mu$m in diameter can be loaded to contain more than an adequate amount of coding peptide for sequencing.

In addition to Edman sequencing, fast ion bombardment mass spectrometry is a very powerful analytical tool and can often be used effectively to analyze the structures of peptides and of a variety of other molecules. Electrospray-high performance mass spectrometry can also be very useful in structural analysis. Preferably, mass spectrometry to determine the structure of a coding molecule is performed as described in U.S. patent application Ser. No. 07/939,811, filed Sep. 3, 1992.

Those skilled in the art will appreciate that at times the number of species of subunits at any position of the test compound is larger than the number of monomers used to construct the coding polymer. For example, a coding peptide can be constructed with a limited set of amino acids that are readily distinguished after Edman degradation. Under these circumstances the coding molecule can be constructed by introducing a mixture of amino acids at a given position. For example a singlet/doublet code, i.e., having one or two coding moieties per position of the test compound, in which the coding polypeptide contains only 8 amino acids can encode up to 36 subunits; a triplet/doublet/singlet code with the same number of moieties encodes 84 subunits per position.

The analysis of the Edman degradation products of such coding peptides will reveal either one or two, or one, two or three animo acids at each position of the coding sequence.

5.7.2 Characterization by Means of a Non-Sequential Code

An alternative preferred embodiment, termed non-seqential coding allows for the "reading" of the coding molecule without a determination of the sequence of its subunits. Sequential codes are inherently laborious to decode. Sequencing of a molecule requires reiterated degradative steps. By contrast analysis of the composition of a polymeric molecule can be performed by a single degradation and single analysis of the resultant subunits or their derivatives.

Further, the most time consuming of the steps required to sequence a peptide coding molecule is the chromatographic analysis of each of the cleaved phenylthiohydantoins. Even though all the information resides in the unique retention time of the single eluted peak, a separate chromatography step must be performed on the products of each step-wise degradation. Thus, most of the time of gradient analysis is "wasted" waiting for the appearance of the single peak corresponding to the residue at that position. The process is clearly not as efficient as possible. If instead of sequential Edman degradation followed by HPLC analysis, it were possible to simultaneously cleave all the coding subunits, distinguish among them in a single HPLC run, and then decode the results to determine the test compound identity, the process could be greatly accelerated.

The reading of a non-sequential code requires only determining whether a given signal is present or not. The baseline resolution of two peaks which differ by about 0.3 minutes in retention time can be achieved using standard reversed phase HPLC analysis with gradient elution. Therefore, a 45 minute gradient can discrimate among 150 compounds. A coding molecule consisting of subunits selected from a group of 150 different coding moieties is equivalent to a 150 digit binary number. Hence, $2^{150}$ or about $10^{45}$ different species of test compound could be so encoded. Thus, non-sequential codes are easily adequate to encode both the sequence and the identity of the subunits of the test compounds of even the largest practical libraries.

A non-sequential code can be constructed as follows. Let C000 to C099 be the elements of the set of 100 coding moieties to be used to encode the structure of a test compound having up to 20 residues selected from up to 32 different subunits, called here S00–S31. In this scheme the identity of the residue at the first position is determined by the presense or absence of coding elements C000–C004; if none are present S00 is present at the first position of the test compound, if all are present S31 is present at position 1. Successive positions are encoded by moieties C005–C009, C010–C014 . . . C095–C099. Those of ordinary skill will understand that, in the frequent case wherein libraries considerably smaller than the maximum coding capacity of a 100 digit code are required; the fidelity of the code may be increased by either reducing the size of the set of coding moleules, i.e., increasing the interval between moieties in the chromatographic analysis, or by the use of redundant coding, e.g., a "parity" moiety may be introduced into the code for each encoded position.

Most frequently, between 4 and 8 coding moieties, corresponding to between 16 subunits and 128 subunits plus a parity moiety, will be required to encode each position in the test compound.

The coding moieties need to be arranged in the coding structure to allow their simultaneous cleavage and analysis. One obvious possibility is total hydrolysis, followed by selective modification and analysis of the mixture. In this case the structure of the coding compound is not important.

Coding moieties can be connected to one another, or attached to separate branches of a branched structure, or any combination so long as the bond to each moiety is hydrolyzable. This approach, however, might be compromised by the presence of hydrolytic products from the test compound. Therefore, the use of the very selective degradation method designed by Edman, 1950, *ACTA CHEM SCAND*, 4: 283–293; Edman, et al., 1967, *EURO J BIOCHEM*, 1: 80–91 seemed the optimal choice.

Edman degradation selectively cleaves the N-terminal amino acid from the peptide chain. If reasonable number of amino acids and amino acid derivatives fulfilling the chromatographic requirements defined above could be identified, and they were synthesized as a coding structure in an arrangement allowing their simultaneous cleavage, it would be possible to analyze the composition of a nonpeptidic structure in just one cycle of Edman degradation and HPLC analysis.

The retention time of amino acid phenylthiohydantoins on reversed phase follows the lipophilicity of the side chain of the amino acid. Thus, to design a set of amino acid derivatives with the appropriate retention times it is only necessary to design the side chain of each with appropriate differences in lipophilicity. One simple way to achieve the appropriate differences is to substitute the functional group of the side chains of trifunctional amino acids by appropriate substituents. Consequently, we explored the effect of acylating the side chain amino group of diamino carboxylic acids—diaminopropionic acid, diaminobutyric acid, ornithine and lysine. Alternative sets of coding moieties such as derivative dicarboxyamino acids and SH—containing amino acids, will be readily apparent to those skilled in the art. The above described moiety is preferred only in that it can be conveniently synthesized by those having ready access to solid phase peptide synthesis.

One embodiment to achieve the simultaneous cleavage of coding moieties provides that every coding moiety is an $\alpha$-amino acid, attached as an N-terminal amino acid with its amino group free. The backbone of such a coding structure can be constructed from diamino carboxylic acids (Daa) dicarboxy amino acids or other trifunctional subunits. The amino groups of these amino acids are acylated by the N-protected amino acids used for the coding. Acylation is performed using a mixture of the moieties defined as the code for the given subunit and its position in the test compound. As illustrated in Scheme XIC, infra, the positional chemistry of the reactions of the diamino carboxylic acids need not be specified. The polymer and the coding moieties may be coupled to either of the amino groups of the diamino acids that form the coding molecule polymer.

In the case of the substituted diamino carboxylic acids described in Example 13, infra. and illustrated the coupling reactivities were independent of side chain substitutions. However, should other coding subunits be used, there are two methods which can achieve equimolar incorporation of the coding moieties even though they may have significantly different reactivities, e.g., alanine and isoleucine. The first method is based on compensating the differences in reactivity by using a higher concentration of the slower reacting amino acid (e.g., Eichler J. & Houghten, R., 1993, Biochemistry 32: 11035; Rutter U.S. Pat. No. 5,010,175). Alternatively, a subequimolar amount of the mixture can be used repetitively so that even though one moiety might react faster, sufficient coupling sites remain for the slower reacting amino acid to couple, until after sufficient repetitions of coupling all the reactive sites are consumed. Andrews et al., 1994, *TECHNIQUES IN PROTEIN CHEMISTRY*, 5: 485–492.

There are several basic strategies for the construction of a coding molecule as described above. Two of them are illustrated in scheme XIA. The first is based on the use of the Alloc protecting group (Loffet A. & Zhang H., 1993, Int. Pep. & Prot. Res. 42: 346); (Stevens & Watanabe, 1950 J. Am. Chem. Soc. 72: 725); (Guibe, F. & Saint M'Leux Y., 1981, Tet. Lett. 21: 3591) for building the coding structure and the Fmoc or Fmoc-like group (Carpino & Han, 1972 J. Org. Chem. 37: 3404) for the protection of functional groups on the test compound. In this case the Boc group can be used as the permanent protecting group for both the test compound synthesis and coding synthesis. It is advantageous to use preformed coding subunits of the general form of "block A" depicted in scheme XIA. Alternatively, if preformed coding subunits are not used, another level of orthogonality is required during synthesis. This can be achieved by using Alloc/Ddz protected diamino carboxylic acids for building the coding backbone, since the Ddz group is selectively cleavable by 2% trifluoroacetic acid in dichloromethane (Birr C., et al., 1972, Liebig's Ann. Chem. 763: 162–73). However, this approach is complicated by the need to compensate for different coupling reactivities of the coding amino acids attached as a mixture. A second strategy is based on the use of a combination of Fmoc and Boc groups for temporary orthogonal protection of functional groups in the test compound and coding molecules, and the use of benzoxycarbonyl (Z) or Z-like groups for permanent protection. The coding subunit can be built during the synthesis using Fmoc/Dde (or Fmoc/Alloc, or Fmoc/Ddz) protected diamino carboxylic acids since the Dde group is cleaved by a solution of hydrazine in dimethylformamide and is stable under conditions used for removal of the Boc or Fmoc group (Hone, N. D. et al., Poster P63 at 22nd Eur. Pept. Symp., Interlaken, Switzerland, September 1992).

An alternative approach for the coding is illustrated in Scheme XIB. In this case, a fraction of the amino groups available for coding are acylated by the coding mixture and the remaining amino groups are reprotected by an orthogonally cleavable group (e.g. Alloc) before the next step of randomization is performed. In this scheme it is advantageous to couple the coding mixture prior to the test compound subunit since the deprotection of Alloc can be performed in the recombined stage.

A third alternative embodiment is provided by Scheme XIC. In this scheme, the coding elements need not be preformed with a backbone diaminocarboxylic acid, as in Scheme XIA, nor need there be repetitive blocking and deblockings as in Scheme XIB. The scheme provides an Fmoc-protected test compound and an Alloc-protected coding molecule, with both cooding and test compound reactive groups permanently protected during synthesis with Boc. The coding molecule is synthesized by the sucessive steps of removing Alloc protection of both the $N^\alpha$ and $N^\epsilon$ functionalities of the lysine; addition and coupling of a mixture of coding elements Boc-Caa$_{11}$ and Boc-Caa$_{12}$, each in the amount of 0.5 equivalent, addition and coupling of 1.0 equivalent of Alloc-Lys(Alloc). Note that in this embodiment the coding elements, i.e., the Boc-Caa's, may couple to either the $N^\alpha$ and/or the $N^\epsilon$ of any particular lysine in the coding molecule backbone. Nonetheless neither the stereochemistry nor stoichiometry of the coupling effects the operability of the embodiment because for all purposes of the invention the $N^\alpha$ and $N^\epsilon$ functionalities of lysine are equivalent.

Yet another alternative embodiment of the invention encompasses the reading of a non-sequential code by mass-spectroscopy. The coding molecules are released from the solid phase support by specific cleavage of a linker. The molecules can be further fragmented by electro/spray or ionic bombardment and the individual coding moieties identified by their molecular weights.

Those skilled in the art will appreciate that the use of mass spectroscopy to read a non-sequential code implies that the coding moieties may be linked to the coding molecules by a variety of chemical bonds other than those susceptible to specific degradation, such as peptide bonds.

Schemes XIA, XIB and XIC follow:

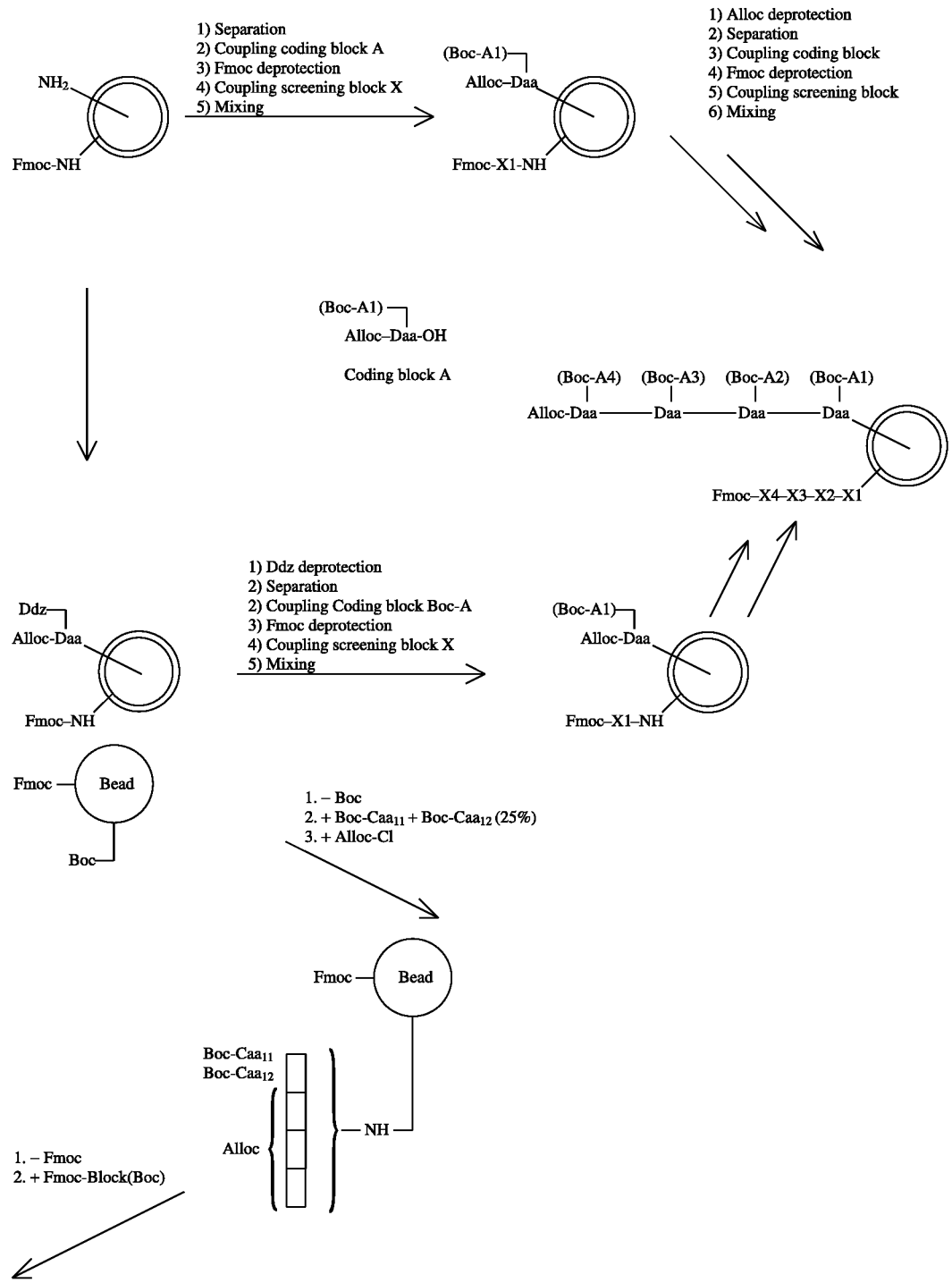

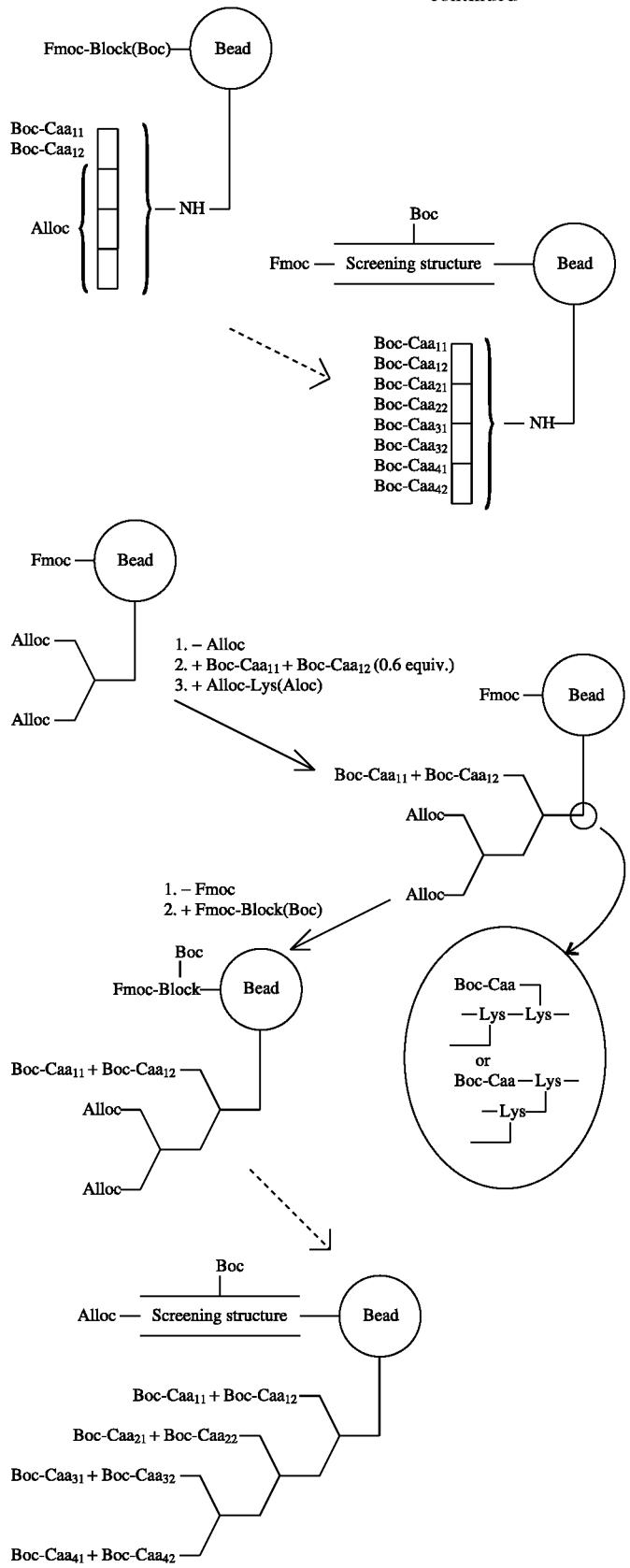

5.7.3 Non-Coded Libraries

For the analysis of the structure of ligands selected from libraries which do not contain coding molecules, the technique used to analyze the structure of coding peptides (described above) may be used when applicable. Alternatively, mass spectrometry particularly using techniques described in U.S. application Ser. No. 07/939,811 filed Sep. 3, 1992, or other analytical techniques (thin layer chromatography, HPLC, NMR, IR, elemental analysis, and the like) can be used to determine the structure of a synthetic test compound selected according to the present invention.

5.8 Therapeutic and Diagnostic Agents From Libraries of Synthetic Test Compound Once the structure of a selected ligand is determined, a large amount of the compound may be synthesized chemically or biologically for confirmation of the results of the structural and screening experiments and other studies. Once a molecular structure of interest has been identified through library screening and structural analysis of active ligands, the present invention provides molecules that comprise the molecular structure for use in treatment or diagnosis of disease. The molecule identified through screening alone may provide a diagnostic or therapeutic agent, or may be incorporated into a larger molecule. A molecule comprising a structure with biological or binding activity may be termed an "effector molecule." The invention further provides libraries for use in various applications. The "effector" function of said effector molecule may be any of the functions described herein or known in the art.

The method described herein not only provides a new tool to search for specific ligands of potential diagnostic or therapeutic value, but also provides important information on a series of ligands of potentially vastly different structure which nonetheless are able to interact with the same acceptor molecule. Integrating such information with molecular modeling and modern computational techniques is likely to provide new fundamental understanding of ligand-receptor interactions.

The therapeutic agents of the invention comprise effector molecules that will bind to the biologically active site of cytokines, growth factors, or hormonal agents and thereby enhance or neutralize their action, and that will block or enhance transcription and/or translation.

The therapeutic agents of the invention include, for example, effector molecules that bind to a receptor of pharmacologic interest such as growth factor receptors, neurotransmitter receptors, or hormone receptors. These effector molecules can be used as either agonists or antagonists of the action of the natural receptor ligand.

Another application of effector molecules that bind to receptors would be to use the binding to block the attachment of viruses or microbes that gain access to a cell by attaching to a normal cellular receptor and being internalized. Examples of this phenomenon include the binding of the human immunodeficiency virus to the CD4 receptor, and of the herpes simplex virus to the fibroblast growth factor receptor. Effector molecules that occupy the receptor could be used as pharmacologic agents to block viral infection of target cells. Parasite invasion of cells could be similarly inhibited, after suitable effector molecules were identified according to this invention.

In another embodiment, an effector molecule comprising a structure that binds to an acceptor molecule of interest may be used to target a drug or toxin. In a preferred embodiment, the acceptor molecule of interest is a receptor or antigen found on the surface of a tumor cell, animal parasite, or microbe, e.g., bacterium, virus, unicellular parasite, unicellular pathogen, fungus or mold. In another embodiment, the targeted entity is an intracellular receptor.

In addition, it is possible that a few of the millions of synthetic test compound molecules in the pool may provide structures that have biological activity. One may isolate molecules that possess antitumor, anti-animal parasite, or antimicrobial, e.g., anti-weed, anti-plant parasite, antifungal, antibacterial, anti-unicellular parasite, anti-unicellular pathogen, or antiviral activities. In addition some of these ligands may act as agonists or antagonists of growth factors, e.g., erythropoietin, epidermal growth factor, fibroblast growth factor, tumor growth factors, to name but a few, as well as hormones, neurotransmitters, agonists for the receptors, immunomodulators, or other regulatory molecules.

The therapeutic agents of the invention also include effector molecules comprising a structure that has a high affinity for drugs, e.g., digoxin, benzodiazepam, heroine, cocaine, or theophylline. Such molecules can be used as an antidote for overdoses of such drugs. Similarly, therapeutic agents include effector molecules that bind to small molecules or metal ions, including heavy metals. Molecules with high affinity for bilirubin will be useful in treatment of neonates with hyperbilirubinemea.

In general, the present invention envisions providing methods to identify molecules for therapy of diseases or illnesses such as are listed in the Product Category Index of The Physicians Desk Reference (PDR, 1993, 47th Edition, Medical Economics Data: Oradell, N.J., pp. 201–202). For example, an effector molecule with anti-cancer, antiparasite, anticoagulant, anticoagulant antagonist, antidiabetic agent, anticonvulsant, antidepressant, antidiarrheal, antidote, antigonadotropin, antihistamine, antihypertensive, antiinflammatory, antinauseant, antimigraine, antiparkinsonism, antiplatelet, antipruritic, antipsychotic, antipyretic, antitoxin (e.g., antivenin), bronchial dilator, vasodilator, chelating agent, contraceptive, muscle relaxant, antiglaucomatous agent, or sedative activity may be identified.

The therapeutic agents of the invention may also contain appropriate pharmaceutically acceptable carriers, diluents and adjuvants. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the patient. While intravenous injection is a very effective form of administration, other modes can be employed, such as by injection, or by oral, nasal or parenteral administration.

A molecule comprising a structure determined according to this invention may also be used to form diagnostic agents.

The diagnostic agent may also be a molecule comprising one or more structures identified as a result of library screening, e.g., more than one polyamide sequence or polyalkane sequence. In addition, the diagnostic agent may contain any of the carriers described above for therapeutic agents.

As used herein, "diagnostic agent" refers to an agent that can be used for the detection of conditions such as, but not limited to, cancer such as T or B cell lymphoma, and infectious diseases as set forth above. Detection is used in its broadest sense to encompass indication of existence of condition, location of body part involved in condition, or indication of severity of condition. For example, a peptide-horseradish immunoperoxidase complex or related immunohistochemical agent could be used to detect and quantitate specific receptor or antibody molecules in tissues, serum or body fluids. Diagnostic agents may be suitable for use in vitro or in vivo. Particularly, the present invention will provide useful diagnostic reagents for use in immunoassays, Southern or Northern hybridization, and in situ assays.

In addition, the diagnostic agent may contain one or more markers such as, but not limited to, radioisotope, fluorescent tags, paramagnetic substances, or other image enhancing agents. Those of ordinary skill in the art would be familiar with the range of markers and methods to incorporate them into the agent to form diagnostic agents.

The therapeutic agents and diagnostic agents of the instant invention may be used for the treatment and/or diagnosis of animals, and more preferably, mammals including humans, dogs, cats, horses, cows, pigs, guinea pigs, mice and rats. Therapeutic or diagnostic agents may also be used to treat and/or diagnose plant diseases.

The diseases and conditions amenable to therapy or diagnosis with molecules discovered according to the present invention are as varied and wide-ranging as the permutations of structures in a library.

In another embodiment, low affinity-binding beads may be selected, and a limited library prepared based on the structure of the ligands on the beads. In another embodiment, a custom low affinity or high affinity support comprising one or a few ligands identified from the millions of synthetic test compound provided by the invention may be used in chromatographic separations.

The invention will be further clarified by the following examples, which are intended to be purely exemplary of the invention.

6. EXAMPLE: A MODEL ENCODED LIBRARY

The present Example demonstrates that two molecules, a "synthetic test compound" and a "coding molecule", can be prepared simultaneously on a single resin bead. Furthermore, a library of such compounds can be prepared, in which each resin bead in the library contains a single species of the "synthetic test compound" and a single species of "coding molecule". In this example, they are present in a 2:1 molar ratio, respectively. The sequence of the "coding molecule" corresponds to the sequence of the "synthetic test compound".

For this model system, both the "synthetic test compound" and the "coding molecule" were peptides. Parallel synthesis of the test peptide and the coding peptide proceeded with use of orthogonal blocking groups Boc and Fmoc.

6.1 Materials and Methods

Solid phase synthesis was performed manually in polypropylene syringes as described by Krchnak and Vagner (1990, Peptide Res. 3: 102–193). Syntheses were performed on TentaGel (TG) (Rapp Polymere, Tubingen, Germany, 130 or 80 μm, 0.23 mmol/g) modified with SCAL handle (Patek and Lebl, 1991, Tetrahedron Lett. 32: 3891–3894) (safety-catch amide linker), or with an appropriate linker. Cleavages of Fmoc protecting groups were carried out with 50% piperidine/DMF for 1×10 min. The Boc protecting group was cleaved with 30% TFA/DCM containing 3% of anisole for 20 min. A solution of DIEA/DCM (10%) was used for neutralization after Boc cleavage. A mixture of BOP/HOBt/DIEA (1:1:2 eq) in DMF was used for activation of both Nα-Fmoc and Boc amino acids. The completeness of each condensation reaction (1.5–40 hrs) was checked by ninhydrin test or by chloranil test in the cases of coupling to secondary amino groups. The coupling protocol included washing with DMF (6–8 times) (followed by washing with DCM in case of Boc protected amino acids) between coupling and deprotection and between deprotection and coupling. Reduction of SCAL linker was performed by 20% $(EtO)_2P(S)SH$ in DMPU for 2 hours. Final cleavage was done by 95% TFA—5% water mixture.

Commercial-grade solvents were used without further purification. Protected amino acids were obtained from Bachem (Torrance, Calif.), Advanced ChemTech (Louisville, Ky.), or Propeptide (Vert-le-Petit, France).

6.2 Results

6.2.1 Synthesis of Model Library and Deprotection of Both Protecting Groups Boc-Lys(Fmoc)-OH was coupled as a first amino acid to SCAL-TG, the Nε-Fmoc group was deprotected and Fmoc-Lys(Fmoc)-OH was coupled to the side chain of the first lysine. Nα- and Nε-Fmoc groups of lysine were cleaved and the resin was divided into three parts. Fmoc-Ala-OH, Fmoc-Phe-OH and Fmoc-Val-OH, respectively, were coupled to each portion of the resin. Corresponding Boc amino acids (Gly, Tyr and Leu-Boc-Tyr-OH was used with unprotected hydroxyl group) were coupled in the next step to the α-amino group of lysine after Boc deprotection, while the "Fmoc branch" was left protected. After the completion of Boc amino acids condensations, all three portions of the resin were combined and the "Fmoc branch" was deprotected. The following randomization was performed exactly the same way as the first one after the splitting of the resin into the three equal portions. After randomization of three positions (coupling of three different amino acids in each position), the resin was divided into separate portions for subsequent analysis.

Two completely deprotected beads selected at random were separately submitted for sequence analyses. Correct "complementary" amino acids were found in all three cycles in the expected ratio of 2:1. Results (values in pmoles): 1st bead: 1st cycle: V 251, L 146, 2nd cycle: V 244, L 147, 3rd cycle: V 245, L 119; 2nd bead: 1st cycle: A 102, G 39, 2nd cycle: V 121, L 59, 3rd cycle: F 125, Y 50.

Part of the resin (about 100 mg) was treated with 20% diethyldithiophosphate in DMPU (2×1 h shaking) to reduce the SCAL handle. The mixture of peptides was cleaved from the reduced SCAL with $TFA/H_2O$ (95:5) for 1 h. The cleavage mixture was concentrated in vacuo and precipitated with $Et_2O$. The precipitate was collected by centrifugation and dried. The mixture of peptides was dissolved in 0.1% $TFA/H_2O$ and analyzed by HPLC. A slow gradient of 0–50% acetonitrile and 0.1% TFA over 200 min eluted the expected 27 peaks. Several additional minor peaks were identified, the formation of which was attributed to the use of side chain unprotected tyrosine during the synthesis. Since the danger of elimination (or at least decreasing the content) of some sequences by ether precipitation existed, the second cleavage of the mixture avoided this step. The cleavage mixture of TFA and water was diluted by additional water, concentrated on an evacuated centrifuge and lyophilized. HPLC evaluation of the mixture demonstrated roughly equimolar representation of all expected peaks.

6.2.2 Deprotection of N-Terminal FMOC Group and Acetylation of the "FMOC Branch"

Deprotection of the Fmoc group was followed by acetylation of free N-terminal amino groups. Acetylation was performed with a 0.3M solution of N-acetylimidazole in DMF for 20 min (ninhydrin test negative). N-terminal Boc groups on the other branch were deprotected after acetylation. Three randomly chosen beads were sequenced and provided the following readings (values in pmoles): 1st cycle: Y 213 (bead 1), G 161 (bead 2), Y 201 (bead 3), 2nd cycle: L 165 (1), Y 166 (2), Y 205 (3), 3rd cycle: Y 188 (1), L 128 (2), G 162 (3). The readings were not contaminated by the amino acids present in the acetylated arm.

A part of the acetylated beads (about 100 mg) were treated as described above (precipitation of the mixture by ethyl ether and/or evaporation of cleavage mixture and lyophilization) to reduce the handle and cleave the acetylated peptides. HPLC analysis under the same conditions have shown that during ether precipitation a significant proportion of the library was lost due to its solubility in ether. Evaporated and lyophilized sample provided the same number of peaks of approximately the same pattern as in the case of the deprotected library, although retention times shifted to higher values due to acetylation of the Fmoc "branch".

6.2.3 Replacement of the BOC Protecting Group with the TFA Group

The trifluoroacetyl group replaced the Boc group at the N-terminus in order to permit a stepwise sequencing experiment. First, the N-terminal Boc group was cleaved from a resin sample (50 mg) while the "Fmoc branch" was left protected. The free amino groups were protected with trifluoroacetyl by treatment with 10 equivalents (0.14 mmol, 21 µl) of trifluoroacetic acid anhydride in dichloromethane (0.5 ml) in the presence of DIEA (0.16 mmol, 28 µl). The reaction was complete after 1h (ninhydrin test negative). After the trifluoroacetylation, Fmoc group on the other branch was removed and three beads were submitted for sequencing. The sequence of the Fmoc branch was determined. After sequencing the Fmoc branch, the bead that was sequenced was removed from the sequencer, and the bead was treated with a 0.2M solution of NaOH (3 h, 20° C.), dried, and submitted for an additional three cycles of sequencing. The appropriate sequences of the Boc branch predicted from the sequencing of the Fmoc branch were obtained. 1st bead (values in pmoles): 1. F (735), 2. V (643), 3. A (837); after TFA removal: 1. Y (207), 2. L (187), 3. G (76), sequence FVA/YLG; 2nd bead: 1. A (215), 2. A (230), 3. F (193), after TFA removal: 1. G (88), 2. G (86), 3. Y (80), sequence AAF/GGY; 3rd bead: 1. F (63), 2. F (67), 3. V (41); after TFA removal: 1. Y (15), 2. Y (12), 3. L (4), sequence FFV/YYL.

6.2.4 Cleavage of a Peptide From One Bead

Several beads of resin containing fully deprotected sequences on the reduced SCAL handle were placed separately into small glass vials and treated overnight with 30 µl of neat TFA. Aliquots (3 µl) were withdrawn and diluted with H$_2$O to the total volume of 20 µl and analyzed by HPLC on microbore HPLC (Michrom apparatus) (gradient 5–60% acetonitrile in 0.1% TFA in water over 20 min). Calculations based on the average extinction coefficient of peptides at 215 run have shown that about 100–200 pmoles of peptide was released from one polymeric bead.

6.3 Discussion

The model encoded library is illustrated in FIG. 2. A branching linker attaches the synthetic test compound peptide and the coding peptide to the solid phase support. Generally, the synthetic test compound can be a compound that does not undergo Edman degradation, thus the sequence information from the coding sequence provides for structure determination of the test compound. Each of the subunits of the synthetic test compound is unambiguously associated with an amino acid in the coding arm, in a position-specific fashion, thus allowing structure analysis.

Several approaches to building the coding sequence exist. One procedure (FIG. 1A) uses a statistical distribution of both structures on the polymeric bead. In this case, any possible ratio can be achieved, and the possibility of producing a cooperative effect of both sequences can be minimized. In the second procedure (FIG. 1B), both screening and coding structures are built on the branched attachment to the solid support, realized for example by a diamino carboxylic acid (lysine). Both "sequences" are present in the defined molar ratio and a defined special arrangement accessible to the acceptor molecule being screened. In the applications where the release of the screened peptide into solution is used, the localization of screening and coding compound on the bead is of no concern, since due to the use of different linkers, the coding sequence is never released into the solution.

A simple scheme was pursued to conclusively demonstrate the chemical synthesis of synthetic test compound and coding sequences. A "synthetic test compound" was built from A, F and V. These amino acids were encoded with G, Y and L respectively in the "coding" sequence. The synthetic test compound were built on "test" branches, i.e., both amino groups of lysine attached on another lysine side chain using Fmoc chemistry (see FIG. 2). Resin was split into three parts and Nα-Fmoc protected amino acids were coupled on the test branches and left in the protected state. The corresponding Nα-Boc (coding) amino acids were coupled on the encoding branch. All resin support was mixed together and divided again into three parts. Deprotection of the Nα-Fmoc group and coupling of the subsequent Nα-Fmoc amino acid was performed in the presence of Boc protection on the other branch. The Boc protecting group is stable under those conditions. In the next step, the Nα-Boc group was cleaved and the Nα-Boc amino acid corresponding to the Fmoc amino acid coupled to the test branch was coupled on the coding branch in each reaction. The procedure of mixing, splitting and separate coupling of Fmoc and Boc amino acids was repeated once more. The synthesis was performed on a SCAL handle, which is stable under conditions of both Boc and Fmoc strategies. This handle can, however, be cleaved under relatively mild acidolytic conditions after reduction of its sulfoxide moieties (Patek and Lebl, 1991, Tetrahedron Lett. 32: 3891–3894).

Sequencing of beads prepared in this manner demonstrated a molar ratio of 2:1 of screening to coding sequence and the appropriate correspondence of particular amino acids (FIG. 2A). Using one aliquot of beads, the "screening" sequence was acetylated and clean sequence reading was obtained from the "coding" sequence (FIG. 2B). Using a different aliquot of beads, the "coding" sequence was blocked by a trifluoroacetyl group, sequencing of the "screening" branch was performed, the trifluoroacetyl group was cleaved from the sequenced beads and the sequence of the "coding" peptide was determined, confirming the results from the sequencing of the "screening" peptide (FIG. 2C).

To verify that the synthetic strategy generates the predicted equimolar ratio of defined number of structures, the "minilibrary" represented in an aliquot was cleaved from the support. Reversed phase HPLC confirmed the presence of 27 different peptides. The peaks identified in the trace were collected and submitted for sequence analysis, which confirmed the purity of each peptide and its composition. Cleavage of peptides was also performed from the single beads and the feasibility of analysis of peptides released from only one bead was confirmed.

7. EXAMPLE: NON-PEPTIDE LIBRARIES CODED BY A PEPTIDE STRUCTURE

This Example demonstrates that a peptide coding molecule can unambiguously encode a non-peptidyl test compound when each is synthesized in parallel on a single bead. In this Example, the subunits of the test compound have been chosen so that each compound has a unique molecular weight. Comparing the observed molecular weight of the test compound to the sequence of the coding peptide shows that a coding peptide codes for one test compound.

7.1 Materials and Methods

Couplings of amino acids were performed by a manual method using standard protocol at room temperature; protected amino acid (3 eq) in DMF was mixed with DIC (3 eq), or DIC and HOBT (3 eq each) with the resin and coupling was followed by analytical tests. Symmetric anhydrides were used where specified.

The subunits used to prepare the non-peptide library are shown in Scheme XII:

SCHEME XII

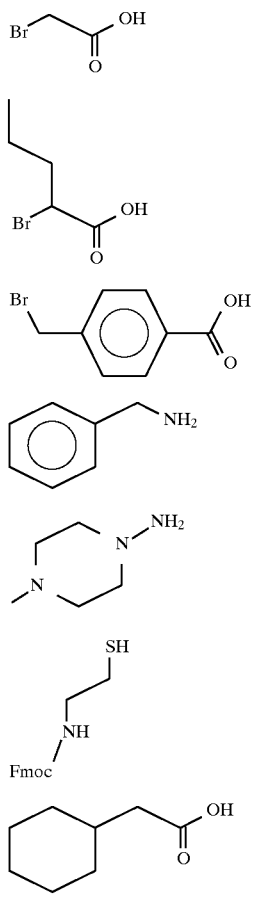

-continued
SCHEME XII

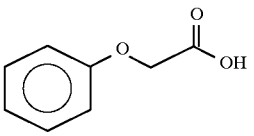  8

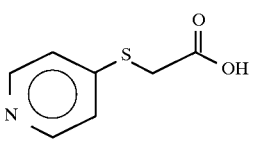  9

Fmoc-SCAL linker and Boc-Lys(Fmoc) were coupled first to the resin (TentaGel S $NH_2$, 1 g) using DIC and HOBT. After cleavage of the Fmoc group, Fmoc-Trp was coupled and the new Fmoc group was deprotected. The peptide-resin was divided into three equal portions, and three different bromoacids (one in each reaction vessel, 3 eqs each) were coupled by the use of DIC in DMF (3 eqs). The three acids were α-bromoacetic, α-bromovaleric and bromotoluic acid. The coupling of the last acid was repeated because of its low reactivity, using a 6 fold excess of both acid and DIC. Boc protection of the a-amino group of Lys was removed by TFA and the first coding sequence Boc-protected amino acids (Gly, Ala, Leu) were coupled by DIC. Coding amino acids were chosen according to the molecular weight of the non-peptide building blocks, so the lightest block (bromoacetic acid in this case) was coded by Gly, the heaviest one (bromotoluic) was coded by Leu and medium one (α-bromovaleric) was coded by Ala.

The three resin parts were pooled together, washed thoroughly with DCM and deprotected by TFA/DCM in preparation for the coupling of the next coding amino acids. After deprotection, the resin was divided again into three portions. Couplings of Boc-protected amino acids (again Gly, Ala and Leu) were performed as usual by means of DIC. After coupling the coding peptide amino acids, the non-peptidyl subunits were added. Two parts of the resin were treated with 2M solutions of amines (benzylamine and 1-amino-4-methylpiperazine) in DMF overnight. The third part was treated with 2M solution of fluorenylmethyloxycarbonylaminoethylthiol, and after the completion of the reaction the Fmoc group was removed. Coding of amines was based again on their molecular weights.

The resin was pooled together once more, mixed and divided into three portions for the final couplings. Carboxylic acids (cyclohexylacetic acid, phenyloxyacetic acid and 4-pyridylthioacetic acid) were coupled to the amines obtained (primary and secondary) by DIC and the coupling reactions were repeated twice using preformed symmetrical anhydrides in 3–5 fold excess. After obtaining a negative chloranil test, the three batches of resin were treated separately by TFA, neutralized, and the last coding Boc-protected amino acids were coupled using DIC and HOBT. Coding of the last carboxylic acids was based on the same scheme as before. Finally all the resin was pooled together.

Fast atom bombardment (FAB) mass spectroscopy measurements were carried out on a ZAB EQ spectrometer (VG Analytical Ltd, Manchester, UK). $^1H$ NMR spectra were obtained on a General Electric QE 300 instrument. Sequencing by Edman degradation was performed on an ABI 4778 protein sequencer (Applied Biosystems, Foster City, Calif.) and Porton PI 3010 instrument (Porton Instruments, Tarzana, Calif.). Both analytical and preparative HPLC were carried out on a Waters 625 LC system with a Waters 490E Programmable Multiwavelength Detector using Vydac Peptide and Protein C18 analytical (0.46×250 mm, 5 µm, 1 ml/min) and preparative (10×250 mm, 10 µm, 3 ml/min) columns, respectively. Analyses of mixtures released from one bead were performed on an Ultrafast Microprotein Analyzer (Michrom BioResources, Pleasanton, Calif.) using a Reliasil C18 column (5 µm, 300 A, 1×150 mm). All spectra are reported in ppm relative to tetramethylsilane (δ) using either $CDCl_3$ or $CD_3SOCD_3$ as solvents. UV/VIS absorption spectra were recorded on a Hewlett Packard HP 8452A Diode-Array spectrophotometer using a 1-cm quartz cuvette. Amino acid analyses were carried out on a D-500 system (Durrum Corp., Palo Alto, Calif.) system.

7.2 Results 7.2.1 Synthesis of Two Forms of Encoded Library

Two formats for the libraries have been completed using this general approach. The only difference between those two is the location of the SCAL linker as shown in Scheme XIII.

SCHEME XIII

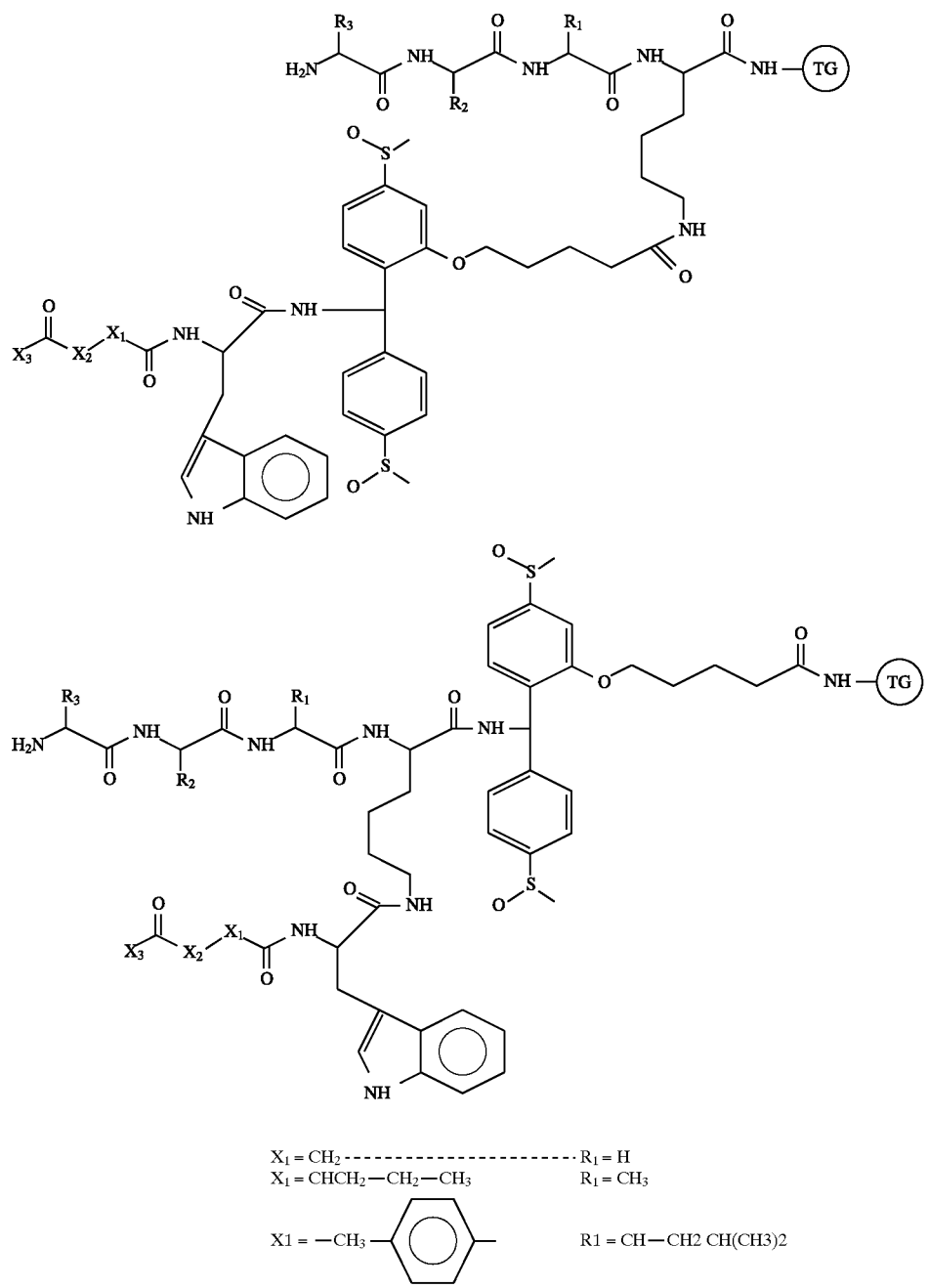

-continued
SCHEME XIII

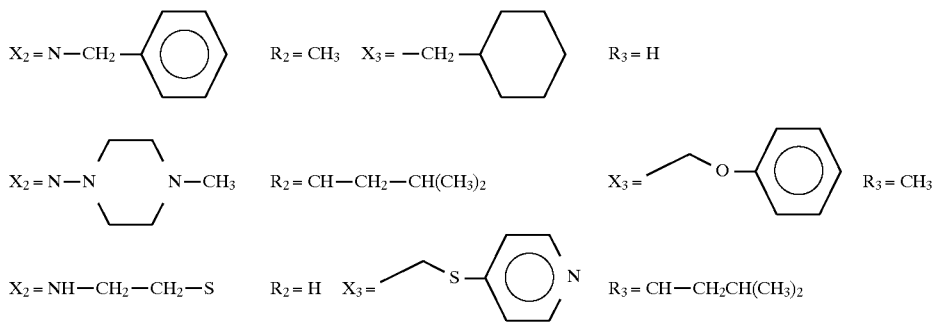

The first library (A) contained the SCAL linker on the N-ε of Lys, which was attached directly to resin, and therefore Trp-amide was the last amino acid in all the compounds of this library. In this library, coding peptides remained on beads of resin after cleavage. In the second library (B) the SCAL linker was attached to the resin, and the last amino acid in all compounds was Lys. Each of the compounds released from this library included the synthetic compound and coding sequence peptide.

The non-amino acid building blocks used to construct the synthetic test compound are shown above in Scheme XII. These building blocks were chosen to form unique molecular weight test compounds. The test compounds, molecular weights and coding sequences are shown in Table 1.

TABLE 1

Combination of Building Blocks Used in the Construction of a Model Nonpeptide Library

| Combination | M.W. No Coding | M.W. With Coding* | Coding Sequence |
|---|---|---|---|
| 167 | 444.6 | 743.9 | GGG |
| 168 | 454.5 | 767.9 | AGG |
| 169 | 471.6 | 827.0 | LGG |
| 147 | 474.6 | 787.9 | GAG |
| 148 | 484.5 | 811.9 | AAG |
| 149 | 501.6 | 871.1 | LAG |
| 157 | 482.6 | 838.0 | GLG |
| 158 | 492.6 | 862.0 | ALG |
| 159 | 509.6 | 921.2 | LLG |
| 267 | 486.7 | 800.0 | GGA |
| 268 | 496.6 | 824.0 | AGA |
| 269 | 513.7 | 883.1 | LGA |
| 247 | 516.7 | 844.1 | GAA |
| 248 | 526.6 | 868.0 | AAA |
| 249 | 543.7 | 927.2 | LAA |
| 257 | 524.7 | 894.1 | GLA |
| 258 | 534.7 | 918.1 | ALA |
| 259 | 551.7 | 977.3 | LLA |
| 367 | 520.7 | 876.1 | GGL |
| 368 | 530.6 | 900.1 | AGL |
| 369 | 547.7 | 959.2 | LGL |
| 347 | 550.7 | 920.1 | GAL |
| 348 | 560.6 | 944.1 | AAL |
| 349 | 577.7 | 1003.3 | LAL |
| 357 | 558.7 | 970.2 | GLL |
| 358 | 568.7 | 994.2 | ALL |
| 359 | 585.7 | 1053.3 | LLL |

*M.W. of branched compound containing the test compound and the coding peptide.

Beads from the first library (Scheme XIII, Upper Panel) were treated with reducing agent and individual beads were picked up for separate cleavage and sequence analyses. Five beads were studied. After cleavage of the non-peptide part, the beads were successfully sequenced (see Table 2) and the structure of the non peptide compound could be deduced. Solutions containing the cleaved compounds were analyzed on micro HPLC system.

TABLE 2

Structures Contained on Randomly Selected Beads From a Library of Non-peptide Structures

| | Sub-unit | | Amino Acid Detected (pmol) | | |
|---|---|---|---|---|---|
| Bead No. | Combination | M.W. (m/z) | 1st Cycle | 2nd Cycle | 3rd Cycle |
| 1 | 149 | 501.6 | L (50) | A (55) | G (72) |
| 2 | 169 | 471.6 | L (34) | G (31) | G (29) |
| 3 | 258 | 534.7 | A (101) | L (83) | A (98) |
| 4 | 147 | 474.6 | G (45) | A (41) | G (25) |
| 5 | 157 | 444.6 | G (39) | G (30) | G (22) |

A sample (800 mg) of the second library (Scheme XIII, Lower Panel) was treated with 95% TFA after reduction of the SCAL linker, freeze-dried, dissolved in water, and separated on a semi-preparative HPLC column to 44 peaks using a gradient of 0–60% acetonitrile in 0.1% TFA in water over 200 min. Fractions were lyophilized and several peaks were analyzed by FAB MS and sequencing to show the correspondence between the structure predicted from the amino acid coding sequence and the molecular weight of the construct. Examples of peaks chosen at random for further analysis follows: Peak 4: RT 25.31 min, sequencing: 1. Leu (364 pmol), 2. Gly (139), 3. Gly (422); FAB MS—827.0 (building block combination 169); Peak 8: RT 28.69 min, sequencing: 1. Gly (261), 2. Leu (176), 3. Ala (225); FAB MS—770.2 (building block combination 257 w/o block 7); Peak 13: RT 31.47 min, sequencing: 1. Leu (792), 2. Leu (551), 3. Gly (128); FAB MS—921.0 (building block combination 159); Peak 14: RT 32.27 min, sequencing: 1. Leu (7930), 2. Gly (1810), 3. Ala (1763); FAB MS—883.0 (building block combination 269); Peak 15: RT 32.77 min, sequencing: 1. Leu (784), 2. Ala (447), 3. Ala (360); FAB MS—776.2 (building block combination 249 w/o block 9); Peak 16: RT 33.16 min, sequencing: 1. Leu (1286), 2. Ala (918), 3. Ala (688); FAB MS—776.2 (building block combination 249 w/o block 9); Peak 17: RT 33.51 min, sequencing: 1. Leu (298), 2. Leu (280), 3. Ala (202); FAB MS—826.2 (building block combination 259 w/o block 9); Peak 19: RT 34.80 min, sequencing: 1. Leu (641), 2. Gly (412), 3. Ala (460); FAB MS—883.1 (building block combination 269); Peak 20: RT 36.66 min, sequencing: 1. Leu (150), 2. Leu (119), 3. Leu (80); FAB MS—902.2 (building block combination 359 w/o block 9); Peak 26: RT 41.77 min, sequencing: 1. Gly (39), 2. Gly (38), 3. Gly (23); FAB MS—744.1 (building block combination 167); Peak 31: RT 48.86 min, sequencing: 1. Ala (180), 2. Gly (98), 3. Ala (106); FAB MS—824.0 (building block combination 268); Peak 32: RT 49.46 min, sequencing: 1. Leu (234), 2. Leu (320), 3. Ala (277); FAB MS—826.1 (building block combination 259 w/o block 9); Peak 33: RT 50.70 min, sequencing: 1. Gly (152), 2. Gly (120), 3. Ala (94); FAB MS—800.1 (building block combination 267).

7.2.2 Synthesis of Representative Compounds from the Non-Peptide Library

A component of the first library (A), compound I:

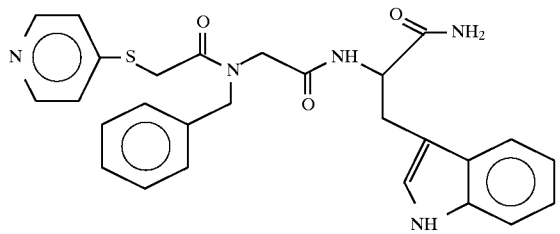

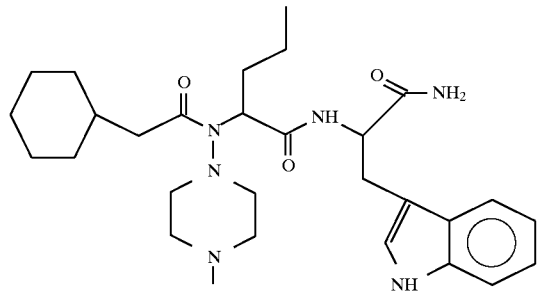

was synthesized according to the same scheme as compound I, using as subunits α-bromovaleric acid (40 μl), 4-methyl-aminopiperazin (100 μl) and cyclohexylacetic acid (80 mg). Formula: $C_{29}H_{44}N_6O_3$, MS expected—524.7, MS found—525.3 $(M+H)^+$, 558.2 $(M+Na)^+$ and 573.2 $(M+K)^+$.

The third component of the first library (A), compound III:

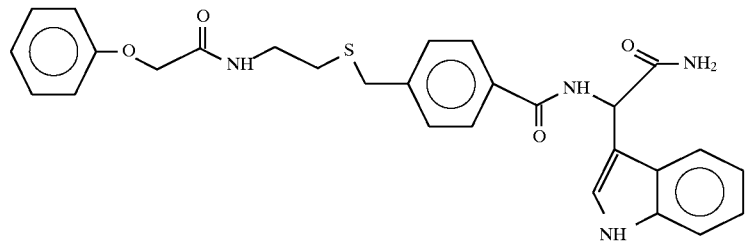

was synthesized on 0.23 g of Knorr resin (0.5 meq/g). Fmoc-Trp was coupled first according to the general protocol, using DIC and HOBT. After deprotection of the amino group, α-bromoacetic acid (50 mg) was coupled using DIC (50 μl) in DMF (0.5 ml). Benzylamine (100 μl) was dissolved in 0.5 ml of DMSO and bromoresin was treated with this solution overnight. Final carboxylic acid, 4-pyridylthioacetic acid (80 mg), was dissolved in 0.85 ml of DMPT and preactivated with DIC (80 μl) and HOBT (80 mg) and coupled to aminoresin for 10 hours. Coupling was repeated using PyBrop and DIEA for activation. Cleavage of the compound I was achieved in 95% TFA. After cleavage, TFA was evaporated in vacuo and the residue was dissolved in 30% aqueous acetonitrile and lyophilized. The product obtained after drying was redissolved in neat acetonitrile and precipitated by ether. This operation was repeated twice and an almost white precipitate was obtained. The product showed two peaks on reverse phase (RP) HPLC. The second peak gave the expected mass-spectrum of compound I. The yield of component I after purification on semipreparative RP HPLC was 18 mg. Formula: $C_{27}H_{27}N_5O_3S$, MS expected 501.6, MS found—502.2 $(M+H)^+$. $^1H$ NMR data (DMSO-d6): 10.804 d (1H, $N^{in}H$); B. 49 d (2H, pyridyl $C_2H$ and $C_6H$); 8.35 d (1H, NH); 7.62 d (2H, pyridyl $C_3H$ and $C_5H$); 6.9–7.7 mm (Bzl and Trp aromatic protons); 4.59 m (1H, Trp $C^αH$); 3.75–4.65 m (aliphatic protons); 3.19 dd and 2.91 dd (2H, Trp $C^βH$).

A second component of the first library (Scheme XII, A), compound II:

was synthesized according to the similar scheme as compound I, using as building stones α-bromotoluic acid (120 mg), fluorenylmethyloxycarbonyl-aminoethylmercaptan (280 mg) (deprotection after coupling with piperidine/DMF) and phenoxyacetic acid (80 mg). Formula: $C_{29}H_{30}N_4O_4S$, MS expected 530.6, MS found–553.0 $(M+Na)^+$.

7.3 Discussion

This example demonstrates the ability to construct non-peptide structures in parallel with the coding sequence. The difference in the libraries was in the placement of the SCAL linker, allowing for the selective cleavage of the product. In the first case, (Scheme XIII Upper Panel), the cleavage of the linker leads to the release of the non-peptide compound $X_3$-$X_2$-$X_1$-Trp (Trp is attached for spectroscopic monitoring purposes) connected to its coding peptidic structure via a lysine moiety. Cleavage of the linker in the second case (Scheme XIII, Lower Panel) leads to the release of the non peptide compound $X_3$-$X_2$-$X_1$-Trp without any attached coding peptide. Construction of the non peptide compound involved (i) attachment of α-bromo substituted carboxylic acid or bromomethylbenzoic acid to the available amino group on the solid carrier, (ii) alkylation of an amino (Zuckerman et al., 1992, J. Am. Chem. Soc. 114: 10646–10647) or thiol group of an amine or N-protected aminomercaptan, and (iii) acylation of a generated amino group by a derivative of carboxylic acid. We have selected the building blocks for this experiment in a manner which permits the assignment of the structure of the constructed screening molecules based solely on the molecular weight of the construct (see Table I). Introduction of every unnatural building block to the screening structure was followed (or preceded) by the coupling of a coding amino acid to the other arm of the molecule. We have used only glycine, alanine and leucine for coding (these amino acids therefore coded a different structural element in every step of the randomization). Assignment of these amino acids to the particular structural element is given in Scheme IX. Alkylation of amines or thiol used in this experiment by 2-bromopentanoic acid attached to the polymeric matrix lead to the generation of compounds with a chiral center, therefore the number of structural combinations is 36 rather than 27. However, only 27 different bead types are generated (with screening sequences of differing molecular weights), 9 of which contain a mixture of diastereoisomeric compounds. To simplify the analysis of the mixtures and to demonstrate the ability to perform this type of synthesis on polymeric carrier, three of the possible structures were resynthesized as individual compounds, using the same chemistry and polymeric support as in the synthesis of the model library.

The generated mixtures were cleaved from the carrier after the reduction of the SCAL linker, and analyzed by reversed phase HPLC. The number of peaks obtained corresponds approximately to the predicted number of 36. Individual peaks from the first type of library were collected. Part of each fraction collected was subjected to Edman degradation and part was analyzed by mass spectroscopy. Results obtained confirm the correlation of sequence determination with molecular weight determination by mass spectroscopy, confirming the viability of the principle of coding by peptide sequence (Table 2).

An alternative analysis was performed on randomly selected beads from the second library. Individual beads were treated with a reducing agent to labilize the SCAL linker and the non peptide structure was cleaved by a TFA/water mixture. After this treatment, the beads were successfully sequenced (see Table II) and the structure of the non peptide compound could be deduced. The cleaved compounds were analyzed on a micro HPLC system.

8. EXAMPLE: LIBRARY: XXXX-Lys(XXXX)-Lys(ZZ)-βAla-Gly-βAla-Gly-TG

The present Example demonstrates the use of a coding peptide to encode a non-sequenable portion of a peptide simultaneously with the sequenable portion of the test compound peptide.

8.1 Materials and Methods

8.1.1 Synthesis of the Library

The library was synthesized according to the following protocol. 1. Coupling of Fmoc-Lys(Boc) to H-βAla-Gly-βAla-Gly-TG SEQ ID NO:1; 2. Fmoc cleavage; 3. Coupling of Fmoc-Lys(Fmoc); 4. Boc cleavage; 5. After division of resin into 9 portions and the following Ddz protected amino acids were coupled in separate reactions: A,D,I,K,M,N,S,T,V; 6. Fmoc cleavage; 7. Coupling of nine Fmoc-protected amino acids: Y,G,F,L,H,P,Q,R,E (Y was coupled to that part of resin that had already attached A, etc.); 8. Resin combined and Ddz cleaved; 9. Repeat steps 5–7; 10. Fmoc cleavage; 11. Coupling of nine Fmoc-protected amino acids: Y,G,F,L,H,P,Q,R,E; 12. Repeat steps 10–11; 13. Fmoc cleavage; 14. Side-chain protecting groups and Ddz removed by mixture K (King et al., 1990, Int. J. Pep. Protein Res. 36: 255–266).

One bead was submitted to four cycles of Edman degradation: 1st cycle: Arg (64), Ile (67); 2nd cycle: Gly (45), Thr (14); 3rd cycle: Phe (42); 4th cycle: Arg (35). Ile was Ddz protected for coupling and found in the first cycle. It coded for Phe, which was detected in the third cycle. In the second cycle Thr was detected as the amino acid that had been coupled Ddz protected. Arg, coded by Thr, was accordingly found in the fourth cycle of sequencing.

8.1.2 Screening Protocol of the Library

The peptide library was screened according to published procedures (Lam and Lebl, 1992, Immunomethods 1: 11–15). The peptide beads were first mixed with double-distilled water to remove the DMF. After extensive washing with PBS (137 mM NaCl, 2.7 mM KCl, 4.3 mM $Na_2HPO_4$, 1.4 mM $KH_2PO_4$, pH 7.2), the beads were coated with 0.05% gelatin (w/v) to block any nonspecific binding. The beads were then incubated with a 1:100,000 dilution of streptavidin-alkaline phosphatase at 2 mg/ml (Pierce; Rockford, Ill.) in 2× PBS/Tween/gelatin (2× PBS, 0.1% Tween-20 (v/v), and 0.05% gelatin (w/v)). The beads were then thoroughly washed with TBS (137 mM NaCl, 2.7 mM KCl, 25 mM Tris base, pH 7.4) and the standard substrate 5-bromo-4-chloro-3-indolyl phosphate was added. The beads, together with the substrate, were then transferred to petri dishes for color development. After 30 minutes to 1 hour, the colored beads were collected, with the aid of a micropipette, washed with 6M guanidine hydrochloride, pH 1.0, and subjected to sequencing as described.

The remaining library of colorless beads were then recycled with 8M guanidine hydrochloride, pH 2.0, thoroughly washed with PBS, and incubated with 60 pM biotinylated anti-β-endorphin (clone 3-E 7, Boehringer Mannheim) in 2× PBS/Tween/gelatin overnight. After thorough washing, streptavidin-alkaline phosphatase was added. One hour later, the beads were washed, substrate was added, and color development proceeded as described above. The color beads were then physically isolated and subjected to sequencing. In these two experiments, only the darkest beads were sequenced.

8.2 Results and Discussion

Sections 6 and 7, supra, show that a "test compound" can be coded by a "coding" peptide sequence. This principle can also be used for determination of the structure of peptides containing a nonsequenceable component within the peptide chain. In this case it is necessary to code only for the amino acid residues located on the carboxyl terminus of the molecule, after the nonsequenceable part. We have constructed a library mimicking this situation, although the "test compound" does not actually contain a non sequenable component. The structure of the library is given in Scheme XIV.

SCHEME XIV

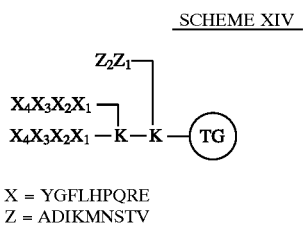

X = YGFLHPQRE
Z = ADIKMNSTV

Amino acid residues $X_4$ and $X_3$, in the "test compound" arm are not coded by any counterpart in the "coding" arm. Amino acids $Z_1$, and $Z_2$ code for residue $X_1$, and $X_2$ and are present in one half the concentration of the amino acids in the "test" sequence. Two cycles of Edman degradation can reveal the structure of the peptide of interest. The amino acid detected in the greater amount is the residue from position 1 or 2 of the "test" sequence. The amino acid detected in lower quantity is the residue coding position 4 or 3 of this sequence. The coding amino acid may be the same as the one for which it is coding, or it can be a different one. The coding and screening set of amino acids used in this example are given in Scheme XIV.

TABLE 3

Sequencing Results

| 1st Cycle | 2nd Cycle | Deduced Sequence | Target |
|---|---|---|---|
| Y,D | G,I | YGGF SEQ ID NO:2 | anti-β-endorphin |
| Y,N | G,I | YGPF SEQ ID NO:3 | anti-β-endorphin |
| Y,D | G,K | YGGL SEQ ID NO:4 (3x) | anti-β-endorphin |
| H,S | P,I | HPQF SEQ ID NO:5 (5x) | streptavidin |

The synthesis of the library was performed with the use of a combination of three amino protecting groups. Temporary protection of the α-amino group in the "screening" sequence was provided by the Fmoc group, which is cleavable by piperidine in dimethylformamide. Temporary protection of the "coding" sequence was achieved by the use of the Ddz group (Birr et al., 1972, Liebig's Ann. Chem. 763: 162–173), cleavable with diluted trifluoroacetic acid (2%). Side chain functional groups were protected by tert-butyl type protecting groups cleavable by trifluoroacetic acid of higher concentration (50%). One cycle of randomization with sequence tagging consisted of (i) division of resin into the number of reaction vessels corresponding to the number of amino acids randomized in this step, (ii) coupling Fmoc protected amino acids (Y, G, F, L, H, P, Q, R, E), (iii) washing, cleavage of Ddz group, and neutralization, (iv) coupling of corresponding Ddz protected amino acids (A, D, I, K, M, N, S, T, V), (v) mixing the solid support and deprotection of the Fmoc group.

This library was used in the screening against two model targets, anti-β-endorphin monoclonal antibody, and streptavidin. Positive beads were identified by the standard staining technique (Lam and Lebl, 1992, Immunomethods. 1: 11–15; Lam et al., 1991, Nature 354: 82–85), and the beads (5 for each target) identified in this screen were subjected to two cycles of Edman degradation. Results of two cycles of Edman degradation are given in Table 3. As can be seen, streptavidin positive beads gave in all cases H ($X_1$) and S ($Z_1$) (coding for Q, $X_3$) in the first cycle, and P ($X_2$) and I ($Z_2$) (coding for F, $X_4$) in the second cycle. Therefore sequence of the screening arm HPQF could be decoded easily. Beads identified in the anti-β-endorphin screening gave more varied results. Besides Y ($X_1$) and D ($Z_1$) (coding for G, $X_3$), N ($Z_1$) (coding for P, $X_3$) was also found in the first cycle, and G ($X_2$) and I ($Z_2$) (coding for F, $X_4$) and K ($Z_2$) (coding for L, $X_4$) were found in the second cycle. Therefore sequences YGGL (3x), YGGF, and YGPF could be constructed from these data. These sequences are in agreement with the data obtained earlier (Lam and Lebl, supra; Lam et al., 1991, supra; Lam et al., 1993, Bioorg. Med. Chem. Lett. 3: 419–429).

These experiments clearly establish that peptides can be used to encode other structures, which are partially or completely unsequenable. This technology will have major significance because of its broad applicability to the study of ligand-acceptor molecular interactions and to drug development. Encoded libraries open the door to applying broad parallel approaches to drug synthesis and screening non-peptide libraries.

9. EXAMPLE: LIBRARIES OF NON-PEPTIDE STRUCTURES BASED ON SOLID PHASE PEPTIDE SYNTHESIS CHEMISTRY

The present Example combines the simplicity of synthesis of peptide structures with the diversity available using alternative subunits besides standard amino acids. The simplest subunits for the library construction are discussed in Section 5.5.9, supra.

Synthesis of the present library involved use of trifunctional amino acids and modification of a side chain to achieve the structural multiplicity. Amino acids like diaminobutyric acid, aspartic acid, cystine and/or iminodiacetic acid are the smallest subunits onto side chains of which carboxylic acids, amines, isocyanates or halides (aliphatic, aromatic, heterocyclic) can be attached. These amino acids can themselves act as a scaffold for further derivatization.

To achieve a reasonable binding to an acceptor (e.g., receptor, antibody, enzyme, nucleic acid, etc.) the appropriate spatial arrangement of the interacting structures must be realized. Linear presentation of amino acid side chains in peptide libraries may not be an optimal format for the selection of the best binding structures. The optimal strategy for displaying the interacting structures may be their placement on a molecular scaffold, which would map the appropriate conformational space. Interrelationships of the same individual building blocks in the scaffolding arrangement can be varied using different scaffolding as well as different side chains.

9.1 Materials and Methods

9.1.1 Instruments

Fast atom bombardment (FAB) mass spectroscopy measurements were carried out on a ZAB EQ spectrometer (VG Analytical Ltd, Manchester, UK). $^1$H NMR spectra were obtained on a General Electric (Fullerton, Calif.) QE 300 instrument. Sequencing by Edman degradation was performed on an ABI 4778 protein sequencer (Applied Biosystems, Foster City, Calif.) and Porton PI 3010 instrument (Porton Instruments, Tarzana, Calif.). Both analytical and preparative HPLC were carried out on a Waters 625 LC system with a Waters 490E Programmable Multiwavelength Detector using Vydac Peptide and Protein C18 analytical (4.6×250 mm, 5 μm, 1 ml/min) and preparative (10×250 mm, 10 μm, 3 ml/min) columns, respectively. Analyses of mixtures released from one bead were performed on an Ultrafast Microprotein Analyzer (Michrom BioResources, Pleasanton, Calif.) using a Reliasil C18 column (5 μM, 300 A, 1×150 mm). All spectra are reported in ppm relative to tetramethylsilane (δ) using either $CDCl_3$ or $CD_3SOCD_3$ as solvents. UV/VIS absorption spectra were recorded on a Hewlett Packard HP 8452A Diode-Array spectrophotometer using a 1-cm quartz cuvette. Amino acid analyses were carried out on a D-500 system (Durrum Corp., Palo Alto, Calif.) system.

9.1.2 Procedures

Solid phase synthesis was performed manually in polypropylene syringes as described by Krchnak and Vagner (1990, Peptide Res. 3: 182–193). Syntheses were performed on TentaGel S $NH_2$ (TG) resin (Rapp Polymere, Tubingen, Germany, 130 or 80 μm, 0.23 mmol/g) modified with SCAL handle (Patek and Lebl, 1991, Tetrahedron Lett. 32: 3891–3894) (safety-catch amide linker) or with an appropriate linker. Fmoc protecting groups were cleaved with 50% piperidine/DMF for 1×10 min, Tfa groups by repeated treatment (3× 1 min+90 min) with 10% piperidine/water. Npys goups were removed by 0.3M solution of HCl in dioxane for 5+30 min, Aloc group by $(Ph_3P)_4Pd$ in DMF/AcOH/N-Me-Morpholine (10:2:1), Boc groups were cleaved with 30% TFA/DCM containing 3% of anisole for 20 min. A solution of DIEA/DCM (10%) was used for neutralization after Boc cleavage. A mixture of BOP/HOBt/DIEA (1:1:2 eq) in DMF was used for the activation of both Na-Fmoc and Boc amino acids. The completeness of each condensation reaction (1.5–40 hrs) was checked by ninhydrin test, or by chloranil test in the cases of coupling to secondary amino groups. The coupling protocol included washing with DMF (6–8 times) [followed by washing with DCM in case of Boc protected amino acids] between coupling and deprotection and between deprotection and coupling. The SCAL linker was reduced by 20% $(EtO)_2P(S)SH$ in DMPU for 2 hours. Final cleavage was done by 95% TFA–5% water mixture.

9.1.3 Reagents

Commercial-grade solvents were used without further purification. Protected amino acids were obtained from Bachem (Torrance, Calif.), Advanced ChemTech (Louisville, Ky.), or Propeptide (Vert-le-Petit, France). Amines and carboxylic acids were obtained from Aldrich (Milwaukee, Wis.).

9.1.4 Synthesis of a Nonpeptidic Library on Nonpeptidic Scaffolding

Mono tert.butyloxycarbonylethylenediamine. This compound was prepared as described previously (Krapcho et al., 1990, Synthetic Commun. 20: 2559–2564). Briefly, a solution of tert.butyl dicarbonate (5.0 g, 0.023 mol) in dioxane (50 ml) was slowly added to ethylenediamine (11.0 ml, 0.165 mol) in dioxane (60 ml). After 24 hrs of stirring the solvent was evaporated and the residue was dissolved in water (80 ml), insoluble byproduct was filtered off and the filtrate was extracted with dichloromethane (3×100 ml). After evaporation of the solvent the product was crystallized from solvent mixture of diethylether—petroleum ether or ethyl acetate—petroleum ether. Yield 2.6 g (71%). NMR (300 MHz, DMSO-$d_6$, 25° C.) d: 1.39 (s, 9H, tBu), 2.83 (m, 2H, $C^aH_2$), 3.16 (q, 2H, $C^bH_2$), 6.93 (t, 1H, NH), 7.77 (br, 2H, $NH_2$). M.p. 75° C.

N-tert.butyloxycarbonyl-N'-fluorenylmethyloxycarbonylethylenediamine. A solution of fluorenylmethyl succinimidyl carbonate (31.0 g, 0.092 mol) in acetonitrile (300.0 ml) was slowly added to mono tert-butyloxycarbonylethylenediamine (10.0 g, 0.063 mol) dissolved in 10% aq. $Na_2CO_3$ (250 ml). Acetonitrile was evaporated and the product was extracted with ethyl acetate, organic phase was dried over $Na_2CO_3$, concentrated and the product was allowed to crystallize by adding petroleum ether. The product was collected on filter, washed with petroleum ether. Yield 20.0 g (84%). TLC petroleum ether—diethylether 88:12 $R_f$ 0.64. NMR (300 MHz, DMSO-$d_6$, 25° C.) d: 1.37 (s, 9H, tBu), 2.99 (m, 4H, $CH_2CH_2$), 4.20–4.29 (m, 3H, Fmoc $OCH_2CH$—), 6.76 (t, 1H, NH), 7.25 (t, 1H, NH), 7.33–7.89 (m, 8H, Fmoc). M.p. 146°–148° C.

Mono N-fluorenylmethyloxycarbonylethylenediamine trifluoroacetate. N-tert-butyloxycarbonyl-N'-fluorenylmethyloxycarbonylethylene-diamine (20.0 g, 0.052 mol) was treated with trifluoroacetic acid and anisole in dichloromethane (10:10:1) for 1 hour at room temperatute. After evaporation to dryness the crude product was crystallized from solvent mixture of ethyl acetate-n-hexane. Yield 15.0 g (73%). NMR (300 MHz, DMSO-$d_6$, 25° C.) d: 2.85 (m, 2H, $C^aH_2$), 3.22 (m, 2H, $C^bH_2$), 4.23–4.36 (m, 3H, Fmoc $OCH_2CH$—), 7.37 (m, 1H, NH), 7.34–7.89 (m, 8H, Fmoc), 7.77 (br, 2H, $NH_2$). M.p. 128°–129° C.

cis,cis-1,3,5-Trimethylcyclohexane-5-carbocylic acid-1, 3-dicarboxylic anhydride (1). Compound (1) was prepared as described (Askew et al., 1989, J. Am. Chem. Soc. 111: 1082–1090). Briefly; cis,cis-1,3,5-trimethylcyclohexane-1, 3,5-tricarboxylic acid (1.0 g, 0.004 mol) was refluxed in xylene (50 ml) for 19 h under nitrogen using Firestone valve and Dean-Stark trap. The resulting solution was concentrated in vacuo and the product was allowed to crystallize. After collection on filter the product was dried in vacuo at 70° C. for 1 hour. Yield 0.78 g (82%). NMR (300 MHz, DMSO-$d_6$, 25° C.) d: 1.10 (s, 3H, $CH_3$), 1.16 (s, 6H, $2CH_3$), 1.33, 2.39 (d,d, 4H, $2CH_2$), 1.33, 2.15 (d,d, 2H, $CH_2$), 12.60 (s, 1H, COOH). M.p. 252°–253° C., lit.(32) m.p. 252°–254° C.

5-(N-tert.Butyloxycarbonylaminoethylcarboxamide)-cis, cis-1,3,5-trimethylcyclohexane-1,3-dicarboxylic acid (2). Acid anhydride (1) (0.5 g, 0.002 mol) was dissolved in DMF (4 ml) and mono tert.butyloxycarbonylethylenediamine (0.33 g, 0.002 mol) dissolved in DMF (4 ml) was added under nitrogen. Reaction mixture was stirred about 5 hours (TLC monitoring) and then DMF was evaporated. The product was crystallized from solvent mixture of ethyl acetate—petroleum ether. Yield 0.38 g (47%). NMR (300 MHz, DMSO-$d_6$, 25° C.) d: 1.08 (s, 3H, $CH_3$), 1.13 (s, 6H, $2CH_3$), 1.34 (s, 9H, tBu), 1.07, 2.51 (d,d, 4H, $2CH_2$), 2.43 (d, 2H, $CH_2$), 2.96 (m, 4H, $2CH_2$), 6.70 (t, 1h, NH), 7.71 (t, 1H, NH), 12.10 (s, 1H, COOH). M.p. 161°–164° C.

5-(N-tert.Butyloxycarbonylaminoethylcarboxamide)-cis, cis-1,3,5-trimethylcyclohexane-1,3-dicarboxylic anhydride (3). Dicyclohexylcarbodiimide (0.55 g, 0.002 mol) was added to the solution of diacid (2) (1.0 g, 0.0025 mol) in DCM (70 ml) under nitrogen. After 4 hrs of stirring the reaction mixture was concentrated and dicyclohexylurea was filtered off. The filtrate was evaporated to dryness and the residue was crystallized from solvent mixture of ethyl acetate—petroleum ether, dried in dessicator (KOH, $P_2O_5$) in vacuo. Yield 0.9 g (95%)

5-(N-tert.butyloxycarbonylaminoethylcarboxamide)-3-(N-fluorenylmethyloxycarbonylaminoethylcarboxamide)-cis,cis- 1,3,5-trimethylcyclohexane-1-carboxylic acid (4). The anhydride (3) (0.85 g, 0.002 mol) was dissolved in DMF (10 ml) and solution of mono N-fluorenylmethyloxycarbonylethylene-diamine trifluoroacetate (0.88 g, 0.002 mol) in DMF (15 ml) in the presence of triethylamine (pH 8.5 adjusted) was added under nitrogen. Reaction mixture was stirred for 4 hrs (TLC monitoring) and then evaporated to dryness. The crude product was flash chromatographed (Silica Gel Merck 60 230–400 mesh) in solvent system DCM-MeOH 25:1. Fractions containing pure product were combined, evaporated to dryness and the product was crystallized from solvent mixture of ethyl acetate—petroleum ether. Yield 0.32 g (24%). NMR (300 MHz, DMSO-$d_6$, 25° C.) d: 1.08 (s, 6H, $2CH_3$), 1.14 (s, 3H, $CH_3$), 1.35 (s, 9H, tBu), 4.25 (m, 3H, Fmoc $OCH_2CH$—), 6.86 (t, 1H, NH), 7.32–7.89 (m, 8H, Fmoc). M.p. 118–121

Non-peptidic library on non-peptidic scaffolding. The compound (4) was used as scaffolding for a nonpeptidic library. TentaGel S $NH_2$ (0.4 g, titution 0.21 mequiv $NH_2$/g) was subjected to solid phase synthesis using the following protocol:

| Step | Reagent | Time |
|---|---|---|
| 1 | 5% DIEA/DMF | 2 × 5 min |
| 2 | DMF wash | 10 × 2 min |
| 3 | Fmoc—Lys(Boc)/BOP | until ninhydrin test is negative |
| 4 | repeat step 2 | |
| 5 | DCM | 10 × 2 min |
| 6 | TFA/DCM/anisole | 1 × 30 min |
| 7 | repeat step 5 | |
| 8 | 5% DIEA/DCM | 3 × 2 min |
| 9 | repeat step 2 | |

-continued

| Step | Reagent | Time |
|---|---|---|
| 10 | resin was divided into 20 portions and acids defined below coupled. Anhydrides were used as such, other carboxylic acids were coupled using BOP reagent. pivalic acid phenylacetic acid diphenylacetic acid 1-adamantaneacetic acid Z—Gly ClZ-β-Ala ClZ-aminocaproic acid diBoc-quanidinoacetic acid diBoc-ε-quanidinopentanoic acid succinamic acid 2-furoic acid p-hydroxybenzoic acid isonicotinic acid 4-phenylbutyric acid acetic anhydride n-butyric anhydride n-caproic anhydride benzoic anhydride succinic anhydride glutaric anhydride | |
| 11 | repeat step 2 | |
| 12 | 50% piperidine/DMF | 10 min |
| 13 | repeat step 2 | |
| 14a | compound 4/DIC/HOBt | 30 min (preactivation) |
| 14b | product of step 14a | until Kaiser test is negative |
| 15 | repeat step 11–13 | |
| 16 | resin divided into 20 portions and acids defined in step 10 coupled. Anhydrides were used as such, other carboxylic acids were first preactivated by DIC/HOBt mixture. | |
| 17 | DMF wash | 10 × 2 min |
| 18 | DCM | 3 × 2 min |
| 19 | TFA/DCM/anisole | 1 × 30 min |
| 25 | DCM | 5 × 2 min |
| 26 | 5% DIEA/DCM | 3 × 2 min |
| 27 | DMF wash | 4 × 2 min |
| 28 | resin divided into 20 portions and acids defined in step 10 coupled. Anhydrides were used as such, other carboxylic acids were first preactivated by DIC/HOBt mixture. | |
| 29 | DMF wash | 10 × 2 min |
| 30 | DCM wash | 3 × 2 min |
| 31 | TFA/TFMSA/TA | 30 min |
| 32 | DCM wash | 3 × 2 min |
| 33 | DMF wash | 5 × 2 min |

9.1.5 Branched Library on TentaGel

TentaGel S $NH_2$ (5 g, 0.23 mmol/g, 130 µm bead size) was preswollen in DMF and the branched library was built according to the following protocol: (1) Coupling of SCAL linker; (2) Deprotection of Fmoc; (3) Coupling of Fmoc-Lys(Tfa); (4) Deprotection of Fmoc; (5) Coupling of Fmoc-β-Ala; (6) Deprotection of Fmoc; (7) Coupling of Fmoc-Lys(Boc); (8) Deprotection of Fmoc; (9) Coupling of Fmoc-β-Ala; (10) Deprotection of Boc; (11) First randomization; (12) Deprotection of Fmoc; (13) Second randomization; (14) Deprotection of Tfa; (15) Coupling of Fmoc-Lys(Tfa); (16) Deprotection of Fmoc; (17) Coupling of Fmoc-β-Ala; (18) Deprotection of Fmoc; (19) Third randomization; (20) Deprotection of Tfa; (21) Fourth randomization; (22) Deprotection of side-chains. In each randomization the following acids were coupled: acetic, n-butyric, pivalic, n-caproic, benzoic, phenylacetic, 4-phenylbutyric, diphenylacetic, 1-adamantaneacetic, succinic, glutaric, glycine, β-alanine, epsilon-amino-n-caproic, guanidoacetic, gamma-guanidinobutyric, succinamic, p-hydroxybenzoic, 2-furoic, and isonicotinic acid. These subunits, and the corresponding amino acid code for each subunit, are listed in Table 4. Amino acids were coupled as anhydrides when commercially available (10 eq of anhydride, 1.2 eq of DIEA), or they were preactivated for 20 min (acid 12 eq, DIC 10 eq, HOBt 10 eq). Due to their very poor solubility in DMF, guanidino acids (12 eq) were dissolved in DMF containing HOBt and LiCl and activated by DIC. However, in a control experiment only ca 70 to 80% coupling was observed under those conditions. After finishing the synthesis the library was washed with TFA (3×), DCM (5×), DMF (5×), DMF/0.1%HCl (1:1) (3×), and 0.02% HCl.

TABLE 4

Protection, Activation, and Coding Scheme for Acids

| Acid | Prot. | Activ. | Coded By |
|---|---|---|---|
| acetic acid | | anhydr. | Ala |
| n-butyric acid | | anhydr. | Asn |
| pivalic acid | | anhydr. | Asp |
| n-caproic acid | | anhydr. | Glu |
| benzoic acid | | anhydr. | Gln |
| phenylacetic acid | | DIC,HOBt | Gly |
| 4-phenylbutyric acid | | DIC,HOBt | His |
| diphenylacetic acid | | DIC,HOBt | Ile |
| 1-adamantaneacetic acid | | DIC,HOBt | Leu |
| succinic acid | | anhydr. | Lys |
| glutaric acid | | anhydr. | Met |
| glycine | Boc | DIC,HOBt | Orn |
| beta-alanine | Boc | DIC,HOBt | Phe |
| ε-amino-n-caproic acid | Boc | DIC,HOBt | Pro |
| guanidoacetic acid | diBoc | DIC,HOBt | Ser |
| γ-guanidinopentanoic acid | diBoc | DIC,HOBt | Thr |
| succinamic acid | | DIC,HOBt | Trp |
| p-hydroxybenzoic acid | | DIC,HOBt | Tyr |
| 2-furoic acid | | DIC,HOBt | Val |
| isonicotinic acid | | DIC,HOBt1 | Nva |

9.1.6 Branched Encoded Library on TentaGel

TentaGel S $NH_2$ (5 g, 0.23 mmol/g, 130 µm bead size) was preswollen in DMF and the branched library with coding sequence was built according to the following protocol: (1) Coupling of Fmoc-Lys(Ddz-Gly); (2) Deprotection of Fmoc; (3) Coupling of Fmoc-Lys(Tfa); (4) Deprotection of Fmoc; (5) Coupling of Fmoc-β-Ala; (6) Deprotection of Fmoc; (7) Coupling of Fmoc-Lys(Npys); (8) Deprotection of Fmoc; (9) Coupling of Fmoc-β-Ala; (10) Deprotection of Fmoc; (11) First randomization; (12) Deprotection of Ddz in each reaction vessel separately; (13) Coupling of Fmoc-protected coding amino acid; (14) Deprotection of Npys; (15) Second randomization; (16) Deprotection of Fmoc in each reaction vessel separately; (17) Coupling of Fmoc-protected coding amino acid; (18) Deprotection of Fmoc from coding arm; (19) Coupling of Ddz-Phe; (20) Deprotection of Tfa; (21) Coupling of Fmoc-Lys (Npys); (22) Deprotection of Fmoc; (23) Coupling of Fmoc-β-Ala; (24) Deprotection of Fmoc; (25) Third randomization; (26) Deprotection of Ddz in each reaction vessel separately; (27) Coupling of Fmoc-protected coding amino acid; (28) Deprotection of Npys; (29) Fourth randomization; (30) deprotection of Fmoc in each reaction vessel separately; (31) Coupling of Fmoc-protected coding amino acid; (32) Deprotection of Fmoc; (33) Deprotection of side-chains. The library was washed with TFA (3×), DCM (5×), DMF (5×), DMF/0.1%HCl (1:1) (3×), and 0.02% HCl.

9.1.7 Branched Library with Coding on Fast Flow Sepharose (FFS)

FFS was sieved to obtain more narrow particle size distribution (bead size 85–125 um), placed in a reaction vessel for peptide synthesis and washed 10 times with DMF. Fmoc-Gly (2.97 g) in DMF was activated by DIC (1.57 ml) and HOBt (1.35 g) and added to 10 ml of FFS. The reaction was catalyzed by 0.25 g of dimethylaminopyridine and the suspension was shaken overnight. Fmoc-Gly-FFS was washed 10 times with DMF, Fmoc was cleaved, resin was washed with DMF and the substitution calculated according to absorbance of deprotecting solution at 302 nm. Typical substitution was 0.1 mmol/ml. Then mixture of Fmoc-β-Ala and Boc-β-Ala (molar ratio 3:1) was activated by DIC and HOBt and coupled to Gly-FFS in 3 molar excess. FFS was washed 10 times with DMF, Fmoc groups removed and free amino groups acetylated with $Ac_2O$/Py (1:1) for 10 min. After washing 10 times with DMF and DCM, Boc was removed by TFA/DCM/anisole (45:45:10) for 5+30 min, FFS was washed with DCM (10 times), neutralized with 2% DIEA/DCM (3 times 1 min) and washed 10 times with DMF.

The branched library with coding sequence was built according to the following protocol: (1) Coupling of Fmoc-Lys(Ddz-Gly); (2) Deprotection of Fmoc; (3) Coupling of Fmoc-Lys(Alloc); (4) Deprotection of Fmoc; (5) Coupling of Fmoc-β-Ala; (6) Deprotection of Fmoc; (7) Coupling of Fmoc-Lys(Npys); (8) Deprotection of Fmoc; (9) Coupling of Fmoc-β-Ala; (10) Deprotection of Fmoc; (11) First randomization; (12) Deprotection of Ddz in each reaction vessel separately, (13) Coupling of Fmoc-protected coding amino acid, (14) Deprotection of Npys; (15) Second randomization; (16) Deprotection of Fmoc in each reaction vessel separately, (17) Coupling of Fmoc-protected coding amino acid, (18) Deprotection of Fmoc from coding arm, (19) Coupling of Ddz-Phe, (20) Deprotection of Alloc; (21) Coupling of Fmoc-Lys(Npys); (22) Deprotection of Fmoc; (23) Coupling of Fmoc-β-Ala; (24) Deprotection of Fmoc; (25) Third randomization; (26) Deprotection of Ddz in each reaction vessel separately, (27) Coupling of Fmoc-protected coding amino acid, (28) Deprotection of Npys; (29) Fourth randomization; (30) deprotection of Fmoc in each reaction vessel separately, (31) Coupling of Fmoc-protected coding amino acid, (32) Deprotection of Fmoc, (33) Deprotection of side-chains. The library was washed with TFA (3×), DCM (5×), DMF (5×), DMF/0.1%HCl (1:1) (3×), and 0.02% HCl.

9.1.8 Library of Mixed Peptide and Non-Peptide Subunits

The library was synthesized on TentaGel S $NH_2$, 90 μm, (Rapp Polymere, Germany) (2 g, substitution 0.25 mmol/g, 0.5 mmol). First, the sequence Gly-βAla-Gly-βAla-Gly-Lys (Tfa)-TG SEQ ID NO:6 identical for all sequences was synthesized using 5 eq excess of activated Fmoc-amino acids (DIC/HOBt activation). After the N-terminal Fmoc-deprotection, the resin was divided into 9 portions in the ratio 17:8:5:1:1:1:1:1:1 (36 parts, 0.014 mmol per part). The structures of the subunits used in this library are shown in FIG. 8, along with the amino acid dipeptide code for each of the subunits. Subunits that were added to each portion are indicated in parentheses. These portions were further treated as follows:

17-part portion ($X_2$=1–17): Fmoc-Dab(Boc)-OH was coupled (5 eq excess), the Boc-side chain protecting group was removed by TFA/DCM/anisole (50:50:2, 15 min) and after the washing steps this portion was divided into 17 parts. Corresponding acids were coupled to the free side chain amino group by standard DIC/HOBt activation.

8-part portion ($X_2$=18–25): Fmoc-Asp(OBu$^t$)-OH was coupled (5 eq excess), the Bu$^t$-side chain protecting group was removed by TFA/DCM/anisole (50:50:2, 15 min) and after the washing steps this portion was divided into 8 parts. Corresponding amines were coupled to the side chain according to the procedure described below.

5-part portion ($X_2$=30–34): A solution of Fmoc-IDA-anhydride (10 eq, 0.7 mmol in 2 ml DMF) was added to the resin and shaken for 30 min. The procedure was repeated once more, the resin washed with DMF and divided into 5 parts. Amines were coupled according to the following procedure.

The general procedure for coupling of amines in the side chain, used for linking the structures 18–25 and 30–34, follows: The resin bound carboxy-groups (0.014 mmol per part) were activated by a mixture of DIC/HOBt (10 eq) in 0.4 ml DMF for 30 min. This mixture was removed without washing and 30 eq of the appropriate amine in 0.2 ml DMF were added. In the case of p-toluidine, equimolar amount of DIEA was added for the neutralization of the hydrochloride. The resin was shaken for 1 hour and washed with DMF.

1-part (single) portions ($X_2$=26–29, 35, 36): The N-Fmoc-protected monoamides of iminodiacetic acid (for structures 26–29) (10 eq, 0.014 mmol per part) and Fmoc-Cys(Bzl)-OH and Fmoc-D-Pen(Bzl)-OH (5 eq, 0.07 mmol) were coupled by DIC/HOBt activation to the single portions, respectively.

Further procedures for all 36 portions: The N-terminal Fmoc-group was cleaved by piperidine/DMF. To the sub-units 1–25, 35, 36, Boc-Gly-OH was coupled by DIC/HOBt activation (5 eq, 0.07 mmol per part). Subunits 26–34 were reacted with symmetrical anhydride of Boc-Gly-OH (10 eq., 0.12 mmol per part) in DMF overnight.

The encoding procedure: Cleavage of Lys(Tfa)-protecting group (identical for all 36 parts): The resin was washed with water and treated with 20% piperidine/$H_2O$ (two times, 10+30 min). The resins were then washed with water and DMF. Subsequently, the tag for all sequences was synthesized by Fmoc-strategy (DIC/HOBt activation, 10 eq, 0.14 mmol per part) without cleavage of the N-terminal Fmoc-protecting group of the tag. Coding sequences for the tag are shown in FIG. 8. All 36 portions were then collected, mixed and divided into two portions. To one half only, Boc-Gly was coupled after the Boc-group deprotection in the main chain. Both portions were mixed, the Boc-protecting group was removed and the resin divided into 13 portions. Fmoc-Tyr(Bu$^t$)-OH, Fmoc-Trp-OH, Fmoc-Lys (Boc)-OH, Fmoc-Thr (Bu$^t$)-OH, Fmoc-His(Trt)-OH, Fmoc-Pro-OH, Fmoc-Phe-OH, Fmoc-Arg(Pmc)-OH, Fmoc-Asn-OH, Fmoc-Ser (Bu$^t$)-OH, Fmoc-Glu(OBu$^t$)-OH, Fmoc-Asp(OBu$^t$)-OH and Fmoc-Gln-OH (10 eq, 0.38 mmol) were coupled by DIC/HOBt activation to those 13 portions. Side chain deprotection: Boc- and Bu$^t$-side chain protection groups were cleaved by TFA/DCM/anisole (50:50:2) (15 min exposure), the Trt-group was cleaved by the same mixture with addition of 1 drop of $^iPr_3SiH$ for 15 min. The Pmc-group was cleaved by mixture K for 1 hour. After washing and neutralization steps (DCM, 7% DIEA/DCM, DMF), all 13 portions were collected and the N-terminal Fmoc-group was cleaved. The library was then washed with DMF and transferred into 0.1% aqueous HCl.

9.1.9 Screening Protocol of the Library

The peptide library was screened according to the published procedure (Lam and Lebl, 1992, Immunomethods 1:

11–15). The peptide beads were first mixed with double-distilled water to remove the DMF. After extensive washing with PBS (137 mM NaCl, 2.7 mM KCl, 4.3 mM Na$_2$HPO$_4$, 1.4 mM KH$_2$PO$_4$, pH 7.2), the beads were coated with 0.05% gelatin (w/v) to block any nonspecific binding. The beads were then incubated with 60 pM biotinylated anti-β-endorphin antibody (clone 3-E 7, Boehringer Mannheim) in 2× PBS/Tween/gelatin overnight. After thorough washing, streptavidin-alkaline phosphatase was added. One hour later, the beads were washed, the substrate was added, and color development proceeded as described above. The colored beads were then physically isolated and subjected to sequencing.

9.2 Results and Discussion

An alternative non-peptidic scaffolding is based on the use of Kemp's triacid (Kemp and Petrakis, 1981, J. Org. Chem. 46: 5140–5143) (Scheme XV).

SCHEME XV

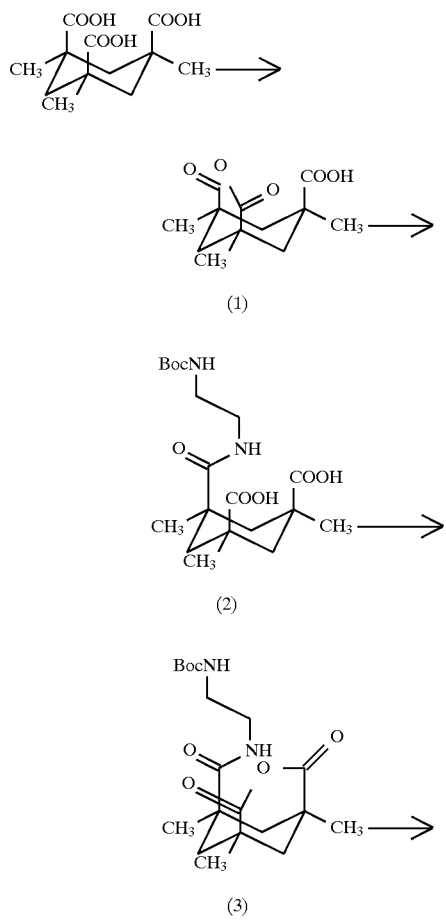

-continued
SCHEME XV

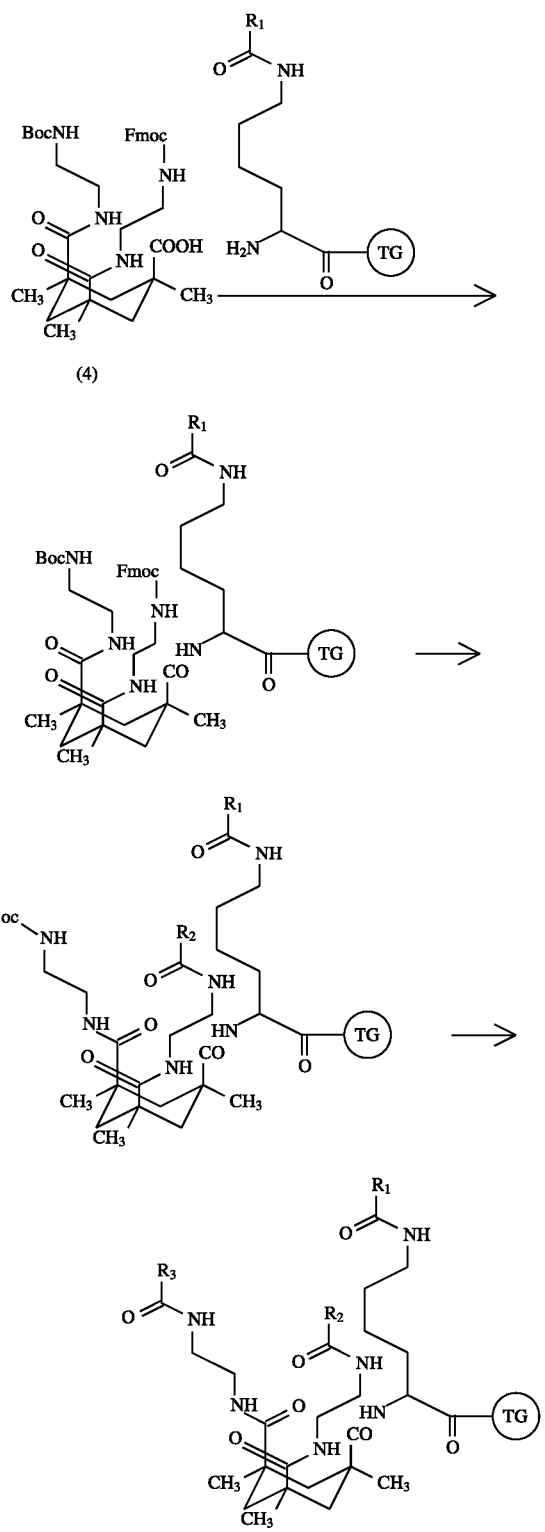

In this structure the three carboxyl groups are constrained to the triaxial conformation. Anhydride acid 1 was prepared by dehydration procedure (Askew et al., 1989, J. Am. Chem. Soc. 111: 1082–1090) using a Dean-Stark trap under nitrogen. This acid anhydride was opened by nucleophilic attack by mono tert-butyloxycarbonylethylenediamine yielding amide diacid 2. The same method for dehydration is not applicable for this amide diacid because of instability of Boc protecting group under these conditions. A mild alternative for preparation of the amide anhydride 3, peculiar to peptide chemistry was the use of the common dicyclohexylcarbodiimide procedure in methylene chloride. The amide anhydride 3 was then opened by fluorenylmethyloxycarbonyl-ethylenediamine to the corresponding diamide acid 4. Mono protected ethylenediamines have been prepared starting from Boc-ethylenediamine which was prepared by bocylation of ethylenediamine using tert-butyl dicarbonate (Krapcho et al., 1990, Synthesis Commun. 20: 2559–2564). Mono Boc-ethylenediamine was used as such and it served also as starting compound for preparation of mono fluorenylmethyloxycarbonyl-ethylenediamine trifluoroacetate via N-Boc-N'-Fmoc-ethylenediamine.

Diamide acid 4 can be used either for the synthesis of scaffolding bearing the third chain containing orthogonal protecting group (Ddz, Alloc) and carboxyl function or as scaffold itself providing that the third randomization is done separately. The use of 1 as a scaffolding was chosen to synthesize the totaly nonpeptidic library. The first randomization was done on lysine side chain although any trifunctional amino acid can be used for this purpose, and the second and the third randomization was performed on the scaffolding. Using this conformationally constrained scaffolding a non-peptide library randomized with 20 different carboxylic acid was built.

A scaffolding mapping a larger conformational space is a simple branched attachment constructed by consecutive coupling of diamino carboxylic acids. Various types of the scaffolding mapping extensive space are flexible cyclic or branched scaffoldings. The principles of these libraries are illustrated generally in FIG. 4. Scheme XVI shows a specific example of such a library:

SCHEME XVI

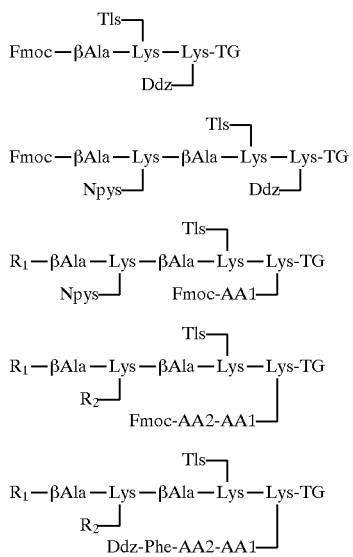

-continued
SCHEME XVI

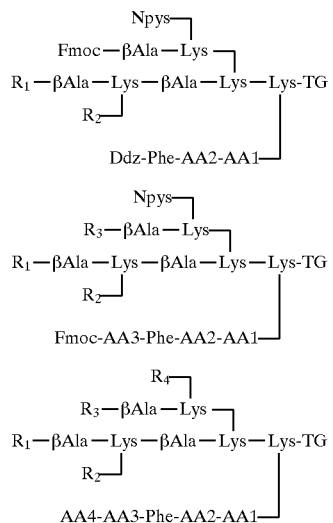

The synthesis of this scaffolding required the use of four independent (orthogonal) protecting groups. We have tested the use of trifluoroacetyl group introduced into peptide chemistry in the fifties (Schallenbert and Calvin, 1955, J. Am. Chem. Soc. 77: 2779), but that was not used due to the harsh conditions required for its deprotection, as well as due to its ineffectiveness in protection against racemization when used as α-amino group protection. We have found that this group is not cleaved during Fmoc deprotection using 50% piperidine in dimethylformamide, but it is completely cleaved by 1–2 h exposure to piperidine solution (20%) in water, which, however, also cleaves Fmoc group. The strategy used in the construction of this library is clear from Scheme XV.

Non-amino acid subunits can be combined with standard amino acids. We have shown that this approach can yield reasonable binding structures by constructing the minilibrary of 936 members, having selected amino acids randomized in position 1, one or two glycines in position 2 and 3 and a set of aromatic amines coupled to the β-carboxyl group of aspartic acid or side chain modified iminodicarboxylic acid, or aromatic acids coupled to the side chain of diaminobutyric acid in position 4, or benzylhalides coupled to the side chain of sulfur containing amino acids (cysteine and penicillamine). The structure of the library is shown in Scheme XVII:

SCHEME XVII

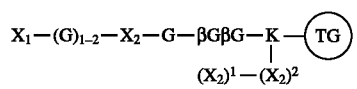

—$X_1$ = Tyr, Trp, Lys, Thr, His, Pro, Phe, Arg, Asn, Ser, Glu, Asp, Gln
—$X_2$ = Building blocks 1–36
—$(X_2)^{1-2}$ = Coding sequence Total number of permutations: 936

Position 4, which contains the non-amino acid subunit, may create problems during the sequencing and therefore this position has been encoded. Since more than 20 building blocks were used in the randomization, a doublet amino acid coding strategy was used (FIG. 8). To avoid complications in structural determination, the amino acids used for coding do not overlap with the set used for the randomization of the position 1 and amino acid in position 2. Using a doublet codon of 6 amino acids, up to 36 different building blocks could be encoded.

This minilibrary was screened against a model system, anti-β-endorphin monoclonal antibody. Positively reacting beads were subjected to three cycles of Edman degradation, and the interacting structures, deduced from the obtained data are given in Scheme XVII. The structure of the natural ligand for the anti-β-endorphin monoclonal antibody is also shown in Scheme XVIII:

SCHEME XVIII

Found in library:

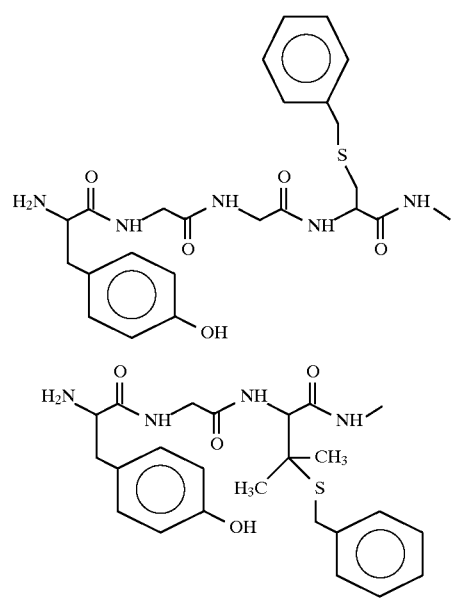

Natural ligand:

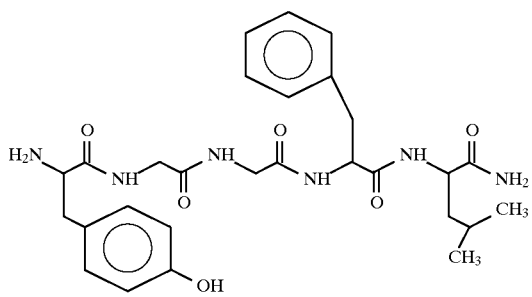

Compounds that were selected on the basis of binding with the anti-β-endorphin monoclonal antibody were synthesized bound to the beads and in the free form and their binding affinities were determined. Bead bound sequences have shown specific binding (competable by leucine enkephalin). As can be seen (Scheme XVIII), the binding to the antibody requires two aromatic groups in the appropriate distance. The structure connecting those two aromatic groups is nevertheless very important for the binding affinity.

10. EXAMPLE: SELECTIVE ACTIVATION OF SURFACE FUNCTIONAL GROUPS ON A RESIN BEAD

The present example describes preparation of a solid phase support particle having a "surface" of the particle physically separate from the "inside" of the carrier, and synthesizing the screening structure on the surface and the coding molecule inside of the bead. The surface in this sense should be understood as the portion of the bead accessible to the macromolecular acceptor molecule. The available surface of the bead corresponds approximately to the calculated surface area based on the bead dimensions for an acceptor molecule of extremely high molecular weight. Alternatively, the surface area can be determined by various methods utilizing penetration into a material (including inner surface of all pores in the polymeric bead) for acceptor molecules with low molecular weight. Understandably, acceptor molecules that freely penetrate the polymeric network will not recognize any difference between surface and inside of the polymeric particle. The available surface of the particle also include a dynamic component.

10.1 Materials and Methods

10.1.1 Removal of the Surface Content of the Peptide from Solid Phase Bead

Model peptides (YGGFL SEQ ID NO:7, LHPQF SEQ ID NO:8, LHPQFYG SEQ ID NO:9) were synthesized on TentaGel AM (Rapp Polymere, Tubingen, Germany, 0.21 mmol/g) having the linker β-Ala-Gly-β-Ala-Gly attached to it. Synthesis was performed by standard solid phase technique utilizing Fmoc protected amino acids and diisopropylcarbodiimide in the presence of N-hydroxybenzotriazole as a coupling reagent. Peptides were deprotected in two steps using trifluoroacetic acid with scavengers (ethanedithiol, water, and thioanisole), and piperidine (20%) in dimethylformamide. Beads were carefully washed and transferred to 0.1M ammonium carbonate buffer of pH 7.7. Chymotrypsin (1 mg) was added and suspension was shaken at 37° C. for 20 hours. The same treatment was repeated twice for 4 hours. Sequencing of randomly selected beads from every group have shown that the peptide content on the beads did not change significantly.

10.1.2 Synthesis of Different Peptides on the Surface and Inside of the Polymeric Bead TentaGel AM resin (0.21 mmol/g, 1 g) was modified by condensation of Boc-Phe. Resin was washed and transferred to the 0.1M ammonium carbonate buffer pH 7.7. Chymotrypsin treatment was performed in the same way as described above. After careful washing by the same buffer and water, resin was washed with dimethylformamide and the standard solid phase synthetic scheme using Fmoc protecting groups and diisopropylcarbodiimide and N-hydroxybenzotriazole as coupling reagent was used for the synthesis of YGGFL SEQ ID NO:7 sequence. After the coupling of Fmoc-Tyr(But) in the last coupling step, Fmoc group was not removed and the resin was treated with 50% trifluoroacetic acid in dichloromethane. In the next synthetic steps Boc protected amino acids were used. Coupling was performed using the same reagent as above, the Boc group was removed after each step by 50% trifluoroacetic acid and the protonated amino group was made available for the coupling by treatment with diisopropylethylamine solution in dimethylformamide (5%). Peptides were deprotected in two steps using trifluoroacetic acid with scavengers (ethanedithiol, water, and thioanisole), and piperidine (20%) in dimethylformamide. Beads were carefully washed and prepared for staining with anti-β-endorphin as described previously. Staining of the beads was indistinguishable from staining of the beads containing only YGGFL sequence.

10.2 Results and Discussion

An enzyme has been used to selectively cleave a peptide from the surface of a bead. The test sequences YGGFL SEQ ID NO:7 and LHPQFYG SEQ ID NO:9 were prepared and incubated with chymotrypsin and the reactivity of the beads was tested.

Treated beads were tested for binding to anti-β-endorphin and streptavidin. Results are given in the Table 5.

TABLE 5

Binding to the Beads After Treatment With Chymotrypsin

| Peptide on Bead | Binding to Antibody | | Streptavidin | |
|---|---|---|---|---|
| | No CT | + CT | No CT | + CT |
| YGGFL SEQ ID NO:7 | 3+ | — | — | — |
| LHPQF SEQ ID NO:8 | — | — | 3+ | 2+ |
| LHPQFYG SEQ ID NO:9 | — | — | 3+ | — |

CT = chymotrypsin

Beads with YGGFL completely lost binding activity to anti-β-endorphin antibody (Table 5). Beads containing LHPQF-YG SEQ ID NO:9 also completely lost activity with streptavidin. However, the decrease in the total amount of LHPQF-YG SEQ ID NO:9 or YGGFL SEQ ID NO:7 was minimal, indicating no effect on the interior of the bead. In this case, since LHFQF SEQ ID NO:10 was a poor substrate for chymotrypsin, the YG linker was used. Edman degradation showed that the peptide content on the beads did not change significantly.

Based on these preliminary results, chymotrypsin was used as a selective deprotecting reagent. A simple substrate for chymotrypsin, Boc-Phe, was synthesized on all available amino groups of the solid carrier. Incubation of this modified resin under various conditions led to the release of approximately the same amount of Boc-Phe: 1.1%. The deprotected amino group was used for the synthesis of YGGFL using Fmoc strategy. Synthesis was followed by quantitative measurement of Fmoc release, and the readings confirmed that approximately 1% of available amino groups were used for the synthesis. The Boc protecting group from the remaining amino groups on each bead was cleaved by TFA and the sequence LHPQF was assembled using Boc synthesis. All protecting groups were removed and the testing revealed positive reaction with both anti-β-endorphin and streptavidin.

Randomly selected beads were submitted for Edman degradation and the following results were obtained (values in pmoles): 1st cycle: L 114, Y<1; 2nd cycle: H 86, G<1; 3rd cycle: P 94, G<1; 4th cycle: Q 78, F 4 (preview); 5th cycle: F 73, L<1. Edman degradation analysis show the sequence LHPQF SEQ ID NO:8 at the level of 100–120 pmoles per cycle, and negligible content of amino acids expected for YGGFL SEQ ID NO:7 sequence. This means that even though YGGFL SEQ ID NO:7 is not present in the bulk of the bead, it is available on the surface of the bead for the interaction with the relevant acceptor.

LHPQF SEQ ID NO:8 is also still available for interaction with streptavidin. This is probably due to the lower molecular weight of streptavidin, allowing it to penetrate inside of the polymeric bead.

10.3 Discussion

The present Example clearly demonstrates that an enzyme can selectively deprotect the surface, but not the interior, of a resin bead. In this case, chymotrypsin cleavage of the sequence LHPQFYG proceeded efficiently. Binding of streptavidin, which is specific for LHPQF SEQ ID NO:8, was completely abrogated.

Subsequent experiments with a Boc-Phe substrate derivatized beads showed that two different peptides can be synthesized on a bead, with one peptide segregated primarily to the surface and the other peptide segregated primarily to the inside.

11. EXAMPLE: PREFERENTIAL BLOCKING OF THE FREE AMINO GROUPS ON THE SURFACE OF A TENTAGEL BEAD

The present Example demonstrates the feasability of blocking the surface of a resin bead while leaving the functional groups in the interior of the bead free for reaction and synthesis of a compound, for example, a coding molecule.

11.1 Materials and Methods

TentaGel amide AM resin (0.3 meq/gram substitution) was hydrated in $H_2O$ for several hours, and washed with 0.1M 2-[N-morpholino]ethanesulfonic acid (MES) buffer, pH 5.7. A varying amount (0 to 10 mg) of polyglutamic acid (Mr 30,000, Sigma Chemical) was added to each of the 0.2 ml of settled bead. Sixty mg of 1-ethyl-3-(3-dimethylaminopropyl) carbodiimide-HCl (EDC) was then added to each tube. The reaction mixtures were rocked gently overnight. The beads were then washed into double distilled (dd) $H_2O$ and 0.24 mmol ethanolamine plus 60 mg EDC in MES buffer were added to each sample. After 4 hours of gentle shaking, the resin was washed extensively with dd $H_2O$. The resin was then lyophilized to dryness. The treated resin was swollen in dimethylformamide (DMF). Using Fmoc chemistry, the peptide, YGGFLGGG SEQ ID NO:11 was synthesized on each of the treated resin samples using standard techniques. The N-terminal Fmoc group and the side chain protected groups were removed with piperidine and trifluoracetic acid as described (Lam et al., 1991, Nature 354: 82–84). After neutralization with diisopropylethylamine (DIEA), the resin beads were washed extensively and the beads prepared for staining with anti-β-endorphin as described in Section 10, supra.

11.2 Results and Discussion

The ability to block surface functional groups on a resin bead with polyglutamic acid was directly proportional to the amount of polyglutamic acid used (Table 6). Significantly, the polyglutamic acid-blocked resin stained only weakly, suggesting that most of the surface amino groups were blocked prior to the synthesis of the YGGFLGGG SEQ ID NO:11 peptide. More importantly, however, was that the amount of peptide in both the blocked and unblocked resin was about the same (Table 7) indicating that the polyglutamic acid block occurred only on the surface of the bead, and that the free amino groups inside the beads remained intact for subsequent peptide synthesis.

TABLE 6

Semi-Quantitative Staining of Peptide-Beads

| Extent of Blocking: Polyglutamic Acid, mg. per 0.2 ml Resin | Labeling With Biotinyl-Anti-β Endorphin Followed by Streptavidin-AP | Labeling With Streptavidin-AP Alone |
|---|---|---|
| 0 | 3+ | — |
| 0.016 | 3+ | — |
| 0.08 | 2+ | — |
| 0.04 | 1+ | — |
| 2.0 | 1+ | — |
| 10 | trace | — |

TABLE 7

| | | Y | G | G | F | L | G | G | G |
|---|---|---|---|---|---|---|---|---|---|
| Poly-glutamic Acid (10 mg) | I | 609, | 615, | 692, | 665, | 579, | 657, | 675, | 655 |
| | II | 996, | 885, | 839, | 772, | 696, | 522, | 550, | 506 |
| Without Blocking | I | 876, | 752, | 752, | 774, | 680, | 733, | 707, | 717 |
| | II | 519, | 534, | 332, | 559, | 471, | 540, | 550, | 335 |

Micro Sequencing pmole amino acid (10 beads/experiment)*

Additional experiments have involved reversibly coupling polymer onto which Boc-Glu was attached via its α-carboxly group. After the coupling of this modified polymer onto the bead surface and appropriate modification of "inside" amino group, the Boc group from glutamic acid was cleaved. The beads were then treated with one cycle of Edman degradation, which regenerated amino groups that had been protected by the glutamic acid polymeric reagent. Different peptides were synthesized on separate parts of the bead, i.e., on the surface and inside.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

12. EXAMPLE: SUBUNITS SUITABLE FOR THE CONSTRUCTION OF NONPEPTIDIC LIBRARIES

The construction of nonpeptidic libraries requires the selection of subunits suitable for inclusion into solid phase synthesis. The present example concerns the selection of subunits suited to three different chemical methodologies.

12.1 Acylation of Primary Amino Group

Experimental Protocol: One mmol of acid was dissolved in 2 ml of DMF, 0.5 mmol of DIC added (1 mmol in the case of dicarboxylic acids) and reacted with approximtely 100 mg of Trp-RAM-TG overnight. The completion of the reaction was assessed by Kaiser test. The resin was then washed with DMF, DCM, dried. The product was cleaved by one hour's exposure to 1 ml of 95% TFA, 5% water. The reaction mixture was ten diluted with with 5 ml water and analyzed by HPLC and MS.

The requirements for acceptance were that the products have the expected M.W. and the content of the main product in a crude mixture is more than 80% of the total area under the curve of the HPLC chromatogram and that the major product have the expected molecular weight. Table 8 displays the results of the tests of 33 acids. Of the 33, 7 were rejected as unsuitable for use. A further two compounds, 4-hydroxybenzoic acid and 4-hydroxyphenylacetic acid, were incompatible with monosynthesis using tryptophan but were found usable in different model experiments using the $N^{\alpha}$-amino group of lysine(Fmoc).

TABLE 8

Acylation of Primary Amino Group

| Acid | Solubility | Kaiser | HPLC | MW | MS | Selected |
|---|---|---|---|---|---|---|
| γ-Guanidinobutyric | heat | – | OK | 330 | OK | Yes |
| Succinamic | OK | – | OK | 302 | OK | Yes |
| 1-Naphtylacetic | OK | – | OK | 371 | OK | Yes |
| Diphenylacetic | OK | – | 2 peaks | 397 | OK | Yes |
| Biphenylacetic | OK | – | OK | 397 | OK | Yes |
| Pentafluorophenylacetic | OK | – | OK | 411 | OK | Yes |
| 4-Trifluoromethylbenzoic | OK | – | OK | 375 | OK | Yes |
| 4-Hydroxybenzoic | OK | (+) | | 323 | not OK | Yes |
| 4-Hydroxyphenylacetic | OK | – | OK | 337 | not OK | Yes |
| 3-Nitrophenylacetic | OK | + | 2 peaks | 366 | OK | Yes |
| 4-Methoxybenzoic | OK | – | 2 peaks | 337 | OK | No |
| 2-Nitro-4,5-dimethoxybenzoic | OK | – | OK | 412 | OK | Yes |
| 3-(3,4,5-trimethoxyphenyl)propionic | OK | – | OK | 425 | OK | Yes |
| 4-Guanidinobenzoic | OK | ++ | 2 peaks | 364 | OK | Yes |
| 4-Dimethylaminobenzoic | OK | + | OK | 350 | OK | Yes |
| 4-(Pyrrole-1-yl)benzoic | OK | – | not OK | 372 | not OK | No |
| 4(3-Methyl-5-oxo-2-pyrazolin-1-yl)benzoic | heat | red | OK | 403 | OK | Yes |
| 2-Pyrrolecarboxylic | OK | (+) | OK | 296 | not OK | No |
| 1-Methyl-2-pyrrolecarboxylic | HOBt, heat | ++ | not OK | 310 | | No |
| 1,4-Dimethyl-2,3-pyrroledicarboxylic | OK | (+) | OK | 382 | OK | Yes |
| 2-Methyl-4-nitro-1-imidazolepropionic | OK | – | OK | 384 | OK | Yes |
| 2-Amino-1-imidazoleacetic | HOBt, heat | ++ | not OK | 328 | | Yes |
| 2 Pyrazolecarboxylic | OK | – | not OK | 297 | | No |
| 3-amino-1,2,4-triazole-5-carboxylic | | | | 313 | Yes | |
| 4-Imidazoleacetic | heat | ++ | OK | 311 | OK | Yes |
| i-nicotinic | HOBt, heat* | | | 308 | | No |
| 2-Hydroxy-i-nicotinic | OK | (+) | not OK | 324 | | No |
| 2,3-Pyridinedicarboxylic | OK | – | 2 peaks | 352 | OK | Yes |
| 2-Pyrazinecarboxylic | heat | – | OK | 309 | OK | Yes |
| 2,3-Pyrazinedicarboxylic | OK | – | OK | 353 | OK | Yes |

TABLE 8-continued

| Acylation of Primary Amino Group | | | | | | |
|---|---|---|---|---|---|---|
| Acid | Solubility | Kaiser | HPLC | MW | MS | Selected |
| 1-Methylindole-2-carboxylic | OK | – | OK | 360 | OK | Yes |
| 2-Methyl-3-indoleacetic | OK | – | OK | 374 | OK | Yes |
| Indole-4-carboxylic | OK | – | OK | 346 | OK | Yes |

*precipitated after cooling

12.2 Nucleophilic Displacement of Halogen by Amines

Experimental Protocol: Bromoacetic acid (5× molar excess) was coupled via symmetrical anhydrides to TG130 for 10 min, recoupled for 10 min. using the same method. The test amine was coupled using a 1M solution in DMSO, overnight. After suitable washing Fmoc-Gly was coupled (HOBt, DIC) for 1 hour, the Fmoc group removed, and Fmoc release calculated and compared to a theoretical release 45 μmol/ml. In a second set of experiments, the purity and identity of products were tested by the synthesis of the model compounds R-NH-CH$_2$-CO-Gly-Trp-RAM-TG, synthesized by a similar protocol and cleaved from the resin with 1 ml of 95% TFA, 5% water for 1 hour, followed by dilution with about 5 ml of water to perform analytical HPLC and MS.

A total of 33 amines were tested of which 21 were found to be acceptable for incorporation into solid phase synthesis. The results of these studies are given below.

12.3 Reductive Alkylation

12.3.1 Generalized Methods

Experimental Protocol: A 20 molar excess of the test aldehydes were added to about 100 mg of (Exp. A) H-Gly-RAM-TG or (Exp. B) H-βAla-Gly-Trp-RAM-TG swollen in 1 ml MeOH-DCM-AcOH 40:10:1, and the reaction was allowed to proceed overnight. The resin was washed with 1% AcOH in DMF and then reexposed to a 20 molar excess of the test aldeyde overnight. Thereafter the resin was washed with MeOH-DCM-AcOH 40:10:1, and to 1 ml of this mixture a 20 molar excess of NaBH$_3$CN was added and allowed to react overnight. The resin was then washed with DMF/1% AcOH, and a second 20 molar excess of NaBH$_3$CN was added for an overnight reaction. After washing, all samples were acylated with Fmoc-Gly. In the Exp. A, after removing the Fmoc, the product was acylated with Fmoc-Trp. The resin was then treated to remove the Fmoc, washed with DMF, DCM, dried, the product was then cleaved with 1 ml of 95% TFA, 5% water for 1 hour. After

TABLE 9

| Nucleophilic Displacement of Halogen by Amines | | | | | |
|---|---|---|---|---|---|
| Amine | MW | Fmoc | HPLC | MS | Selected |
| Ethylamine | 45.08 | 31 | OK | OK | Yes |
| i-Propylamine | 59.11 | 27 | OK | OK | Yes |
| Butylamine | 73.14 | 41 | OK | OK | Yes |
| i-Butylamine | 73.14 | 24 | OK | OK | Yes |
| t-Butylamine | 73.14 | 4 | * | * | No |
| Cyclopentylamine | 85.15 | 28 | OK | OK | Yes |
| Cyclohexylamine | 99.18 | 24 | OK | OK | Yes |
| 2-Amino-norbornane | 111.19 | 35 | OK | OK | No |
| Ethanolamine | 61.08 | 31 | OK | OK | Yes |
| 3-Aminopropanol | 75.11 | 40 | OK | OK | Yes |
| 1-Amino-2-propanol | 75.11 | 43 | OK | OK | Yes |
| 2-Methoxyethylamine | 75.11 | 26 | OK | OK | Yes |
| Tetrahydrofurfurylamine | 101.15 | 27 | OK | OK | No |
| β-Ala—OtBu | 181.6 | 22 | OK | OK | Yes |
| Ethylendiamine(Boc) | 120 | 29 | OK | OK | Yes |
| 2-(2-Aminoethyl)-1-methylpyrrolidine | 128.1 | 35 | OK | OK | Yes |
| 1-Aminopiperidine | 100.17 | 2.2 | * | * | No |
| 1-Amino-4-methylpiperazine | 115.0 | 20 | Not OK | Not OK | No |
| 4-Aminomorpholine | 101.14 | 3 | * | * | No |
| Benzhydrylamine | 183.25 | 12.5 | Not OK | Not OK | No |
| Naphthalene-methylamine | 157.22 | 24.7 | OK | OK | Yes |
| 2-Aminoindan | 169.96 | 0 | * | * | No |
| 4-(Trifluoromethyl)-benzylamine | 175.16 | 29 | OK | OK | Yes |
| 2-Amino-1-phenyl-ethanol | 137.18 | 29 | OK | OK | Yes |
| Tyramine | 1371.8 | 27 | OK | OK | Yes |
| 4-Methoxy-benzylamine | 137.18 | 34 | OK | OK | Yes |
| 3,5-Dimethoxy-benzylamine | 167.21 | 31 | OK | OK | Yes |
| 4-(Dimethylamino)-benzylamine | 150.22 | not soluble in DMSO | | | No |
| 2,4-Dinitrophenyl-hydrazine | 198.0 | 5 | * | * | No |
| Aniline | 93.18 | 1.2 | * | * | No |
| p-Toluidine | 143.0 | 7.0 | * | * | No |
| p-Anisidine | 123.15 | 2.8 | * | * | No |

*Amines, with low Fmoc release. Experiment was repeated and if low Fmoc release occurred again, the amine was excluded from further experiments.

Dilution with about 5 ml water, analytical HPLC and MS were performed.

A total of 31 test aldehydes were tested to determine their suitablility for inclusion in the solid phase synthesis. The results, given in Table 10 indicate that 19 of these were acceptable.

TABLE 10

Reductive Alkylation

| Aldehyde | Kaiser | HPLC | MW | MS | Selected |
|---|---|---|---|---|---|
| Experiment "A" | | | | | |
| Butyraldehyde | brown | not OK | | | No |
| 2-Methylbutyraldehyde | light blue | OK | 387 | OK | Yes |
| 2-Ethylbutyraldehye | brown | OK | 401 | OK | Yes |
| Trimethylacetaldehyde | brown | OK | 387 | OK | Yes |
| i-Valeraldehye | brown | not OK | | | No |
| 2-Methylvaleraldehyde | light blue | OK | 401 | OK | Yes |
| 3-Methylthiopropionaldehyde | light blue | not OK | | | No |
| Cyclohexanecarboxaldehyde | light blue | OK | 413 | OK | Yes |
| 5-Noorbornene-2-carboxaldehyde | brown | not OK | | | No |
| Benzaldehyde | brown | OK | 407 | OK | Yes |
| 4-Noitrobenzaldehyde | brown | OK | 452 | OK | Yes |
| 4-Hydroxybenzaldehyde | light blue | OK | 423 | OK | Yes |
| Hydrocinnamaldehyde | brown | not OK | | | No |
| Vanillin | brown | OK | 453 | OK | Yes |
| 2-Thiophenecarboxaldehyde | light blue | OK | 413 | OK | Yes |
| Imidazole-2-carboxaldehyde | brown | no OK | | | No |
| Pyridine-4-carboxaldehyde | brown | OK | 408 | OK | Yes |
| α,α,α-Trifluoro-o-tolualdehyde | brown | OK | 475 | OK | Yes |
| Experiment "B" | | | | | |
| 4-Dimethylamino-benzaldehyde | brown | not OK | | | No |
| 4-Methoxybenzaldehyde | brown | OK | 507 | OK | Yes |
| 2,4,6-Trimethoxy-benzaldehyde | brown | not OK | | | No |
| Indole-3-carboxaldehyde | brown | not OK | | | No |
| 1-Acetylindole-2-caboxaldehyde | brown | OK | 559 | nd | Yes |
| 4-Carboxybenzaldehyde | light blue | OK | 522 | not OK | No |
| β-naphtaldehyde | brown | OK | 528 | OK | Yes |
| Phenylacetaldehyde | brown | not OK | | | No |
| 4-Phenylbenzaldehyde | brown | OK | 554 | OK | Yes |
| 3-Phenoxybenzaldehyde | brown | OK | 570 | OK | Yes |
| Pyrrole-2-carboxaldehyde | brown | not OK | | | No |
| 2-Hydroxybenzaldehyde | brown | OK | 494 | OK | Yes |
| Quinoline-4-carboxyaldehyde | blue | not OK | | | No |

12.3.2 Specific Methods

The following gives procedures specifically suited for the subunit to be added.

Sequence β-Ala-Gly-Trp was assembled on RAM-TG (subst. 0.2 mmol/g). The terminal amino group was then alkylated using reductive amination procedure with a set of aliphatic, aromatic, and heterocyclic aldehydes. N-alkylated peptides were split of the resin using 95% TFA–5% $H_2O$ and the purity and the correct molecular weight of the resulting compounds were confirmed using HPLC and mass spectroscopy.

Procedure 1
solvent mixture 1 dichloromethane-methanol-acetic acid 80:20:1
solvent mixture 2 dimethylformamide-acetic acid 100:1

Schiff base formation: To a 50 mg of H-β-Ala-Gly-Trp-TentaGel S RAM washed 3× with solvent mixture 1 were added 200 µl of this mixture and 0.2 mmol of aldehyde. Resin was shaken for 2 hours, then washed 3× with solvent mixture 2. Another 0.2 mmol of aldehyde together with 200 µl of solvent mixture 2 were added and after 2 hours shaking resin was washed 3× with solvent mix.2 and 3× with solvent mix. 1.

Schiff base reduction: To a washed peptide-resin 200 µl of solvent mix. 1 and 200 µl of 1M solution of $NaBH_3CN$ in dimethylformamide were added. Resin was shaken for two 2 hours, then washed with solvent mix. 2 and reduction repeated in this mixture with 200 µl of 1M solution of $NaBH_3CN$ in DMF for another 2 hours. Resin was then washed with DMF. DCM, dried, and peptide was cleaved using TFA-5%$H_2O$.

Protocol 1
wash 3× with solvent mix. 1
add 200 µl of solvent mix. 1
add 0.2 mmol of aldehyde
shake for 2 hrs
wash 3× with solvent mix. 2
add 200 µl of solvent mix. 2
add 0.2 mmol of aldehyde
shake for 2 hrs
wash 3× with solvent mix. 2
wash 3× with solvent mix. 1
add 200 µl of solvent mix. 1
add 200 µl of 1M $NaBH_3CN$ in DMF
shake for 2 hrs
wash 3× with solvent mix. 2
add 200 µl of solvent mix. 2
add 200 µl of 1M $NaBH_3CN$ in DMF
shake for 2 hrs Procedure 2

Schiff base formation follows procedure A. Schiff base reduction follows procedure A with the difference that during the both reduction steps 0.01 mmol of aldehyde was added together with reduction reagent.

Protocol 2
wash 3× with solvent mix. 1
add 200 µl of solvent mix. 1
add 0.2 mmol of aldehyde
shake for 2 hrs
wash 3× with solvent mix. 2
add 200 µl of solvent mix. 2
add 0.2 mmol of aldehyde
shake for 2 hrs
wash 3× with solvent mix. 2
wash 3× with solvent mix. 1
add 200 µl of solvent mix. 1
add 200 µl of 1M $NaBH_3CN$ in DMF
add 0.01 mmol of aldehyde
shake for 2 hrs
wash 3× with solvent mix. 2
add 200 µl of solvent mix. 2
add 200 µl of 1M $NaBH_3CN$ in DMF
add 0.01 mmol of aldehyde
shake for 2 hrs Procedure 3 (one-pot reaction)

To a 50 mg of peptide-resin washed with solvent mixture 2 was added 200 µl of this mixture and 0.05 mmol of aldehyde. After 1 hour of shaking 50 µl of 1M solution of NaBH$_3$ in DMF was added and resin was allowed to shake for 2 hours. Then another 50 µl of reductive reagent was added and after 2 hours shaking the third portion (50 µl) of 1M solution of NaBH$_3$CN in DMF was added. Resin was shaken overnight and then worked up as above.

Protocol 3 wash 3x with solvent mix. 2 add 200 µl of solvent mix. 2 add 0.05 mmol of aldehyde shake for 1 hr add 50 µl of 1M NaBH$_3$CN in DMF shake for 2 hrs add 50 µl of 1M NaBH$_3$CN in DMF shake for 2 hrs add 50 µl of 1M NaBH$_3$CN shake overnight

TABLE 11

Reductive Amination

| Aldehyde (M.W.) | Prtcol. | MS (MH+) |
|---|---|---|
| benzaldehyde (421.2) | 1 | OK (422.2) |
| 2-hydroxybenzaldehyde (437.2) | 1 | OK (438.2) |
| 4-hydroxybenzaldehyde (437.2) | 1 | OK (438.2) |
| 4-hydroxybenzaldehyde (451.2) | 3 | OK (438.2) |
| 3-methoxy-4-hydroxybenzaldehyde (467.2) | 1 | OK (468.2) |
| 4-nitrobenzaldehyde (466.3) | 1 | OK (467.3) |
| 2-naphtaldehyde (471.3) | 1 | OK (472.3) |
| 3-phenoxybenzaldehyde (513.3) | 1 | OK (514.3) |
| 4-phenylbenzaldehyde (497.3) | 1 | OK (498.3) |
| 2-tolualdehyde (435.2) | 1 | OK (436.2) |
| 2-trifluoromethyl-benzaldehyde (489.3) | 2 | OK (490.3) |
| 1,3,5-trimethoxybenzaldehyde (511.3) | 1 | OK (512.3) |
| cyclohexanecarboxaldehyde (427.2) | 2 | OK (428.2) |
| 2-ethylbutyraldehyde (415.2) | 2 | OK (416.2) |
| 2-methylbutyraldehyde (401.2) | 2 | OK (402.2) |
| 2-methylpropionaldehyde (387.2) | 2 | OK (388.2) |
| 2-methyvaleraldehyde (415.2) | 2 | OK (416.2) |
| trimethylacetaldehyde (401.2) | 2 | OK (402.2) |
| quinoline-4-carboxaldehyde (472.3) | 3 | OK (402.2) |
| thiophene-2-carboxaldehyde (427.2) | 3 | OK (428.2) |

13. EXAMPLE: NON-SEQUENTIAL CODING OF A LIBRARY

We have tested nonsequential coding using both a model test compound and by construction of a nonpeptidic library.

13.1 Instruments, Materials and Procedures

Instrumentation: Both analytical and preparative HPLC were carried out on a modular Hitachi system using Vydac (0.46×250 mm, 5 µm, flow 1 ml/min) and Vydac (10×250 mm, 10 µm, flow 3 ml/min) C-18 columns, respectively.

Materials: Unless indicated otherwise, commercial-grade solvents were used without further purification. TentaGel (TG) resin (0.21 mmol/g) were received from Rapp-Polymere (Tubingen). Protected amino acids were obtained from Bachem (Torrance, Calif.), Advanced ChemTech (Louisville, Ky.), or Propeptide (Vert-le-Petit, France).

More than 100 coding subunits were synthesized on solid phase support. Lysine, ornithine, diaminobutyric and diaminopropionic acids were used as base building blocks. Fmoc-Lys(Boc), Fmoc-Orn(Boc), Fmoc-Dab(Boc) and Boc-Dap (Fmoc) were coupled first to amino TentaGel (0.21 mmol/g) by the usual DIC/HOBt procedure. After removing the side-chain protection, modifying carboxylic acids were coupled to the unprotected side-chains using the DIC/HOBt procedure, symmetrical anhydrides or acyl chlorides. All new coding amino acids synthesized were completely deprotected and submitted to Edman degradation in an Applied Biosystems ABI 477A Protein Sequencer. Retention times of novel PTH-AA were determined using an Applied Biosystems ABI 120A Analyzer with a PTH-222 Brownlee column (PTH C-18 5 micron, 220×2.1 mm). HPLC buffers: A—0.01M NaOAc, B—acetonitrile; gradient: 0.0–0.4 min—8% B, 0.4–38.0 min—8–60% B, 38.0–40.0 min—60–90% B; flow rate 230 ul/min. Peaks were detected at 269 nm. Table 14 lists the individual coding subunits and indicates the numbering system by which they are referred herein.

13.2 Synthesis of Model Sequences

The test compound sequences prepared were Tyr-Gly-Ala-Phe SEQ ID NO:12 and Phe-Gly-Ala-Phe SEQ ID NO:13, coded by doublets of amino acids (see Scheme XIC), and Tyr-Gly-Gly-Phe-Leu SEQ ID NO:14 and Phe (Cl)-Gly-Gly-Phe-Leu SEQ ID NO:15 (encoded by coding by Scheme XIB). These sequences were selected because Tyr-Gly-Ala-Phe SEQ ID NO:12 can be detected using an anti-β-endorphin antibody as the acceptor molecule and PheGly-Ala-Phe SEQ ID NO:13 is a negative control. Moreover, the fidelity and coding could be confirmed by directly sequencing the test peptides.

13.2.1 Materials and Methods

The purpose in synthesizing the model peptides was not to demonstrate a method of library synthesis, but rather to demonstrate the fidelity of coding. Therefore, the synthesis was not performed in successive steps of coupling test AA subunit followed by a pair of coding subunits, but rather using the more convenient scheme described below. Polymer carrier (TentaGel, 100 mg, 0.21 mmol/g, 90 um average particle size) onto which the sequence Boc-Ala-Gly-Val-Phe-bAla-Gly-bAla-Gly SEQ ID NO:15 was previously synthesized and which had undergone chymotrypsin treatment to differentiate the surface from the interior by cleavage of Phe (7 mg chymotrypsin in 30 ml of 0.1M Tris buffer pH 7.6 in 0.1M CaCl$_2$, 14 hours at 37° C.) was swollen in dimethylformamide (DMF) (swollen volume 0.5 ml), divided into two polypropylene syringes equipped with polypropylene fritted discs (Krchnak & Vagner, 1990, J. Pept. Res. 3: 182–193), Fmoc-Phe (3 equivalents with respect to all theoretically available amino groups) was coupled by diisopropylcarbodiimide (DIC) (3 equivalents) in the presence of N-hydroxybenzotriazole (HOBT) (3 equivalents) in DMF. After the disappearance of blue coloration (Krchnák et al., 1988 Coll. Czech. Chem. Commun. 53: 2542), the resin was washed (5× DMF) and Fmoc group was removed by the treatment of 50% piperidine in DMF (10 min). After washing by DMF (5×) and 2% HOBT in DMF (1×), the next amino acid was coupled. In this way alanine, glycine and tyrosine were attached to resin in the first syringe, and alanine, glycine and phenylalanine were attached to resin in the second syringe. The Fmoc group was removed as above and after washing with DMF the resin was treated with the solution (0.4M) of 2-chlorobenzyloxycarbonylsuccinimide in DMF overnight (after 3 h one equivalent of diisopropylethylamine was added). The Boc group was cleaved with 50% trifluoroacetic acid (TFA) in DCM (1 plus 20 min). After washing with DCM (3×) and DMF (4×), the resin was neutralized by washing with 10% diisopropylethylamine in DMF, washed by DMF (3×) and Fmoc-Lys(Dde) (3 eq) was coupled by the action of DIC and HOBT (3 eq each) in DMF (2 h). The resin was washed with DMF (5×) and the Fmoc group was cleaved by 50% piperidine in DMF (20 min), and resin was washed by DMF (3×). The mixture of amino acids coding for phenylalanine in position four of the test compound structure (Boc-Sar and Boc-Asp(OBzl) in a molar ratio of 1:1 (reflecting their relatively equivalent coupling reactivity which had previously been determined experimentally) was coupled using DIC and HOBT (3 eq each). The reaction was monitored by bromophenol blue method. The resin was washed by DMF (5×) and the Dde group was deprotected by 2% hydrazine hydrate in DMF (10 min). The resin was washed by DMF (5×), 2% HOBT in DMF, and Fmoc-Lys (Dde) was coupled, and Fmoc group removed. The procedure of coupling mixtures of Boc amino acids and Fmoc-Lys(Dde) was repeated two times (coupling the coding subunit mixtures of Ile and Val (2:1) and Lys(ClZ) and Glu(OBzl) (1.5:1)) and after deprotection of the Dde group, Boc-Lys(Fmoc) was coupled to the resin in both syringes. The Fmoc group was deprotected as above and after washing by DMF (5×) the mixture of butyric and propionic anhydrides (1:1 in the presence of one equivalent of triethylamine) were used for acylation of the free amino group in the first syringe and mixture of 4-phenylbutyric acid and 3-phenylpropionic acid was coupled to the resin in the second syringe by the action of DIC and HOBT. The resin was then deprotected by application of the mixture of TFA (82.5%), p-cresole (5%), thioanisole (5%), water (5%), and ethanedithiol (2.5%) (mixture K, (King, D. et al., 1990, Int. J. Pep. Prot. Res. 36: 255–266) for 2 hours and washed by DMF (4×) and 0.1%HCl in water (5×).

13.2.2 Model Compounds YGAF and FGAF Constructed with Coding

The two model peptides were synthesized on the surface of a "shaved" polyoxyethylene grafted polystyrene solid phase support (TentaGel). Coding molecules were synthesized in the interior of the TentaGel support and, thus, could not bind to the anti-β-endorphin antibody. Differentially seletive binding of the positive control test compound was validated using each test compound/bead construct alone, or as a mixture of both sequences, or after addition of a small number of specific beads to a library of compounds.

A non-sequential code was constructed on a polylysine backbone.

The code was as follows:

| Step | Subunit | Coding moiety |
|------|---------|---------------|
| 4 | Phe | butyryl-lysine, proprionyl-lysine |
| 4 | Tyr | φ-butyryl-lysine, φ-propionyl-lysine |
| 3 | Gly | Glu, Lys |
| 2 | Ala | Val, Ile |
| 1 | Phe | Asp, Sar |

The positive supports were selected after exposure to the antiβ-endorphin antibody. One cycle of Edman degradation identified the positive beads as YGAF because of the release of the φ-butyryl-lysine, φ-propionyl-lysine derivatives. Since the test compound sequence was present only on the surface of the bead, and this amounted to approximately 2% of the total amount of molecules attached to the bead, the signal of tyrosine detected in the first cycle (in which all the coding amino acid subunits were also cleaved) was extremely small. To confirm that we had actually detected the proper beads, the sequencing was repeated with 30 pooled beads to amplify the signal. In this case four cycles of sequencing directly revealed the YGAF test compound sequence.

13.3 Synthesis of the Diaminobenzoic Acid Based Library with Digital Coding

A library based on the diaminobenzoic acid was synthesized and encoded with a non-sequential code. The synthetic scheme of this library is given in the Scheme below. A list of the amino acids used in the first coupling step and the acids used in coupling steps, two and three, to the amino groups of the diaminobenzoic acid scaffold are given in Tables 12 and 13, respectively. Each table also gives the coding moieties corresponding to each species subunit of the test compound. The coding moieties in Table 13 are indicated by two digit numbers, e.g. 3/1, the chemical meanings of which are defined in Table 14.

Sequencing of several randomly chosen beads from this library confirm the possibility of one step decoding by Edman degradation.

13.3.1 Materials and Methods

Synthesis was performed on TentaGel resin (90 μm, 0.2 mmol/g). Fmoc deprotection: 50% piperidine in DMF, 10 min, wash with DMF 6 times, collect all washes, measure absorbance at 302 nm, calculate Fmoc release.

Alloc deprotection: Wash 3× DMF (2 min each). Add mixture of DMF/AcOH/NMM (5 ml,1 ml,0.5 ml) and bubble under Argon for 15 minutes. Add 150 mg tetrakis (triphenylphospine)palladium and bubble Argon for 3 hours. Wash 3× DMF. Wash 5× DCM.

Dde deprotection: Washed peptide resin was treated with 3% solution of hydrazine in DMF for 5 min and 30 min and followed by DMF wash.

Ddz deprotection: Peptide-resin was washed with DMF then with DCM and pretreated with 3% TFA in DCM for 5 min, twice. Third treatment with 3% TFA/DCM is done for 30 min. Thorough wash with DCM is followed by neutralization by 5% DIEA in DCM and then DCM and DMF wash.

Npys deprotection: Washed peptide resin was treated with 0.3M-HCl in dioxane for 5 min. and then 30 min. Deprotected peptide-resin was washed with dioxane, DCM, neutralized with 5% DIEA in DCM, and washed by DCM and DMF.

Coupling of amino acids: activate 3 molar excess of protected amino acid by BOP (molar ratio 1:1) in DMF. Check completeness of each condensation reaction (1.5–40 hrs) by ninhydrin test, or by chloranil test in the cases of coupling to secondary amino groups.

Side-chain deprotection: Wash with DCM 3 times, and deprotect using mixture K (82.5% TFA, 5% p-cresol, 5% thioanisole, 5% water, 2.5% ethanedithiol) for 5+120 min.

Final washes: neat TFA (3×), DCM (5×), DMF (10×), DMF/0.1% HCl (5×), 0.1% HCl (3×), and 0.01% HCl (4×).

13.3.2 Synthesis of the Library

Synthesis: TentaGel S NH2 (10 g) was preswollen in DMF and washed 5 times with DMF and subjected to solid synthesis using the following protocol which is schematically represented:

| Step | Reagent | |
|------|---------|---|
| 1 | 5% DIEA/DMF | 2 × 5 min |
| 2 | DMF wash | 10 × 2 min |
| 3 | Fmoc—Lys(Dde)/BOP | until Ninhydrin test is negative |
| 4 | 50% piperidine/DMF | 10 min |

-continued

| Step | Reagent | |
|---|---|---|
| 5 | Fmoc—Lys(Alloc)/BOP | until Ninhydrin test is negative |
| 6 | repeat step 4 | |
| 7 | Boc—Gly/BOP | until Ninhydrin test is negative |
| 8 | Pd catalyst | |
| 9 | repeat step 7 | |
| 10 | Fmoc—Gly/BOP | until Ninhydrin test is negative |
| 11 | repeat step 4 | |
| 12 | Fmoc-β-Ala/BOP | until Ninhydrin test is negative |
| 13 | repeat step 4 | |
| 14 | repeat step 10 | |
| 15 | repeat step 4 | |
| 16 | repeat step 12 | |
| 17 | TFA/DCM | |
| 18 | randomization and code 1 (table 3) amino acids/BOP | |
| 19 | repeat step 4 | |
| 20 | Ddz—Gly/BOP | |
| 21 | 3% hydrazine/DMF | |
| 22 | Fmoc-Lys(Dde)/BOP | until Ninhydrin test is negative |
| 23 | Allyl chloroformate | until Ninhydrin test is negative |
| 24 | 3% TFA/DCM | |
| 25 | Fmoc-amino acids R1/BOP (table 3) | |
| 26 | repeat step 4 | |
| 27 | scaffold I/TBTU | until Ninhydrin test is negative |
| 28 | Pd catalyst | |
| 29 | randomization + code 2 (table 4)/BOP | |
| 30 | HCl/dioxane | |
| 31 | 47 acids R 2 (table 4)/sym. anhydrides | |
| 32 | repeat step 4 | |
| 33 | randomization + code 3 | |
| 34 | 50 acids R 3 (table 4)/sym. anhydrides | |
| 35 | repeat step 21 | |
| 36 | code 3 (table 4)/BOP | |
| 37 | mixture K | |
| 38 | final wash | |

Protected library was stored in DMA/0.3% HOBt, deprotected library in 0.01% aqueous HCl.

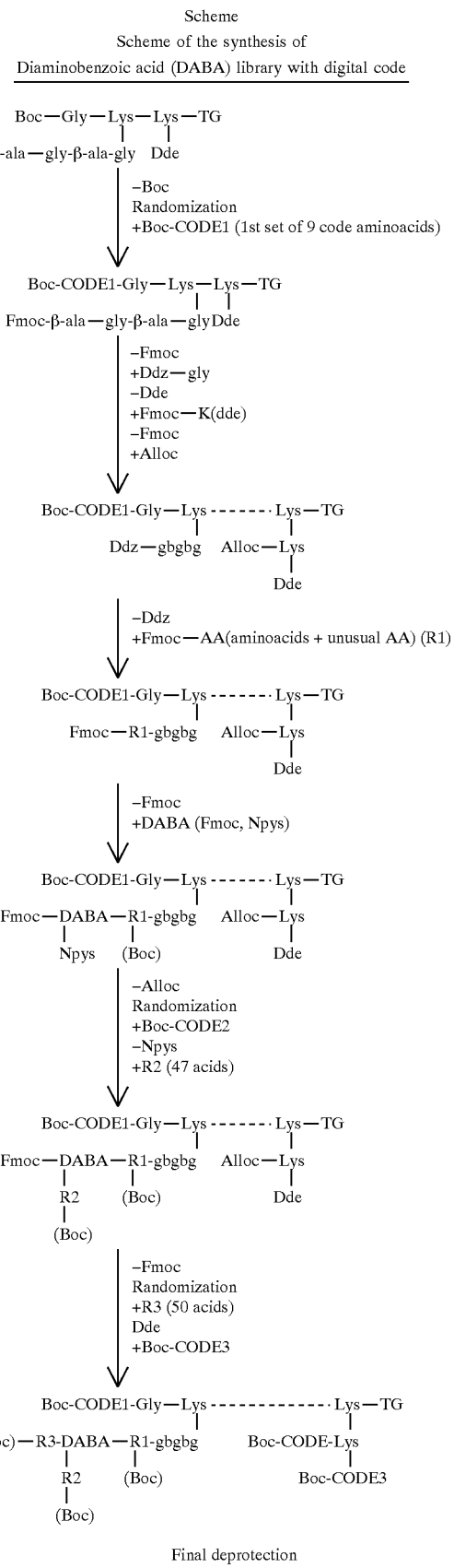

Scheme
Scheme of the synthesis of
Diaminobenzoic acid (DABA) library with digital code

-continued
Scheme
Scheme of the synthesis of Diaminobenzoic acid (DABA) library with digital code

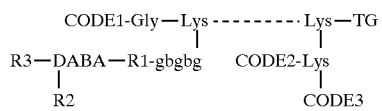

Screening of the Bar Coded Library

The library was screened according to a published procedure (Lam & Lebl, 1992, Immunomethods 1: 11–15). The library beads were first mixed with incrementally increasing double-distilled water. After extensive washing with PBS (137 mM NcCl, 2.7 mM KCl, 4.3 $Na_2HPO_4$, 1.4 mM $KH_2PO_4$, pH 7.2) with 0.1% Tween-20, the beads were incubated in 0.05% gelatin (w/v) to block any nonspecific binding. The beads were then incubated with 60 pM biotinylated anti-β-endorphin (clone 3-E 7, Boehringer Mannheim) in 2× PBS/Tween/gelatin overnight. After thorough washing, streptavidin-alkaline phosphatase was added. One hour later, the beads were washed, and the standard substrate for alkaline phosphatase, 5-bromo-4-chloro-3-indolyl phosphate, was added. The beads together with the substrate, were then transferred to petri dishes for color development. After 30 minutes to 1 hour, the positively colored beads were collected using a micropipette, washed with 6M guanidine hydrochloride, pH 1.0, and subjected to sequencing of the bar code.

TABLE 12

Amino Acid Doublets Used for Encoding Block R1
R1 = 29 Amino Acids

| Amino Acid | Code Elements |
|---|---|
| Gly | Ala Phe |
| Ala | Ala Ile |
| Dap | Aib Val |
| Pro | Aib Phe |
| Val | Aib Ile |
| Pipecolic acid | Val Phe |
| Leu | Val Ile |
| Asn | Phe Ile |
| Asp | Asn Gln |
| Orn | Asn Gly |
| Gln | Asn Ala |
| Glu | Asn Aib |
| 2-Pyridyl-Ala | Asn Val |
| Chg | Asn Phe |
| Phe | Asn Ile |
| Cha | Gln Gly |
| Arg | Gln Ala |
| Citruline | Gln Aib |
| Tetrahydroisoquinoline carboxylic acid | Gln Val |
| homoPhe | Gln Phe |
| N—Me—Gly | Gln Ile |
| Phe(p-F) | Gly Ala |
| Phe(p-Cl) | Gly Aib |
| Trp | Gly Val |
| Phe(p-NO2) | Gly Phe |
| Ala(1-Naph) | Gly Ile |
| 3,4-dichloro-Phe | Ala Aib |
| Lys(TFA) | Ala Val |
| Phe(p-Bz) | Ala Phe |

Aib = aminoisobutyric acid

TABLE 13

Acids used for randomizations of positions R2 and R3
(see scheme 1)
R2 = 47 Acids (this set less A16, A28 & A47)
R3 = 50 Acids

| Subunits of Test Compound | | Coding Amino Acids | |
|---|---|---|---|
| A01 | Acetic acid | ½ | ⅓ |
| A02 | Propionic acid | ½ | ¾ |
| A03 | Hexanoic acid | ½ | ⅔ |
| A04 | Isobutyric acid | ½ | ¾ |
| A05 | Trimethylacetic acid | ½ | NVal |
| A06 | Cyclopentanecarboxylic acid | ½ | Leu |
| A07 | Cyclohexanecarboxylic acid | ½ | Nle |
| A08 | Cyclohexylacetic acid | ½ | PheCl |
| A9 | 1-Adamantaneacetic acid | ½ | 15/4 |
| A10 | Glycine | ½ | 2'NaI |
| A11 | β-Alanine | ⅓ | ¾ |
| A12 | ε aminocaproic acid | ⅓ | ⅔ |
| A13 | γ-Guanidinobutyric acid | ⅓ | ¾ |
| A14 | Serine | ⅓ | NVal |
| A15 | Threonine | ⅓ | Leu |
| A16 | Cys(SMe) | ⅓ | Nle |
| A17 | Succinic acid | ⅓ | PheCl |
| A18 | Glutaric acid | ⅓ | 15/4 |
| A19 | cis-1,2-cyclohexanedicarboxylic acid | ⅓ | 2'NaI |
| A20 | Succinamic acid | ¾ | ⅔ |
| A21 | Benzoic acid | ¾ | ¾ |
| A22 | 1-Naphthylacetic acid | ¾ | NVal |
| A23 | Biphenylacetic acid | ¾ | Leu |
| A24 | Diphenylacetic acid | ¾ | Nle |
| A25 | 4-Aminobenzoic acid | ¾ | PheCl |
| A26 | 4-Dimethylaminobenzoic acid | ¾ | 15/4 |
| A27 | 4-Guanidinobenzoic acid | ¾ | 2'NaI |
| A28 | 3,4-dichlorophenylalanine | ⅔ | ¾ |
| A29 | 4-Nitrophenylacetic acid | ⅔ | Nval |
| A30 | 4,5-dimethoxy-2-nitrobenzoic acid | ⅔ | Leu |
| A31 | 4-Chlorobenzoic acid | ⅔ | Nle |
| A32 | α,α,α Trifluoro-p-toluic acid | ⅔ | PheCl |
| A33 | 4-Hydroxybenzoic acid | ⅔ | 15/4 |
| A34 | 4-Hydroxyphenyl acetic acid | ⅔ | 2'NaI |
| A35 | 3-(3,4,5-trimethoxyphenyl)proionic acid | ¾ | Nval |
| A36 | 4-(3-methyl-5-oxo-2-pyrazolin-1-yl) benzoic acid | ¾ | Leu |
| A37 | Proline | ¾ | Nle |
| A38 | 3-carboxyl-1,4-dimethyl-2-pyrroleacetic acid | ¾ | PheCl |
| A39 | 2-Methyl-4-nitro-1-imidazolepropionic acid | ¾ | 15/4 |
| A40 | 2-Amino-1-imidazoleacetic acid | ¾ | 2'NaI |
| A41 | 3-Amino-1,2,4-triazole-5-carboxylic acid | NVal | Leu |
| A42 | 4-Imidizoleacetic acid | NVal | Nle |
| A43 | Isonicotinic acid | NVal | PheCl |
| A44 | 2,3-Pyridinedicarboxylic acid | NVal | 15/4 |
| A45 | 2-Pyrazinecarboxylic acid | NVal | 2'NaI |
| A46 | 2,3-Pyrazinedicarboxylic acid | Leu | Nle |
| A47 | Pipecolic acid | Leu | PheCl |
| A48 | 1-Methylindole-2-carboxylic acid | Leu | 15/4 |
| A49 | 2-Methyl-3-indoleacetic acid | Leu | 2'NaI |
| A50 | Indole-4-carboxylic acid | Nle | PheCl |

TABLE 14

Amino Acid and Carboxylic Acid Matrix

| Species No. | α,β-Diamino propionic Acid(1) | α,γ-Diamino butyric Acid(2) | ornithine (3) | lysine (4) | Derivative |
|---|---|---|---|---|---|
| 1 | * | * | * | * | acetyl |
| 2 | * | * | * | * | propionyl |
| 3 | * | * | * | * | butyryl |
| 4 | * | * | * | * | valeryl |
| 5 | * | * | * | * | caproyl |

TABLE 14-continued

Amino Acid and Carboxylic Acid Matrix

| Species No. | α,β-Diamino propionic Acid(1) | α,γ-Diamino butyric Acid(2) | orni-thine (3) | lysine (4) | Derivative |
|---|---|---|---|---|---|
| 6 | * | * | * | * | pivaloyl |
| 7 | | * | * | * | c-hexanoyl |
| 8 | | * | * | * | trichloroacetyl |
| 10 | | * | * | * | phenylacetyl |
| 11 | | * | * | * | 2,2-diphenylacetyl |
| 12 | | * | * | * | phenylbutyryl |
| 13 | | * | * | * | 1-naphtylacetyl |
| 14 | | * | * | * | 2-naphtylacetyl |
| 15 | * | * | * | * | 1-adamantylcarbonyl |
| 16 | | * | * | * | 1-adamantylacetyl |
| 17 | | * | * | * | tosylglycyl |
| 18 | | * | * | * | dansylglycyl |
| 19 | * | * | * | * | benzoyl |
| 20 | * | * | * | * | succinamyl |
| 21 | | * | * | * | succinyl |
| 22 | | * | * | * | glutaryl |
| 23 | * | * | * | * | isobutyl |
| 24 | | * | * | * | 4-chlorobenzoyl |
| 25 | | * | * | * | 2,2-diphenylpropionyl |
| 26 | | * | * | * | N,N-dimethylglycyl |
| 27 | * | * | * | * | heptanoyl |
| 28 | * | * | * | * | octanoyl |
| 29 | * | * | * | * | 3,3-di-ph-propionyl |
| 30 | * | * | * | * | N,N-dimethylamino butyryl |
| 31 | * | * | * | * | 3-ph-propionyl |
| 32 | * | * | * | * | 4-bi-ph-carbonyl |
| 33 | * | * | * | * | 4-bi-ph-acetyl |
| 34 | * | * | * | * | crotonoyl |

(* means that the derivative was synthesized and analysed)

Code explanation: e.g. 19/4 means Lys(benzoyl)

14. EXAMPLE: MOLECULAR SCAFFOLDS

SCHEME XIX provides the chemical structures of 19 compounds that can be used to construct test compounds. The scheme indicates the site of attachment of the subunits of the test compounds by $R_n$.

Scheme XIX:

1.

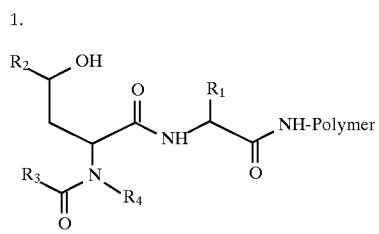

2.

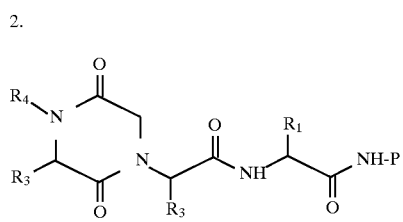

3.

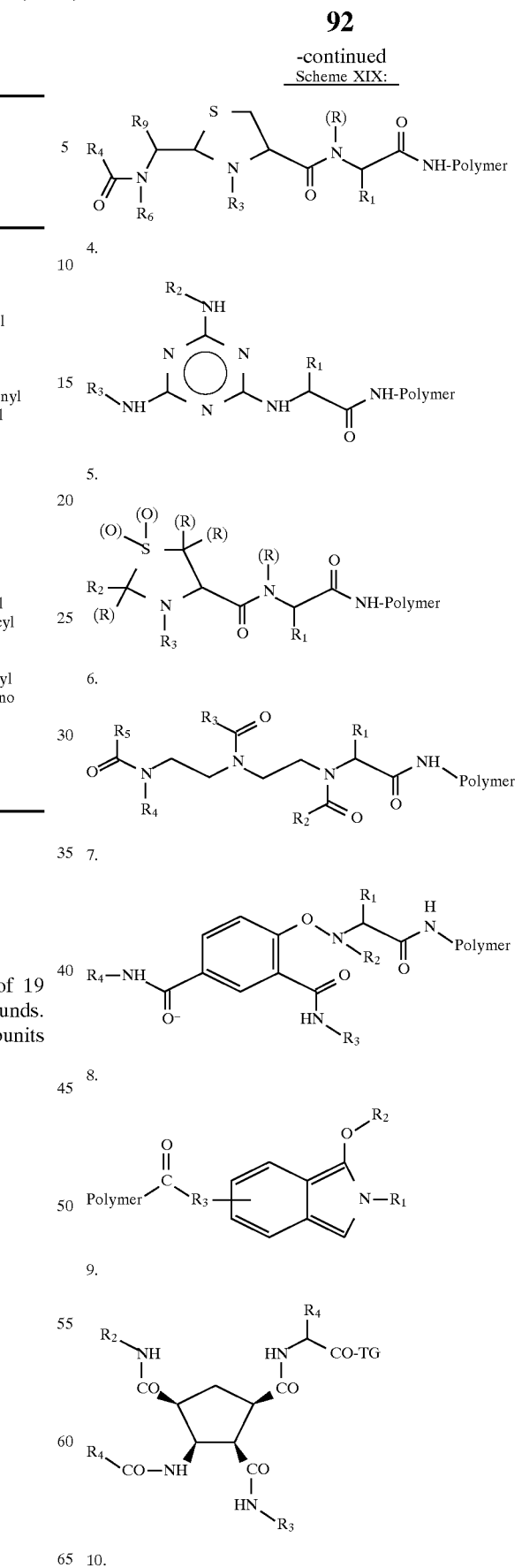

-continued
Scheme XIX:

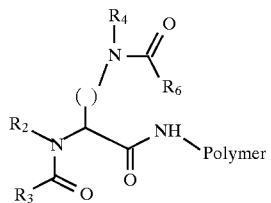
11.

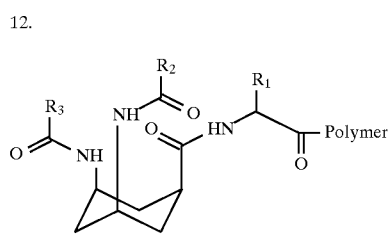
12.

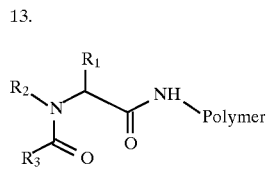
13.

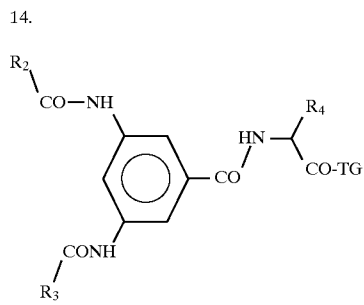
14.

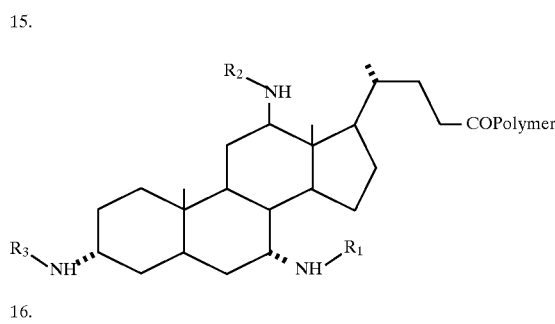
15.

16.

-continued
Scheme XIX:

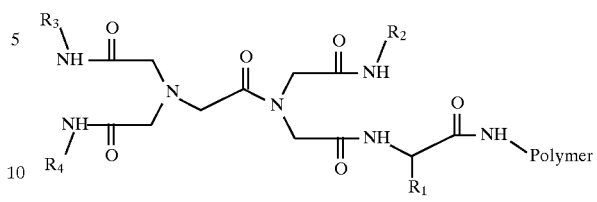
17.

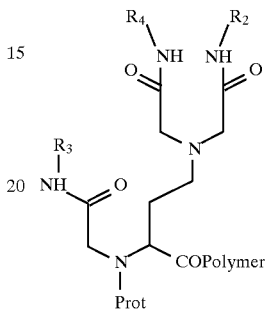
18.

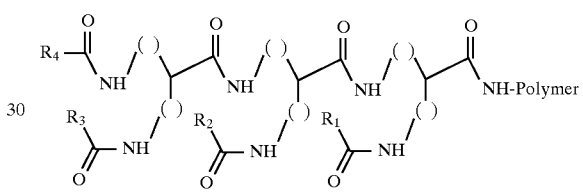
19.

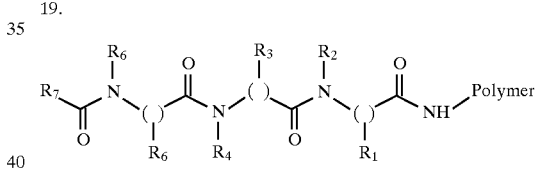

Table 15 below provides guidance concerning the types of subunits and the chemistry of their attachment to the molecular scaffold.

| Scaffold No. | Subunits | Chemistry of Coupling |
|---|---|---|
| 1. Amino Acid | amino acid | CO—NH coupling |
| Aldehyde/ | homoserine aldehyde | C—C bond formation |
| Organo-metal | alkyl- or arylmetal | |
| 2. Diketo- | amino acids | CO—NH coupling |
| piperazine | N-alkyl amino acids | reductive amination |
| 3. Substituted | amino acids | CO—NH coupling |
| Thioproline | cysteine | reductive amination |
| | amino acid aldehyde | |
| | alkyl or aryl acids | |
| 4. Substituted | amino acid | CO—NH coupling |
| Triazine | trichlorotriazine | reductive amination |
| | alkyl or aryl amines | |
| 5. Substituted | amino acids | CO—NH coupling |
| Thioproline | N-alkyl amino acids | thioaminal formation |
| Dioxide | cysteine | oxidation |
| | aldehyde, ketone | C-alkylation |
| 6. Acylated | amino acids | CO—NH coupling |
| Polyethylene- | glycinal | reductive amination |
| Diamine | alkyl or aryl acids | |

| Scaffold No. | Subunits | Chemistry of Coupling |
|---|---|---|
| 7. Benzenetricarboxylic Acid | amino acids<br>N-alkyl amino acids<br>1,2,4-benzenetricarboxylic acid | CO—NH coupling |
| 8. 2-S-alkyl (aryl) isoindol | subst. phthalic anhydride<br>alkyl or aryl amines<br>alkyl or aryl mercaptanes | isoindol synthesis |
| 9. Cyclopentane | N-alkyl amino acids<br>prim. or sec. amines<br>cyclopentantricarboxylic acid | CO—NH coupling |
| 10. Diacyldialkyl Diamino Acid | amino acids<br>aldehydes<br>alkyl or aryl acids | CO—NH coupling<br>reductive amination |
| 11. Extended Kemps Triacid | amino acids<br>Kemp's triacid<br>protected diamines | CO—NH coupling |
| 12. Kemps Triacid | amino acids<br>Kemp's triacid<br>alkyl or aryl acids | CO—NH coupling |
| 13. Akyl Acyl Amino Acid | amino acids<br>aldehydes<br>alkyl or aryl acids | CO—NH coupling |
| 14. Diaminobenzoic Acid | amino acids<br>3,5-diaminobenzoic acid<br>alkyl or aryl acids | CO—NH coupling |
| 15. Steroid | steroid skeleton<br>aldehydes | reductive amination<br>CO—NH coupling |
| 16. Bis-Iminodiacetic Acid | glycine<br>t-butylbromoacetate<br>alkyl or aryl amines | |
| 17. N-alkylated Iminodiacetic Acid | diaminobutanoic acid<br>t-butylbromoacetate<br>alkyl or aryl amines | CO—NH coupling<br>N-alkylation |
| 18. α,β,γ Peptidomimetic | diaminoacids<br>alkyl or aryl acids | CO—NH coupling |
| 19. N-Substituted Glycine Peptidomimetic | amino acids<br>aldehydes | CO—NH coupling<br>reductive amination |

What is claimed is:

1. A library for identifying and analyzing a ligand of an acceptor of interest comprising: a multiplicity of separate solid phase supports having a plurality of reactive functional groups; to each of which said supports are attached via said functional groups:

a) a species of test compound, said test compound comprised of a sequence of subunits; and b) one or more species of coding molecule, wherein the coding molecules that are attached to each support:
  i) are comprised of α-amino acids, and
  ii) are topologically segregated from the test compound that is attached to each said support, such that the coding molecule is in the interior of each said support, and the test compound is attached to greater than 90% of the reactive functional groups on the exterior of each said support;
wherein, on each said support:
  each species of coding molecule is different from the species of test compound; and
  the sequence of the subunits of the test compound is encoded by the species of coding molecules.

2. The library of claim 1 in which the test compound is non-sequencable.

3. The library of claim 2 in which the test compound is a polymer.

4. The library of claim 3 in which the test compound is a polymer selected from the group consisting of polyamide, polyester, polyurea, polyurethane, polycarbonate, polyamine, polyalkane, polyalkene, polyalcohol, polysulfide and polydisulfide.

5. The library of claim 2 in which the subunits of the test compound are linked by chemical bonds selected from the group consisting of amide, ester, urea, urethane, carbonate, amine, alkane, alkene, sulfide, and disulfide bonds.

6. The library of claim 2 in which the test compound is a molecular scaffold.

7. The library of claim 6 in which the molecular scaffold is selected from the group consisting of a steroid structure, a sugar, a heterocyclic structure, and a polyaromatic compound.

8. The library of claim 6 in which the molecular scaffold is an Amino Acid Aldehyde/Organo-metal, a Diketopiperazine, a Substituted Thioproline, a Substituted Triazine, a Substituted Thioproline Dioxide, an Acylated Polyethylene-Diamine, a Benzenetricarboxylic Acid, a 2-S-alkyl (aryl) isoindol, a Cyclopentane, a Diacyldialkyl Diamino Acid, an Extended Kemps Triacid, a Kemps Triacid, an Alkyl Acyl Amino Acid, a Diaminobenzoic Acid, a Steroid, a Bis-Iminodiacetic Acid, an N-alkylated, an Iminodiacetic Acid, an α,β,γ Peptidomimetic, or an N-Substituted Glycine Peptidomimetic.

9. The library of claim 1 in which the test compound is a polymer.

10. The library of claim 1 in which the coding molecule is a linear polypeptide.

11. The library of claim 1 in which the coding molecule is a branched polypeptide.

12. The library of claim 1 in which, on each said support, the sequence of subunits of the test compound is encoded by a single species of coding molecule.

13. The library of claim 1 in which, on each said support, the structure of the test compound is encoded by a plurality of species of coding molecules.

14. The library of claim 1 in which, on each said support, the structure of the test compound is encoded by one or more species of coding molecules, and the subunits of said coding molecule are arranged in a sequential code.

15. The library of claim 14 in which the sequence of subunits of the test compound is encoded by a single species of coding molecule.

16. The library of claim 14 in which the sequence of subunits of the test compound is encoded by a plurality of species of coding molecules.

17. The library of claim 1 in which the sequence of subunits of the test compound is encoded by one or more species of coding molecules, wherein the subunits of said coding molecule are arranged in a non-sequential code.

18. The library of claim 17 in which the sequence of subunits of the test compound is encoded by a single species of coding molecule.

19. The library of claim 17 in which the sequence of subunits of the test compound is encoded by a plurality of species of coding molecules.

20. The library of claim 17 in which the coding molecule comprises a polymer of diamino acids, having a first and a second amino moiety, in which:
  a) the first amino moiety forms a peptide bond linking said diamino acids to each other; and
  b) the second amino moiety is coupled to one of a multiplicity of species of α-amino acids.

21. The library of claim 17 in which the coding molecules are comprised of a derivative of α,β-diaminoproprionic acid, α,γ-diaminobutyric acid, ornithine and lysine, glutamic acid, aspartic acid, cysteine or penicillamine, wherein the derivative is formed by reaction of a carboxylic acid with an Nβ, Nγ or Nε amino moiety.

22. The library of claim 21 in which the derivative is selected from the group consisting of acetyl, propionyl, butyryl, valeryl, caproyl, pivaloyl, c-hexyl, trichloroacetyl, phenylacetyl, 2,2-diphenylacetyl, phenylbutyryl, 1-naphtylacetyl, 2-naphtylacetyl, 1-adamantylcarbonyl, 1-adamantylacetyl, tosylglycyl, dansylglycyl, benzoyl, succinamyl, succinyl, glutaryl, isobutyryl, 4-chlorobenzoyl, 2,2-diphenylpropionyl, N,N-dimethylglycyl, heptanoyl, octanoyl, 3,3-di-ph-propionyl, N,N-dimethylaminobutyryl, 3-ph-propionyl, 4-bi-ph-carbonyl, 4-bi-ph-acetyl and crotonyl.

23. The library of claim 2 in which a subunit of the species of test compound is attached by nucleophilic displacement and is selected from the group consisting of Ethylamine, i-Propylamine, Butylamine, i-Butylamine, Cyclopentylamine, Cyclohexylamine, Ethanolamine, 3-Aminopropanol, 1-Amino-2-propanol, 2-Methoxyethylamine, β-Ala-OtBu, Ethylendiamine(Boc), 2-(2-Aminoethyl)1-methylpyrrolidine, Benzylamine, Naphthalenemethylamine, 4-(Trifluoromethyl)-benzylamine, 2-Amino-1phenyl-ethanol, Tyramine, 4-Methoxy-benzylamine, 3,5-Dimethoxy-benzylamine and 4-(Dimethylamino)-benzylamine.

24. The library of claim 2 in which a subunit of the species of test compound is attached by acylation of a primary amine and is selected from the group consisting of γ-Guanidinobutyric, Succinamic, 1-Naphtylacetic, Diphenylacetic, Biphenylacetic, Pentafluorophenylacetic, 4-Trifluoromethylbenzoic, 4-Hydroxynbenzoic, 4-Hydroxyphenylacetic, 4-Aminophenylacetic, 3-Nitrophenylacetic, 2-Nitro-4,5,-dimethoxybenzoic, 3-(3, 4,5-trimethoxyphenyl)propionic, 4-Guanidinobenzoic, 4-Dimethylaminobenzoic, 4-(3-Methyl-5-oxo-2-pyrazolin-1-yl)benzoic, 1,4-Dimethyl-2,3-pyrroledicarboxylic, 2-Methyl-4-nitro-1-imidazolepropionic, 2-Amino-1-imidazoleacetic, 3-amino-1,2,4-triazole-5-carboxylic, 4-Imidazoleacetic, 2,3-Pyridinedicarboxylic, 2-Pyrazinecarboxylic, 2,3-Pyrazinedicarboxylic, 1-Methylindole-2-carboxylic, 2-Methyl-3-indoleacetic and Indole-4-carboxylic.

25. The library of claim 2 in which a subunit of the species of test compound is attached by reductive alkylation and is selected from the group consisting of 2-methylbutyraldehyde, 2-ethylbutyraldehyde, trimethylacetaldehyde, 2-methylvaleraldehyde, cyclohexanecarboxaldehyde, benzaldehyde, 4-nitrobenzaldehyde, 4-hydroxybenzaldehyde, vanillin, 2-thiophenecarboxaldehyde, pyridine-4-carboxaldehyde, α,α,α-trifluoro-o-tolualdehyde, 4-methoxybenzaldehyde, 1-acetylindole-3-caboxaldehyde, 4-carboxybenzaldehyde, beta-naphtaldehyde, 4-phenylbenzaldehyde, 3-phenoxybenzaldehyde and 2-hydroxybenzaldehyde.

26. The library of claim 1, wherein the test compound is non-sequencable.

27. The library of claim 26 in which a subunit of the species of test compound is attached by nucleophilic displacement and is selected from the group consisting of Ethylamine, i-Propylamine, Butylamine, i-Butylamine, Cyclopentylamine, Cyclohexylamine, Ethanolamine, 3-Aminopropanol, 1-Amino-2-propanol, 2-Methoxyethylamine, β-Ala-OtBu, Ethylendiamine(Boc), 2-(2-Aminoethyl)1-methylpyrrolidine, Benzylamine, Naphthalenemethylamine, 4-(Trifluoromethyl)-benzylamine, 2-Amino-1-phenyl-ethanol, Tyramine, 4-Methoxy-benzylamine, 3,5-Dimethoxy-benzylamine and 4-(Dimethylamino)-benzylamine.

28. The library of claim 26 in which a subunit of the species of test compound is attached by acylation of a primary amine and is selected from the group consisting of γ-Guanidinobutyric, Succinamic, 1-Naphtylacetic, Diphenylacetic, Biphenylacetic, Pentafluorophenylacetic, 4-Trifluoromethylbenzoic, 4-Hydroxynbenzoic, 4-Hydroxyphenylacetic, 4-Aminophenylacetic, 3-Nitrophenylacetic, 2-Nitro-4,5,-dimethoxybenzoic, 3-(3,4,5-trimethoxyphenyl)propionic, 4-Guanidinobenzoic, 4-Dimethylaminobenzoic, 4-(3-Methyl-5-oxo-2-pyrazolin-1-yl)benzoic, 1,4-Dimethyl-2,3-pyrroledicarboxylic, 2-Methyl-4-nitro-1-imidazolepropionic, 2-Amino-1-imidazoleacetic, 3-amino-1,2,4-triazole-5-carboxylic, 4-Imidazoleacetic, 2,3-Pyridinedicarboxylic, 2-Pyrazinecarboxylic, 2,3-Pyrazinedicarboxylic, 1-Methylindole-2-carboxylic, 2-Methyl-3-indoleacetic and Indole-4-carboxylic.

29. The library of claim 26 in which a subunit of the species of test compound is attached by reductive alkylation and is selected from the group consisting of 2-methylbutyraldehyde, 2-ethylbutyraldehyde, trimethylacetaldehyde, 2-methylvaleraldehyde, cyclohexanecarboxaldehyde, benzaldehyde, 4-nitrobenzaldehyde, 4-hydroxybenzaldehyde, vanillin, 2-thiophenecarboxaldehyde, pyridine-4-carboxaldehyde, α,α,α-trifluoro-o-tolualdehyde, 4-methoxybenzaldehyde, 1-acetylindole-3-caboxaldehyde, 4-carboxybenzaldehyde, beta-naphtaldehyde, 4-phenylbenzaldehyde, 3-phenoxybenzaldehyde and 2-hydroxybenzaldehyde.

30. The library of claim 26 in which the test compound is a molecular scaffold.

31. The library of claim 30 in which the molecular scaffold is an Amino Acid Aldehyde/Organo-metal, a Diketopiperazine, a Substituted Thioproline, a Substituted Triazine, a Substituted Thioproline Dioxide, an Acylated Polyethylene-Diamine, a Benzenetricarboxylic Acid, a 2-S-alkyl (aryl) isoindol, a Cyclopentane, a Diacyldialkyl Diamino Acid, an Extended Kemps Triacid, a Kemps Triacid, an Alkyl Acyl Amino Acid, a Diaminobenzoic Acid, a Steroid, a Bis-Iminodiacetic Acid, an N-alkylated, an Iminodiacetic Acid, an α,β,γ Peptidomimetic, or an N-Substituted Glycine Peptidomimetic.

32. A library for identifying and analyzing a ligand of an acceptor of interest comprising: a multiplicity of separate solid phase supports; to each of which are attached:

a) a species of test compound, said test compound comprised of a sequence of subunits, in which the species of a test compound is attached to each support through a cleavable linker; and b) one or more species of coding molecules, wherein the coding molecules are attached to each said support through a non-cleavable or separately cleavable linker, and are comprised of α-amino acids;

wherein, on each said support:

each species of coding molecule is different from the species of test compound;

the sequence of the subunits of the test compound is encoded by the species of coding molecules; and the coding molecules have subunits arranged in a non-sequential code.

33. The library of claim 32 in which the test compound is non-sequencable.

34. The library of claim 33 in which the test compound is a polymer.

35. The library of claim 34 in which the test compound is a polymer selected from the group consisting of polyamide, polyester, polyurea, polyurethane, polycarbonate, polyamine, polyalkane, polyalkene, polyalcohol, polysulfide and polydisulfide.

36. The library of claim 33 in which the subunits of the test compound are linked by chemical bonds selected from the group consisting of amide, ester, urea, urethane, carbonate, amine, alkane, alkene, sulfide, and disulfide bonds.

37. The library of claim 33 in which the test compound is a molecular scaffold.

38. The library of claim 37 in which the molecular scaffold is selected from the group consisting of a steroid structure, a sugar, a heterocyclic structure, and a polyaromatic compound.

39. The library of claim 37 in which the molecular scaffold is an Amino Acid Aldehyde/Organo-metal, a Diketopiperazine, a Substituted Thioproline, a Substituted Triazine, a Substituted Thioproline Dioxide, an Acylated Polyethylene-Diamine, a Benzenetricarboxylic Acid, a 2-S-alkyl (aryl) isoindol, a Cyclopentane, a Diacyldialkyl Diamino Acid, an Extended Kemps Triacid, a Kemps Triacid, an Akyl Acyl Amino Acid, a Diaminobenzoic Acid, a Steroid, a Bis-Iminodiacetic Acid, an N-alkylated, an Iminodiacetic Acid, an α,β,γ Peptidomimetic, or an N-Substituted Glycine Peptidomimetic.

40. The library of claim 32 in which the coding molecule is a branched polypeptide.

41. The library of claim 32 in which, on each said support, the structure of the test compound is encoded by a plurality of species of coding molecules.

42. The library of claim 32 in which the coding molecule comprises a polymer of diamino acids, having a first and a second amino moiety, in which:

a) the first amino moiety forms a peptide bond linking said diamino acids to each other; and b) the second amino moiety is coupled to one of a multiplicity of species of α-amino acids.

43. The library of claim 32 in which the coding molecules are comprised of a derivative of α,β-diaminoproprionic acid, α,γ-diaminobutyric acid, ornithine and lysine, glutamic acid, aspartic acid, cysteine or penicillamine, wherein the derivative is formed by reaction of a carboxylic acid with an Nβ, Nγ or Nε amino moiety.

44. The library of claim 43 in which the derivative is selected from the group consisting of acetyl, propionyl, butyryl, valeryl, caproyl, pivaloyl, c-hexyl, trichloroacetyl, phenylacetyl, 2,2-diphenylacetyl, phenylbutyryl, 1-naphtylacetyl, 2-naphtylacetyl, 1-adamantylcarbonyl, 1-adamantylacetyl, tosylglycyl, dansylglycyl, benzoyl, succinamyl, succinyl, glutaryl, isobutyryl, 4-chlorobenzoyl, 2,2-diphenylpropionyl, N,N-dimethylglycyl, heptanoyl, octanoyl, 3,3-di-ph-propionyl, N,N-dimethylaminobutyryl, 3-ph-propionyl, 4-bi-ph-carbonyl, 4-bi-ph-acetyl and crotonyl.

45. The library of claim 33 in which a subunit of the species of test compound is attached by nucleophilic displacement and is selected from the group consisting of Ethylamine, i-Propylamine, Butylamine, i-Butylamine, Cyclopentylamine, Cyclohexylamine, Ethanolamine, 3-Aminopropanol, 1-Amino-2-propanol, 2-Methoxyethylamine, β-Ala-OtBu, Ethylendiamine(Boc), 2-(2-Aminoethyl)1-methylpyrrolidine, Benzylamine, Naphthalene-methylamine, 4-(Trifluoromethyl)-benzylamine, 2-Amino-1-phenyl-ethanol, Tyramine, 4-Methoxy-benzylamine, 3,5-Dimethoxy-benzylamine and 4-(Dimethylamino)-benzylamine.

46. The library of claim 33 in which a subunit of the species of test compound is attached by acylation of a primary amine and is selected from the group consisting of γ-Guanidinobutyric, Succinamic, 1-Naphtylacetic, Diphenylacetic, Biphenylacetic, Pentafluorophenylacetic, 4-Trifluoromethylbenzoic, 4-Hydroxynbenzoic, 4-Hydroxyphenylacetic, 4-Aminophenylacetic, 3-Nitrophenylacetic, 2-Nitro-4,5-dimethoxybenzoic, 3-(3,4,5-trimethoxyphenyl)propionic, 4-Guanidinobenzoic, 4-Dimethylaminobenzoic, 4-(3-Methyl-5-oxo-2-pyrazolin-1-yl)benzoic, 1,4-Dimethyl-2,3-pyrroledicarboxylic, 2-Methyl-4-nitro-1-imidazolepropionic, 2-Amino-1-imidazoleacetic, 3-amino-1,2,4-triazole-5-carboxylic, 4-Imidazoleacetic, 2,3-Pyridinedicarboxylic, 2-Pyrazinecarboxylic, 2,3-Pyrazinedicarboxylic, 1-Methylindole-2-carboxylic, 2-Methyl-3-indoleacetic and Indole-4-carboxylic.

47. The library of claim 33 in which a subunit of the species of test compound is attached by reductive alkylation and is selected from the group consisting of 2-methylbutyraldehyde, 2-ethylbutyraldehyde, trimethylacetaldehyde, 2-methylvaleraldehyde, cyclohexanecarboxaldehyde, benzaldehyde, 4-nitrobenzaldehyde, 4-hydroxybenzaldehyde, vanillin, 2-thiophenecarboxaldehyde, pyridine-4-carboxaldehyde, α,α,α-trifluoro-o-tolualdehyde, 4-methoxybenzaldehyde, 1-acetylindole-3-caboxaldehyde, 4-carboxybenzaldehyde, beta-naphtaldehyde, 4-phenylbenzaldehyde, 3-phenoxybenzaldehyde and 2-hydroxybenzaldehyde.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) NAME/KEY: Other
        ( B ) LOCATION: 1
        ( D ) OTHER INFORMATION: Xaa=beta alanine
        ( A ) NAME/KEY: Other
        ( B ) LOCATION: 3
        ( D ) OTHER INFORMATION: Xaa=beta alanine ( x i ) SEQUENCE DESCRIPTION: SEQ ID NO:1:

Xaa  Gly  Xaa  Gly
1

( 2 ) INFORMATION FOR SEQ ID NO:2:

( i ) SEQUENCE CHARACTERISTICS:
        ( A ) LENGTH: 4 amino acids
        ( B ) TYPE: amino acid ( C ) STRANDEDNESS:
            ( D ) TOPOLOGY: unknown ( i i ) MOLECULE TYPE: peptide ( x i ) SEQUENCE DESCRIPTION: SEQ ID NO:2:

Tyr  Gly  Gly  Phe
 1

( 2 ) INFORMATION FOR SEQ ID NO:3:

( i ) SEQUENCE CHARACTERISTICS:
            ( A ) LENGTH: 4 amino acids
            ( B ) TYPE: amino acid
            ( C ) STRANDEDNESS:
            ( D ) TOPOLOGY: unknown ( i i ) MOLECULE TYPE: peptide ( x i ) SEQUENCE DESCRIPTION: SEQ ID NO:3:

Tyr  Gly  Pro  Phe
 1

( 2 ) INFORMATION FOR SEQ ID NO:4:

( i ) SEQUENCE CHARACTERISTICS:
            ( A ) LENGTH: 4 amino acids
            ( B ) TYPE: amino acid
            ( C ) STRANDEDNESS:
            ( D ) TOPOLOGY: unknown ( i i ) MOLECULE TYPE: peptide ( x i ) SEQUENCE DESCRIPTION: SEQ ID NO:4:

Tyr  Gly  Gly  Leu
 1

( 2 ) INFORMATION FOR SEQ ID NO:5:

( i ) SEQUENCE CHARACTERISTICS:
            ( A ) LENGTH: 4 amino acids
            ( B ) TYPE: amino acid
            ( C ) STRANDEDNESS:
            ( D ) TOPOLOGY: unknown ( i i ) MOLECULE TYPE: peptide ( x i ) SEQUENCE DESCRIPTION: SEQ ID NO:5:

His  Pro  Gln  Phe
 1

( 2 ) INFORMATION FOR SEQ ID NO:6:

( i ) SEQUENCE CHARACTERISTICS:
            ( A ) LENGTH: 6 amino acids
            ( B ) TYPE: amino acid
            ( C ) STRANDEDNESS:
            ( D ) TOPOLOGY: unknown ( i i ) MOLECULE TYPE: peptide ( i x ) FEATURE:
            ( A ) NAME/KEY: Other
            ( B ) LOCATION: 2
            ( D ) OTHER INFORMATION: Xaa=beta alanine
            ( A ) NAME/KEY: Other
            ( B ) LOCATION: 4
            ( D ) OTHER INFORMATION: Xaa=beta alanine ( x i ) SEQUENCE DESCRIPTION: SEQ ID NO:6:

Gly  Xaa  Gly  Xaa  Gly  Lys

```
     1               5
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:7:

```
Tyr   Gly   Gly   Phe   Leu
 1                        5
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:8:

```
Leu   His   Pro   Gln   Phe
 1                        5
```

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:9:

```
Leu   His   Pro   Gln   Phe   Tyr   Gly
 1                        5
```

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:10:

```
Leu   His   Phe   Gln   Phe
 1                        5
```

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:11:

```
Tyr   Gly   Gly   Phe   Leu   Gly   Gly   Gly
```

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:12:

Tyr Gly Ala Phe
1

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:13:

Phe Gly Ala Phe
1

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:14:

Phe Gly Gly Phe Leu
1                    5

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Other
        (B) LOCATION: 5
        (D) OTHER INFORMATION: Xaa=beta alanine
        (A) NAME/KEY: Other
        (B) LOCATION: 7
        (D) OTHER INFORMATION: Xaa=beta alanine (xi) SEQUENCE DESCRIPTION: SEQ ID NO:15:

Ala Gly Val Phe Xaa Gly Xaa Gly
1                    5